US007368438B2

(12) United States Patent
Plourde, Jr. et al.

(10) Patent No.: US 7,368,438 B2
(45) Date of Patent: May 6, 2008

(54) NON-NUCLEOTIDE COMPOSITIONS AND METHOD FOR INHIBITING PLATELET AGGREGATION

(75) Inventors: Robert Plourde, Jr., Chapel Hill, NC (US); Sammy R. Shaver, Chapel Hill, NC (US); José L. Boyer, Chapel Hill, NC (US); Melwyn A. Abreo, Jamul, CA (US); Lorenzo J. Alfaro-Lopez, San Marcos, CA (US); Yangbo Feng, Palm Beach Gardens, FL (US); Daniel F. Harvey, San Diego, CA (US); Tatyana V. Khasonova, San Diego, CA (US); Chi Tu, San Diego, CA (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 299 days.

(21) Appl. No.: 10/971,766

(22) Filed: Oct. 21, 2004

(65) Prior Publication Data

US 2005/0159388 A1     Jul. 21, 2005

Related U.S. Application Data

(60) Provisional application No. 60/513,845, filed on Oct. 21, 2003.

(51) Int. Cl.
*A01N 43/04* (2006.01)
*A61K 31/70* (2006.01)
*C07H 19/16* (2006.01)

(52) U.S. Cl. .................... 514/46; 536/27.23
(58) Field of Classification Search ............ None
See application file for complete search history.

(56) References Cited

U.S. PATENT DOCUMENTS

| | | | |
|---|---|---|---|
| 3,321,463 A | 5/1967 | Moffatt et al. | |
| 4,794,174 A | 12/1988 | Secrist, III | 536/26 |
| 5,049,550 A | 9/1991 | Zamecnik | 514/47 |
| 5,292,725 A * | 3/1994 | Prendergast | 514/46 |
| 5,409,937 A | 4/1995 | Whittaker et al. | 514/303 |
| 5,681,823 A | 10/1997 | Kim et al. | 514/47 |
| 5,747,496 A | 5/1998 | Cox et al. | 514/258 |
| 6,037,343 A | 3/2000 | Ali | 514/252 |
| 6,040,317 A | 3/2000 | Duggan et al. | 514/317 |
| 6,369,064 B1 | 4/2002 | Brown et al. | 514/258 |
| 6,767,910 B1 | 7/2004 | Teobald | 514/261.1 |
| 2004/0138229 A1 | 7/2004 | Bryant et al. | 514/253.06 |
| 2005/0267134 A1* | 12/2005 | Plourde et al. | 514/263.22 |

FOREIGN PATENT DOCUMENTS

| | | |
|---|---|---|
| EP | 0 066 918 A | 12/1982 |
| EP | 1 348 466 A2 | 10/2003 |
| WO | WO 98/28300 A1 | 7/1998 |
| WO | WO 99/05142 A1 | 2/1999 |
| WO | WO 99/05143 A1 | 2/1999 |
| WO | WO 99/05144 A1 | 2/1999 |
| WO | WO99/06053 | 2/1999 |
| WO | WO 99/41254 A1 | 8/1999 |
| WO | WO 00/04021 A1 | 1/2000 |
| WO | WO00/33080 | 6/2000 |
| WO | WO 01/36438 A1 | 5/2001 |
| WO | WO 01/40243 A2 | 6/2001 |
| WO | WO 01/40246 A1 | 6/2001 |
| WO | WO 01/94368 A1 | 12/2001 |
| WO | WO 02/16381 A2 | 2/2002 |
| WO | WO 02/096428 A1 | 12/2002 |

OTHER PUBLICATIONS

Lambertucci, et al. "2-Phenylhydroxypropynyladenosine Derivatives as High Potent Agonists at A2B Adenosine Receptor Subtype," Nucleosides, Nucleotides & Nucleic Acids, 2003, vol. 22, Nos. 5-8, pp. 809-812.*
Abstracts of Papers, 225TH ACS National Meeting, New Orleans, LA; Mar. 2003; MEDI-016.
André, et al., "$P2Y_{12}$ regulates platelet adhesion/activation, thrombus growth, and thrombus stability in injured arteries," *J. Clin. Invest.*, 112: 398-406 (2003).
Antiplatelet Trialists' Collaboration, "Collaborative overview of randomized trials of antiplatelet therapy Prevention of death, myocardial antiplatelet therapy in various categories of patients," *Br. Med. J.* 308: 81-106 (1994).
Antiplatelet Trialists' Collaboration, "Collaborative overview of randomized trials of antiplatelet therapy—II: Maintenance of vascular antiplatelet therapy," *Br. Med. J.* 308: 159-168 (1994).
Baraldi, et al., "Novel $N^6$-(Substituted-phenylcarbamoyl)adenosine-5'-uronamides as Potent Agonists for $A_3$ Adenosine Receptors," *Journal of Medicinal Chemistry* 39(3): 802-806 (1996).
Bennett, et al., "Thrombotic Thrombocytopenic Purpura Associated with Clopidogrel," *N. Engl. J. Med.* 342: 1773-1777 (2000).
Bennett, et al., "Thrombotic Thrombocytopenic Purpura Associated with Ticlopidine," *Ann. Intern. Med.* 128: 541-544 (1998).
Bernat, et al., "Effect of Various Antiplatelet Agents on Acute Arterial Thrombosis in the Rat," *Thromb. Haemostas.* 70: 812-826 (1993).
Brown, et al., "Matrix Metalloproteinase Inhibitors Containing a (Carboxyalkyl)amino Zinc Ligand: Modification of the P1 and P2' Residues," *J. Med. Chem.* 37(5): 674-688 (1994).
Bush, et al., "Effects of the selective thromboxane synthetase inhibitor dazoxiben on variations in cyclic blood flow in stenosed canine coronary arteries," *Circulation* 69: 1161-1170 (1984).

(Continued)

*Primary Examiner*—Shaojia Anna Jiang
*Assistant Examiner*—Layla Bland
(74) *Attorney, Agent, or Firm*—Howrey LLP; Viola T. Kung

(57) ABSTRACT

This invention is directed to a method of preventing or treating diseases or conditions associated with platelet aggregation. The method is also directed to a method of treating thrombosis or related disorders. The method comprises administering to a subject a pharmaceutical composition comprising an effective amount of a non-nucleotide compound, preferably a $P2Y_{12}$ receptor antagonist compound, wherein said amount is effective to inhibit platelet aggregation. The compounds useful for this invention include compounds of general Formula I and III-XI, or salts, hydrates, and solvates thereof. The present invention also provides novel compounds according to Formula I and III-XI.

14 Claims, No Drawings

OTHER PUBLICATIONS

Camaioni, et al., "Adenosine Receptor Agonists: Synthesis and Biological Evaluation of the Diastereoisomers of 2-(3-Hydroxy-3-phenyl-1-propyn-1-yl)NECA," *Bioorganic & Medicinal Chemistry* 5(12): 2267-2275 (1997).

Cristalli, et al., "2-Aralkynyl and 2-Heteroalkynyl Derivativse of Adenosine-5'-*N*-ethyluronamide as Selective $A_{2a}$ Adenosine Receptor Agonists," *Journal of Medicinal Chemistry* 38(9): 1462-1472 (1995).

Dangelmaier, et al., "Potentiation of Thromboxane $A_2$-induced Platelet Secretion by Gi Signaling through the Phosphoinositide-3 Kinase Pathway," *Thromb. Haemostas.* 85: 341-348 (2001).

The EPIC investigators; Califf, R.M. coordinating author; "Use of a Monoclonal Antibody Directed Against the Platelet Glycoprotein IIb/IIIa Receptor in High-Risk Coronary Angioplasty," *New Engl. J. Med.* 330: 956-961 (1994).

Folts, et al., "Platelet Aggregation in Partially Obstructed Vessels and its Elimination with Aspirin," *Circulation* 54: 365-370 (1976).

Frederick et al., "The Protective Dose of the Potent GPIIb/IIIa Antagonist SC-54701A is Reduced When Used in Combination with Aspirin and Heparin in a Canine Model of Coronary Artery Thrombosis," *Circulation* 93: 129-134 (1996).

Gachet, C., "ADP Receptors of Platelets and their Inhibition," *Thromb. Haemostas.* 86: 222-232 (2001).

Garcia-Echeverria, C., "A base labile handle for solid phase organic chemistry," *Tetrahedron Lett.*, 38: 8933-8937 (1997).

Gelger, et al., "Specific Impairment of Human Platelet $P2Y_{AC}$ ADP Receptor-Mediated Signaling by the Antiplatelet Drug Clopidogrel," *Arterioscler. Thromb. Vasc. Biol.* 19: 2007-2011 (1999).

The GUSTO IIa investigators; "Randomized Trial of Intravenous Heparin Versus Recombinant Hirudin for Acute Coronary Syndromes," *Circulation* 90: 1631-1637 (1994).

Hass, et al., "A Randomized Trial Comparing Ticlopidine Hydrochloride with Aspirin for the Prevention of Stroke in High-Risk Patients," *N. Engl. J. Med.* 321: 501-507 (1989).

Hechler, et al., "A Role of the Fast ATP-gated $P2X_1$ Cation Channel in Thrombosis of Small Arteries In Vivo," *J. Exp. Med.* 198: 661-667 (2003).

Herbert, et al., "Inhibitory Effect of Clopidogrel on Platelet Adhesion and Intimal Proliferation After Arterial Injury in Rabbits," *Arterioscl. Thromb.* 13: 1171-1179 (1993).

Hourani, et al., "Effects of the $P_2$-purinoceptor antagonist, suramin, on human platelet aggregation induced by adenosine 5'-diphosphate," *Br. J. Pharmacology* 105: 453-457 (1992).

The IMPACT-II Investigators; "Randomised placebo-controlled trial of effect of eptifibatide on complications of percutaneous coronary intervention: IMPACT-II," *Lancet* 349: 1422-1428 (1997).

Ingall, et al., "Antagonists of the Platelet $P_{2T}$ Receptor: A Novel Approach to Antithrombotic Therapy," *J. Med. Chem.* 42: 213-220 (1999).

Jacobson, et al., "Structure-Activity Relationships of 9-Alkyladenine and Ribose-Modified Adenosine Derivatives at Rat $A_3$ Adenosine Receptors," *Journal of Medicinal Chemistry* 38(10): 1720-12735 (1995).

Jagroop, et al., "Both the ADP receptors $P2Y_1$ and $P2Y_{12}$, play a roll in controlling shape change in human platelets," *Platelets* 14: 15-20 (2003).

Lee, et al., "*N*-Alkoxysulfamide, *N*-Hydroxysulfamide, and Sulfamate Analogues of Methionyl and Isoleucyl Adenylates as Inhibitors of Methionyl-tRNA and Isoleucyl-tRNA Synthetases," *Bioorganic & Medicinal Chemistry Letters* 13(6): 1087-1092 (2003).

Lekstrom and Bell, "Aspirin in the Prevention of Thrombosis," *Medicine* 70: 161-177 (1991).

Lyga and Secrist III, "Synthesis of Chain-Extended and C-6' Functionalized Precursors of the Nucleoside Antibiotic Sinefungin," *Journal of Organic Chemistry* 48(12): 1982-1988 (1983).

Maffrand, et al., "ADP Plays a Key Role in Thrombogenesis in Rats," *Thromb. Haemostas.* 59: 225-230 (1988).

McKee, et al., "Aspirin Resistance in Cardiovascular Disease: A Review of Prevalence, Mechanisms, and Clinical Significance," *Thromb. Haemostas.* 88: 711-715 (2002).

Mickelson, et al., "Antiplatelet Antibody [7E3 F(ab')$_2$] Prevents Rethrombosis After Recombinant Tissue-Type Plasminogen Activator-Induced Coronary Artery Thrombolysis in a Canine Model," *Circulation* 81: 617-627 (1990).

Mitsunobu, O., "The Use of Diethyl Azodicarboxylate and Triphenylphosphine in Synthesis and Transformation of Natural Products," *Synthesis* 1-28 (1981).

Neuhaus, et al., "Safety Observations from the Pilot Phase of the Randomized r-Hirudin for Improvement of Thrombolysis (HIT-III) Study," *Circulation*, 90: 1638-1642 (1994).

Quinn and Fitzgerald, "Ticlopidine and Clopidogrel," *Circulation* 100: 1667-1672 (1999).

The RESTORE investigators; "Effects of Platelet Glycoprotein IIb/IIIa Blockade with Tirofiban on Adverse Cardiac Events in Patients with Unstable Angina or Acute Myocardial Infarction Undergoing Coronary Angioplasty," *Circulation* 96: 1445-1453 (1997).

Santosh and Balasubramanian, "A Facile and Stereoselective Synthesis of Arylethers of Vicinal Bromohydrins by Mitsunobu Reaction," *Synthetic Communications*, 24(8): 1049-1062 (1994).

Savi, et al. "Identification and Biological Activity of the Active Metabolite of Clopidogrel," *Thromb. Haemostas.* 84: 891-896 (2000).

Secrist III and Talekar, "5'-C-Chain-extended Adenosine Derivatives Related to Sinefungin, Synthesis and Biological Activity," *Nucleosides & Nucleotides* 9(4): 619-627 (1990).

Shebuski, et al., "Acceleration of Recombinant Tissue-Type Plasminogen Activator-Induced Thrombolysis and Prevention of Reocclusion by the Combination of Heparin and the Arg-Gly-Asp-Containing Peptide Bitistatin in a Canine Model of Coronary Thrombosis," *Circulation* 82: 169-177 (1990).

The TIMI 9a investigators; "Hirudin in Acute Myocardial Infarction," *Circulation* 90: 1624-1630 (1994).

Tschopp, et al., *Coron. Artery Dis.* 4: 809-817 (1993).

Weber, et al., "Low-Dose Aspirin Versus Anticoagulants for Prevention of Coronary Graft Occlusion,"*Am. J. Cardiol* 66: 1461-1468 (1990).

Adamiak and Stawiński, "A Highly Effective Route to N,N'-Disubstituted Ureas Under Mild Conditions. An Application to the Synthesis of tRNA Anticodon Loop Fragments Containing Ureidonucleosides," Tetrahedron Letters No. 22, pp. 1935-1936, 1977.

Anzai and Uzawa, "Cyclonucleoside Formation and Ring Cleavage in the Reaction of 2',3'-*O*-Isopropylideneadenosine with Benzoyl Chloride and Its Substituted Derivatives," *J.Org. Chem.* 49:5076-5080 (1984).

Baraldi, et al., "Synthesis and Biological Evaluation of Novel $N^6$-[4-(Substituted)sulfonamideophenylcarbamoyl]adenosine-5'-uronamides as $A_3$ Adenosine Receptor Agonists," *Journal of Medicinal Chemistry* 47:5535-5540 (2004).

Baraldi, et al., "Synthesis and Biological Activity of a New Series of $N^6$-Arylcarbamoyl, 2-(Ar)alkynyl- $N^6$-arylcarbamoyl, and $N^6$-Carboxamido Derivatives of Adenosine-5'-*N*-ethyluronamide as $A_1$ and $A_3$ Adenosine Receptor Agonists," Journal of Medicinal Chemistry 41:3174-3185 (1998).

Moffatt et al., "Nucleoside Polyphosphate . . . ", Journal of the American Chemical Society (1958), 80, 3756-61.

* cited by examiner

NON-NUCLEOTIDE COMPOSITIONS AND METHOD FOR INHIBITING PLATELET AGGREGATION

This application claims priority to U.S. provisional application No. 60/513,845 filed Oct. 21, 2003. The content of which is incorporated herein by reference in its entirety.

TECHNICAL FIELD

This invention relates to non-nucleotide compounds and methods of making and using such compounds in the prevention or treatment of diseases or conditions associated with platelet aggregation, including thrombosis, stroke and myocardial infarction in humans and other mammals, and for inhibition of platelet aggregation in blood and blood-related products.

BACKGROUND OF THE INVENTION

Hemostasis is the spontaneous process of arresting bleeding from damaged blood vessels. Upon injury, precapillary vessels contract within seconds, and thrombocytes, or blood platelets, bind to the exposed subendothelial matrix of an injured vessel by a process called platelet adhesion. Platelets also stick to each other in a phenomenon known as platelet aggregation to form stable platelet aggregates that quickly help stop or slow blood outflow from injured vessels.

An intravascular thrombus can result from pathological disturbances of hemostasis, or by the rupture of atherosclerotic plaques. Platelet adhesion and aggregation are critical events in intravascular thrombosis. Activated under conditions of high shear blood flow in diseased vessels or by the release of mediators from other circulating cells and damaged endothelial cells lining the vessel, platelets and other cells accumulate at a site of vessel injury to form a thrombus, and recruit more platelets to the developing thrombus. The thrombus can grow to sufficient size to block off arterial blood vessels. Thrombi can also form in areas of stasis or slow blood flow in veins. Venous thrombi can easily detach portions of themselves, creating emboli that travel through the circulatory system. This process can result in blockade of other vessels, such as pulmonary arteries. Blockages of this sort can result in pathological outcomes such as pulmonary embolism. Thus, arterial thrombi cause serious disease by local blockade, whereas the morbidity and mortality associated with venous thrombi arise primarily after distant blockade, or embolization. Conditions associated with pathological thrombus formation include venous thromboembolism, thrombophlebitis, deep vein thrombosis, arterial embolism, coronary and cerebral arterial thrombosis, unstable angina, myocardial infarction, stroke, transient ischemic attack, cerebral embolism, renal embolism and pulmonary embolism.

A number of converging pathways lead to platelet aggregation. Whatever the initial stimulus, the final common event is crosslinking of platelets by binding of fibrinogen to a membrane binding site, glycoprotein IIb/IIIa (GP IIb/IIIa, also known as integrin $\alpha_{IIb}\beta_3$). Antagonists of the GP IIb/IIIa receptor have been shown to produce potent anti-thrombotic effects (Ali, U.S. Pat. No. 6,037,343; Duggan, et al., U.S. Pat. No. 6,040,317). GP IIb/IIIa antagonists include function-blocking antibodies like Abciximab (ReoPro®), cyclic peptides and peptidomimetic compounds (The EPIC investigators; Califf, R. M., coordinating author, *New Engl. J. Med.* 330: 956-961 (1994); The IMPACT-II investigators, *Lancet* 349:1422-1428 (1997); The RESTORE investigators, *Circulation* 96: 1445-1453 (1997)). The clinical efficacy of some of these newer drugs, such as Abciximab, is impressive, but recent trials have found that these approaches are associated with an increased risk of major bleeding, sometimes necessitating blood transfusion (The EPIC investigators; Califf, R. M., coordinating author, *New Engl. J. Med.* 330: 956-961 (1994)). Also, administration of this class of antiplatelet agent appears to be limited to intravenous methods.

Thrombin can produce platelet aggregation independently of other pathways but substantial quantities of thrombin are unlikely to be present without prior activation of platelets by other mechanisms. Thrombin inhibitors, such as hirudin, are highly effective antithrombotic agents. However, functioning as both antiplatelet and anti-coagulant agents, thrombin inhibitors again may produce excessive bleeding (The TIMI 9a Investigators, *Circulation,* 90: 1624-1630 (1994); The GUSTO IIa Investigators, *Circulation,* 90: 1631-1637 (1994); Neuhaus, et al., *Circulation,* 90: 1638-1642 (1994)).

Various antiplatelet agents have been studied as inhibitors of thrombus formation. Some agents such as aspirin and dipyridamole have come into use as prophylactic antithrombotic agents, and others have been the subjects of clinical investigations. To date, therapeutic agents such as the disintegrins, and the thienopyridines ticlopidine (TICLID®) and clopidogrel (PLAVIX®) have been shown to have utility as platelet aggregation inhibitors, although they can produce a substantial number of side effects and have limited effectiveness in some patients. (Hass, et al., *N. Engl. J. Med.,* 321: 501-507 (1989); Weber, et al., *Am. J. Cardiol.* 66: 1461-1468 (1990); Lekstrom and Bell, *Medicine* 70: 161-177 (1991)). In particular, the use of the thienopyridines in antiplatelet therapies has been shown to increase the incidence of potentially life threatening thrombotic thrombocytopenic purpura (Bennett, et al., *N. Engl. J. Med,* 342: 1771-1777 (2000)). Aspirin, which has a beneficial effect on the inhibition of platelet aggregation (Antiplatelet Trialists' Collaboration, *Br. Med. J.* 308: 81-106 (1994); Antiplatelet Trialists' Collaboration, *Br. Med. J.* 308: 159-168 (1994)), acts by inhibiting the synthesis of prostaglandins. Its well-documented, high incidence of gastric side effects, however, limits its usefulness in many patients. In addition, aspirin resistance has been observed in some individuals (McKee, et al., *Thromb. Haemost.* 88: 711-715 (2002)).

Many studies have demonstrated that adenosine 5'-diphosphate (ADP) plays a key role in the initiation and progression of arterial thrombus formation (Bernat, et al., *Thromb. Haemostas.* 70: 812-826 (1993)); Maffrand, et al., *Thromb. Haemostas.* 59: 225-230 (1988); Herbert, et al., *Arterioscl. Thromb.* 13: 1171-1179 (1993)). ADP induces inhibition of adenylyl cyclase and modulation of intracellular signaling pathways such as activation of phosphoinositide-3 kinase (PI3K), influx and mobilization of intracellular $Ca^{+2}$, secretion, shape change, and platelet aggregation (Dangelmaier, et al. *Thromb Haemost.* 85: 341-348 (2001)). ADP-induced platelet aggregation is triggered by its binding to specific receptors expressed in the plasma membrane of the platelet. There are at least three different P2 receptors expressed in human platelets: $P2X_1$, $P2Y_1$, and $P2Y_{12}$. The $P2X_1$ receptor is a ligand-gated cation channel that is activated by ATP, resulting in a transient influx of extracellular calcium. This receptor has been implicated in the regulation of platelet shape change, and recent evidence suggests its participation in thrombus formation in small arteries under high shear forces. (Jagroop, et al., *Platelets* 14:15-20 (2003); Hechler, et al., *J. Exp. Med.* 198: 661-667 (2003)). The $P2Y_1$ receptor is a G protein-coupled receptor that is activated by ADP, and is responsible for calcium mobilization from intracellular stores, platelet shape change and initiation of aggregation. The $P2Y_{12}$ receptor, also referred to as the $P2Y_{ac}$ and $P2_T$ receptor, is a G protein-coupled receptor that is activated by ADP and is responsible for inhibition of adenylyl cyclase and activation of P13K. Activation of $P2Y_{12}$ is required for platelet secretion and stabilization of platelet aggregates (Gachet, *Thromb. Haemost.* 86: 222-232 (2001); André, et al., *J. Clin. Invest.*, 112: 398-406 (2003)).

ADP-induced platelet aggregation requires the simultaneous activation of both $P2Y_1$ and $P2Y_{12}$ receptors, and therefore, aggregation can be inhibited by blockade of either receptor. Several authors have demonstrated that ADP-induced aggregation is inhibited in a concentration-dependent manner by analogues of adenosine triphosphate (ATP). ATP, itself, is a weak and nonselective, but competitive, $P2Y_1$ and $P2Y_{12}$ receptor antagonist. Ingall, et al. (*J. Med. Chem.* 42: 213-220 (1999)) have reported that modification of the polyphosphate side chain of ATP along with substitution of the adenine moiety at the $C^2$-position, resulted in compounds that inhibited the $P2_T$ receptor (or $P2Y_{12}$ receptor). Zamecnik (U.S. Pat. No. 5,049,550) has disclosed a method for inhibiting platelet aggregation by administration of a diadenosine tetraphosphate-like compound, App(CH$_2$) ppA. Kim and Zamecnik (U.S. Pat. No. 5,681,823) have disclosed $P^1,P^4$-(dithio)-$P^2$, $P^3$-(monochloromethylene)-5',5'''-diadenosine-$P^1,P^4$-tetraphosphate as an antithrombotic agent.

Nucleotide $P2Y_{12}$ antagonists have been developed, however, there is still a need for compounds that have improved oral bioavailability and blood stability.

Thienopyridines, ticlopidine and clopidogrel react covalently with the $P2Y_{12}$ receptor and produce irreversible platelet inhibition in vivo (Quinn and Fitzgerald, *Circulation* 100: 1667-1672 (1999); Geiger, et al., *Arterioscler. Thromb. Vasc. Biol.* 19: 2007-2011 (1999); Savi, et al., *Thromb Haemost.* 84: 891-896 (2000)). Patients treated with thienopyridines usually require 2-3 days of therapy to observe significant inhibition of platelet aggregation, however, and maximal inhibition usually is observed between 4 to 7 days after initiation of treatment. Also, the platelet inhibitory effect of thienopyridines persists up to 7-10 days after the therapy is discontinued, and both ticlopidine and clopidogrel produce a significant prolongation of the bleeding time (from 1.5 to 2-fold over control). Because of the prolonged effect of thienopyridines, these drugs need to be discontinued for 7 to 10 days prior to elective surgery, leaving the patient unprotected from a possible thrombotic event during that period. Recently, the association of thienopyridine treatment with events of thrombotic thrombocytopenic purpura has been reported (Bennett, et al., *N. Engl. J. Med.* 342: 1773-1777 (2000); Bennett, et al., *Ann. Intern. Med.* 128: 541-544 (1998)).

Derivatives of 5,7-disubstituted-1,2,3-triazolol[4,5-d]pyrimidin-3-yl-cyclopentanes and -tetrahydrofurans have been disclosed as antagonists of the P2T-(or $P2Y_{12}$) receptor on platelets (Cox, et al., U.S. Pat. No. 5,747,496, and related patents; Bonnert, et al., U.S. Pat. No. 6,297,232; WO 98/28300; Brown, et al., WO 99/41254; WO 99/05144; Hardern, et al. WO 99/05142; WO 01/36438; and Guile, et al. WO 99/05143) for use in the treatment of platelet aggregation disorders.

Guile, et al. (WO 00/04021) disclose the use of triazolo [4,5-d]pyrimidine compounds in therapy. Brown, et al. (U.S. Pat. No. 6,369,064) disclose the use of Triazolo(4,5-d) pyrimidine compounds in the treatment of myocardial infarction and unstable angina. Dixon, et al. (WO 02/096428) disclose the use of 8-azapurine derivatives in combination with other antithrombotic agents for antithrombotic therapy. Springthorpe discloses AZD6140 as a potent, selective, orally active $P2Y_{12}$ receptor antagonist which is now in Phase I clinical trials (Abstracts of Papers, 225$^{th}$ ACS National Meeting, New Orleans, La.; March, 2003; MEDI-016). WO 02/016381 discloses a method of preventing or treating diseases or conditions associated with platelet aggregation using mononucleoside polyphosphates and dinucleoside polyphosphates.

There is still a need in the areas of cardiovascular and cerebrovascular therapeutics, and in blood product preparation, purification, and storage, for selective, reversible inhibitors of platelet activation, which can be used in the prevention and treatment of thrombi or other aggregation-related problems.

SUMMARY OF THE INVENTION

This invention is directed to methods of preventing or treating diseases or conditions associated with platelet aggregation or where the aggregation of platelets inhibits treatment options. This invention is directed to methods of preventing or treating thrombosis and related disorders. This invention is further directed to methods of inhibiting platelet aggregation in blood and blood products comprising platelets, such as stored blood.

The method comprises administering to a mammalian subject or to a sample comprising blood or platelet-comprising material, a composition comprising one or more non-nucleotide $P2Y_{12}$ receptor antagonist compound that effectively binds to $P2Y_{12}$ receptors on platelets, preferably in a reversible manner, and thereby causes a inhibition of the ADP-induced platelet aggregation response in blood or in a platelet-comprising material. The compounds useful for this invention are compounds of general Formula I, and/or tautomers thereof, and/or pharmaceutically-acceptable hydrates, solvates, and/or salts thereof.

The invention also provides novel compounds and pharmaceutical compositions. The compounds of Formulae I, and III-XI are useful in that they possess antagonist activity at platelet $P2Y_{12}$ receptors.

Optionally, the compounds of this invention can be used in combination with other compounds useful for the treatment of platelet aggregation disorders or diseases.

DETAILED DESCRIPTION OF THE INVENTION

This invention is directed to methods of preventing or treating diseases or conditions associated with platelet aggregation or where the aggregation of platelets inhibits treatment options. This invention is also directed to methods of preventing or treating thrombosis and related disorders. This invention provides methods of treating venous thrombosis, established peripheral arterial disease, thrombophlebitis, arterial embolism, coronary and cerebral arterial thrombosis, unstable angina, myocardial infarction, stroke, cerebral embolism, renal embolism, pulmonary embolism and other embolism- or thrombosis-related afflictions due to surgical complications, or due to platelet-aggregation complications related to the use of anesthetics during surgery.

This invention is further directed to methods of inhibiting platelet aggregation in blood and blood products comprising platelets, such as stored blood.

The method comprises administering to a subject or blood and blood products a composition comprising an effective amount of $P2Y_{12}$ receptor antagonist compound, wherein said amount is effective to bind the $P2Y_{12}$ receptors on platelets and inhibit platelet aggregation, preferably in a reversible manner. Optionally, these materials can be used in combination with other compounds useful for the treatment of platelet aggregation disorders or diseases.

The $P2Y_{12}$ receptor antagonist compounds useful for this invention include non-nucleotide compounds of general Formula I, and/or tautomers thereof, and/or pharmaceutically-acceptable hydrates, solvates, and/or salts thereof:

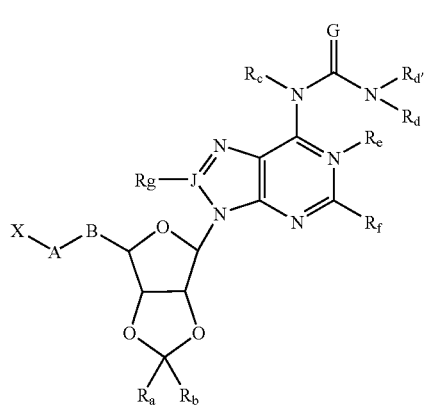

Formula I wherein $R_a$ and $R_b$ are each independently selected from the group consisting of: hydrogen, saturated or unsaturated $C_{1-8}$ alkyl, saturated or unsaturated $C_{3-7}$ cycloalkyl, aralkyl (including saturation and/or unsaturation in the alkylene portion), aryl, and saturated or unsaturated $C_{2-6}$ heterocycle; where all rings or chains optionally can bear one or more desired substituents; or $R_a$ and $R_b$ can be taken together to form a ring of 3 to 7 members, with or without substitution, and with or without heteroatoms in place of ring carbon atoms;

$R_c$=H, OR, $C_{1-8}$ alkyl, $C_{3-7}$ cycloalkyl, aralkyl, aryl, heterocycle, or L(CO)—;

R is selected from the group consisting of: H, saturated or unsaturated $C_{1-8}$ alkyl, saturated or unsaturated $C_{3-7}$ cycloalkyl, aryl, aralkyl, heteroaryl, and saturated or unsaturated $C_{2-6}$ heterocycle; where all rings or chains optionally can bear one or more desired substituents;

L is selected from the group consisting of: H, —$CF_3$, —$CF_2CF_3$, saturated or unsaturated $C_{1-8}$ alkyl, saturated or unsaturated $C_{3-7}$ cycloalkyl, saturated or unsaturated heteroaryl, aryl, aralkyl (including saturation and/or unsaturation in the alkylene portion), saturated or unsaturated $C_{2-6}$ heterocycle, $C_{1-6}$ alkoxy, aralkoxy, aryloxy, N,N-disubstituted-amino, N-substituted-amino, or unsubstituted-amino; where all rings or chains optionally can bear one or more desired substituents; or when L is N-substituted-amino, or N,N-disubstituted-amino, each substituent of said amino group of L is selected from the group consisting of: $C_{1-8}$ alkyl, $C_{3-7}$ cycloalkyl, aryl, heteroaryl, aralkyl, and $C_{2-6}$ heterocycle;

when L is N,N-disubstituted-amino, the two substituents independently selected from the group above can then be taken together to form a ring of 3 to 7 members, wherein said formed ring thereon bears the remaining features of said selected substituents before said ring formation;

G=O, S or $NR_d$ where $R_d$ is defined as below;

$R_d$ and $R_{d'}$ are independently selected from the group consisting of: H, —CN, saturated or unsaturated $C_{1-8}$ alkyl, saturated or unsaturated $C_{3-7}$ cycloalkyl, aralkyl (including saturation and/or unsaturation in the alkylene portion), aryl, heteroaryl, and saturated or unsaturated $C_{2-6}$ heterocycle;

with the proviso that no more than one cyano group can be present in any $(R_c)$—$N^6$-(G)-$NR_dR_{d'}$ unit; or $R_d$ and $R_{d'}$ groups can be taken together to form a ring of 4 to 7 members, with or without unsaturation and with or without heteroatoms in place of ring-carbon units; or $R_d$ or $R_{d'}$ and $R_c$ can be taken together to form a ring of 4 to 7 members, with or without unsaturation and with or without heteroatoms in place of ring-carbon units;

$R_e$=O or absent;

$R_f$=H, halogen, saturated or unsaturated $C_{1-8}$ alkyl, saturated or unsaturated $C_{3-7}$ cycloalkyl, aryl, aralkyl (including saturation and/or unsaturation in the alkylene portion), heteroaryl, saturated or unsaturated $C_{2-6}$ heterocycle, —OH, $C_{1-6}$ alkoxy, aryloxy, —SH, $C_{1-6}$ thioalkyl, thioaryl, —[(CO)OR], —[(CO)NRR], amino, —N-substituted amino, or N,N-disubstituted amino; wherein each said substituent on said N-substituted-amino group, or N,N-disubstituted-amino-group of $R_f$ is independently selected from the group consisting of: $C_{1-8}$ alkyl, $C_{3-7}$ cycloalkyl, aryl, aralkyl, heteroaryl, $C_{2-6}$ heterocycle, —[(CO)R] and —[(CO)—NRR]; wherein each R is independently as defined above; or when $R_f$ is —[(CO)NRR], —[NH(CO)NRR], —[N($C_{1-8}$ alkyl)(CO)NRR], —[N(aryl)(CO)NRR], or [N(aralkyl)(CO)NRR], the R groups of said —NRR unit (N,N-disubstituted-amino-group) in $R_f$ can be taken together such that a ring of 3 to 7 members is formed, with or without heteroatoms in place of the ring-carbon units;

J=N or C, with the proviso that when J=N, then $R_g$ is absent;

when J=C, $R_g$ is selected from the group consisting of: —H, halogen, saturated or unsaturated $C_{1-8}$ alkyl, saturated or unsaturated $C_{3-7}$ cycloalkyl, aralkyl, aryl, —OH, $C_{1-6}$ alkoxy, aryloxy, —SH, $C_{1-6}$ thioalkyl, thioaryl, —[(CO)OR], —[(CO)NRR], and —NRR;

wherein each R is independently as defined above; or
when $R_g$ is —[(CO)NRR] or —NRR, the R groups of said —NRR unit (N,N-disubstituted-amino-group) in $R_g$ can be taken together such that a ring of 3 to 7 members is formed, with or without heteroatoms in place of the ring-carbon units;

A and B are each independently selected from the group consisting of: —$C_{1-3}$ alkylene-, —$CF_2$—, and —(CO)—; wherein each said —$C_{1-3}$ alkylene-unit of A and B independently can be saturated or unsaturated, and each carbon of a —$C_{1-3}$ alkylene-unit of B independently can be substituted with 0 to 2 fluorine groups, 0 to 1 methyl groups, 0 to 2—[(CO)OR] groups, and 0 to 1 —(OR) groups; or B can be absent;

in addition, one substitution of a heteroatom-containing-unit selected from the group: —O—, —S—, —NR—, —[NR(CO)]— or —N[(CO)L]-, where each R and L is independently as defined above, optionally can be made for any one-carbon-unit within either or both of said $C_{1-3}$ alkylene units of A and B, provided that fewer than three said heteroatom-containing-unit for -one-carbon-unit substitutions on the -A-B— chain are made, no —S—S—, or —O—O— bonds are formed in the X-A-B— chain by said substitution or substitutions of a heteroatom-containing-unit for a -one-carbon-unit on the -A-B— chain, and no said heteroatom substitution is made such that the said replacement heteroatom connects directly to the tetrahydrofuran ring shown in Formula I;

X=H, —OR, —SR, —S(O)L, —S($O_2$)L, —$SO_3H$, —S($O_2$)NRR, —S($O_2$)NR(CO)L, —NRR, —NR(CO)L, —N[(CO)L]$_2$, —NR($SO_2$)L, —NR(CO)NR($SO_2$)L, —NR($SO_2$)NRR, or —NR($SO_2$)NR(CO)L; wherein each R and L is independently as defined above;

wherein the R groups of a —NRR unit (N,N-disubstituted-amino-group) in X optionally can be taken together such that a ring of 3 to 7 members is formed, with or without heteroatoms in place of the ring-carbon units;

with the proviso that when X=H, then at least one of $R_a$ or $R_b$ must be H; and with the further proviso that no compound in Formula I contains: a halogen-group, hydroxy-group, sulfhydryl-group, or amino-group (—$NH_2$, N-substituted-amino, or N,N-disubstituted-amino) attached to an $sp^3$-hybridized-carbon atom that is bonded directly to a heteroatom selected from the group consisting of O, S, and N, as compounds in this class (e.g., —[C(OH)(SR)]—, —[CCl(NRR)]—, etc.), are, in general, of lower chemical stability; the first exception to this proviso is: compounds in which the said $sp^3$-hybridized-carbon atom is bonded directly to: 1) a sulfur atom which is part of a —[S(O)]-group (sulfinyl group), or a —[S($O_2$)]-group (sulfonyl group) and also to: 2) one or more halogen atoms (an example of a moiety having this arrangement is a trifluoromethanesulfonyl group); the second and final exception to this proviso is the C-1' position of the furanose of compounds of Formula I where the $sp^3$-hybridized-carbon atom at the 1'-position is attached to: 1) the oxygen atom of the furanose ring and to: 2) the nitrogen atom of the adenine or 8-azaadenine moiety;

or

X is a group as provided in Formula II:

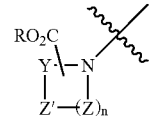

Formula II wherein:

n=1 to 4, inclusive;

Y, Z and Z' are independently selected from —$CRR_f$—, —NR—, —[N(CO)L]-, —O— and —S—; or the said —Y—Z'-unit, taken together, can be selected to be a —N=N— unit or a —CR=$CR_f$— unit;

or any-$(Z)_2$-unit or subunit of —$(Z)_n$ can be selected to be a —CR=$CR_f$— unit;

and with the provisos that the ring shown in Formula II contains no more than three heteroatoms, and that the shown pendant $CO_2R$ unit in Formula II is a substituent on the ring described in Formula II, and that the ring of Formula II contains no halogen-group, hydroxy-group, sulfhydryl-group, or amino-group (—$NH_2$, N-substituted-amino, or N,N-disubstituted-amino) attached to an $sp^3$-hybridized-carbon atom that is bonded directly to a heteroatom selected from the group consisting of O, S, and N, as such types of compounds are unstable in many cases.

Preferably, the furanosyl moiety in Formula I has the 2'- and 3'-oxygen-groups in a cis-orientation relative to one another on the furanose ring. Further, a furanosyl moiety which supports a 2',3'-acetal or -ketal group is, preferably, derived from ribose; other furanose derivatives can be used, however. A preferred stereochemical embodiment of this invention includes, but is not limited to (D)-ribose-(2',3'-acetal or -ketal) compounds of Formula I, such as found in acetals derived from (−)-adenosine.

In one embodiment of the method, the compound of Formula I is selected from the group consisting of: 6-[6-(3-Cyclopropyl-ureido)-purin-9-yl]-2-styryl-tetrahydro-furo[3,4-d][1,3]dioxole-4-carboxylic acid; 6-[6-(3-Ethyl-ureido)-purin-9-yl]-2-styryl-tetrahydro-furo[3,4-d][1,3]dioxole-4-carboxylic acid; 6-[6-(3-Butyl-ureido)-purin-9-yl]-2-styryl-tetrahydro-furo[3,4-d][1,3]dioxole-4-carboxylic acid; 6-[6-(3-Propyl-ureido)-purin-9-yl]-2-styryl-tetrahydro-furo[3,4-d][1,3]dioxole-4-carboxylic acid; 2-[({6-[6-(3-Ethyl-ureido) -purin-9-yl]-2-styryl-tetrahydro-furo[3,4-d][1,3]dioxol-4-ylmethyl}-amino)-methyl]-cyclopropanecarboxylic acid; 3-{6-[6-(3-Ethyl-ureido)-purin-9-yl]-2-styryl-tetrahydro-furo[3,4-d][1,3]dioxol-4-ylmethyl}-3H-[1,2,3]triazole-4-carboxylic acid; 3-{6-[6-(3-Ethyl-ureido)-purin-9-yl]-2-styryl-tetrahydro-furo[3,4-d][1,3]dioxol-4-yl}-propionic acid; {6-[6-(3-Ethyl-ureido)-purin-9-yl]-2-styryl-tetrahydro-furo[3,4-d][1,3]dioxol-4-yl}-acetic acid; 1-{6-[6-(3-Cyclopentyl-ureido)-purin-9-yl]-2-phenyl-tetrahydro-furo[3,4-d][1,3]dioxole-4-carbonyl}-pyrrolidine-2-carboxylic acid; {6-[6-(3-Ethyl-ureido)-purin-9-yl]-2-phenyl-tetrahydro-furo[3,4-d][1,3]dioxol-4-yl}-acetic acid; {6-[6-(3-Cyclopentyl-ureido)-purin-9-yl]-2- phenyl-tetrahydro-furo[3,4-d][1,3]dioxol-4-yl}-acetic acid; 3-{6-[6-(3-Ethyl-ureido)-purin-9-yl]-2-phenyl-tetrahydro-furo[3,4-d][1,3]dioxol-4-yl}-propionic acid; 3-{6-[6-(3-Ethyl-ureido)-purin-9-yl]-2-styryl-tetrahydro-furo[3,4-d][1,3]dioxol-4-ylmethoxymethyl}-benzoic acid; ({6-[6-(3-Ethyl-ureido)-purin-9-yl]-2-styryl-tetrahydro-furo[3,4-d][1,3]dioxol-4-ylmethyl}-amino)-acetic acid; 1-Ethyl-3-[9-(6-hydroxymethyl-2-styryl-tetrahydro-furo[3,4-d][1,3]dioxol-4-yl)-8-iodo-9H-purin-6-yl]-urea; 1-Ethyl-3-{9-[6-(2-hydroxy-ethoxymethyl)-2-styryl-tetrahydro-furo[3,4-d][1,3]dioxol-4-yl]-8-iodo-9H-purin-6-yl}-urea; 1-Ethyl-3-{9-[6-(2-hydroxy-ethyl)-2-styryl-tetrahydro-furo[3,4-d][1,3]dioxol-4-yl]-8-iodo-9H-purin-6-yl}-urea; 2-{6-[6-(3-Ethyl-ureido)-purin-9-yl]-2-styryl-tetrahydro-furo[3,4-d][1,3]dioxol-4-ylmethoxy}-nicotinic acid; 5-{6-[6-(3-Ethyl-ureido)-purin-9-yl]-2-styryl-tetrahydro-furo[3,4-d][1,3]dioxol-4-ylmethoxy}-pentanoic acid; 1-Ethyl-3-{9-[6-(2-hydroxy-propane-1-sulfonylmethyl)-2-styryl-tetrahydro-furo[3,4-d][1,3]dioxol-4-yl]-9H-purin-6-yl}-urea; 1-Ethyl-3-{9-[6-(2-methanesulfonylmethyl-pyrrolidine-1-carbonyl)-2-styryl-tetrahydro-furo[3,4-d][1,3]dioxol-4-yl]-9H-purin-6-yl}-urea; 1-Ethyl-3-{9-[6-(2-methanesulfonylmethyl-pyrrolidine-1-carbonyl)-2-phenyl-tetrahydro-furo[3,4-d][1,3]dioxol-4-yl]-9H-purin-6-yl}-urea; 1-Cyclopentyl-3-{9-[6-(2-methanesulfonylmethyl-pyrrolidine-1-carbonyl)-2-phenyl-tetrahydro-furo[3,4-d][1,3]dioxol-4-yl]-9H-purin-6-yl}-urea; 6-[6-(3-Ethyl-ureido)-8-iodo-purin-9-yl]-2-styryl-tetrahydro-furo[3,4-d][1,3]dioxole-4-carboxylic acid; 3-{6-[6-(3-Ethyl-ureido)-purin-9-yl]-2-styryl-tetrahydro-furo[3,4-d][1,3]dioxol-4-yl}-2-hydroxy-propionic acid; and 3-{6-[6-(3-Ethyl-ureido)-purin-9-yl]-2-styryl-tetrahydro-furo[3,4-d][1,3]dioxol-4-yl}-2-oxo-propionic acid; or a pharmaceutically-acceptable salt, -hydrate, or -solvate thereof.

A particularly useful embodiment is where X in Formula II has a —CO$_2$H group on the ring.

In another embodiment, the compound is selected from the group consisting of: 3-{6-[6-(3-Ethyl-1-phenyl-ureido)-purin-9-yl]-2,2-dimethyl-tetrahydro-furo[3,4-d][1,3]dioxol-4-ylmethoxy}-isoxazole-5-carboxylic acid; 3-(6-{6-[3-Ethyl-1-(5-methyl-furan-2-ylmethyl)-ureido]-purin-9-yl}-2,2-dimethyl-tetrahydro-furo[3,4-d][1,3]dioxol-4-ylmethoxy)-isoxazole-5-carboxylic acid; 3-{2,2-Dimethyl-6-[6-(3-phenyl-ureido)-purin-9-yl]-tetrahydro-furo[3,4-d][1,3]dioxol-4-ylmethoxy}-isoxazole-5-carboxylic acid; 3-{2,2-Dimethyl-6-[6-(3-phenyl-1-propyl-ureido)-purin-9-yl]-tetrahydro-furo[3,4-d][1,3]dioxol-4-ylmethoxy}-isoxazole-5-carboxylic acid; 5-Amino-2-{2,2-dimethyl-6-[6-(3-phenyl--ureido)-purin-9-yl]-tetrahydro-furo[3,4-d][1,3]dioxol-4-ylmethoxy}-N-hydroxy-benzamide; 6-{2,2-Dimethyl-6-[6-(3-phenyl-ureido)-purin-9-yl]-tetrahydro-furo[3,4-d][1,3]dioxol-4-ylmethoxy}-nicotinamide; 1-{9-[6-(3-Hydroxy-pyridin-2-yloxymethyl)-2,2-dimethyl-tetrahydro-furo[3,4-d][1,3]dioxol-4-yl]-9H-purin-6-yl}-3-phenyl-urea;3-({2,2-Dimethyl-6-[6-(3-phenyl-ureido)-purin-9-yl]-tetrahydro-furo[3,4-d][1,3]dioxole-4-carbonyl}-amino)-benzoic acid;2-({2-Benzyl-6-[6-(3-phenyl-ureido)-purin-9-yl]-tetrahydro-furo[3,4-d][1,3]dioxole-4-carbonyl}-amino)-3-hydroxy-propionic acid; N-{2-Benzyl-6-[6-(3-phenyl-ureido)-purin-9-yl]-tetrahydro-furo[3,4-d][1,3]dioxole-4-carbonyl}--methanesulfonamide; 1-[9-(2-Benzyl-6-ureidomethyl-tetrahydro-furo[3,4-d][1,3]dioxol-4-yl)-9H-purin-6-yl]-3-phenyl-urea methylsulfonamide; 3-{2,2-Dimethyl-6-[6-(3-phenyl-ureido)-purin-9-yl]-tetrahydro-furo[3,4-d][1,3]dioxol-4-yl}-acrylic acid methyl ester; 3-{2,2-Dimethyl-6-[6-(3-phenyl-ureido)-purin-9-yl]-tetrahydro-furo[3,4-d][1,3]dioxol-4-yl}-propionic acid methyl ester; 3-{2,2-Dimethyl-6-[6-(3-phenyl-ureido)-purin-9-yl]-tetrahydro-furo[3,4-d][1,3]dioxol-4-yl}-propionic acid; and 3-(3-{2,2-Dimethyl-6-[6-(3-phenyl-ureido)-purin-9-yl]-tetrahydro-furo[3,4-d][1,3]dioxol-4-yl}-propionylamino)-benzoic acid; or a pharmaceutically-acceptable salt, -hydrate, or -solvate thereof.

In another embodiment of the method, $R_b$ of Formula I is selected from the group consisting of: hydrogen, saturated or unsaturated $C_{2-8}$ alkyl, saturated or unsaturated $C_{3-7}$ cycloalkyl, aralkyl (including saturation and/or unsaturation in the alkyl portion), aryl, and $C_{2-6}$ heterocycle; where all rings or chains optionally can bear one or more desired substituents.

In another embodiment of the method, X of Formula I is selected from the group consisting of: —OR, —SR, —NRR, —NR(CO)L, —NR(SO$_2$)L, —NR(CO)NR(SO$_2$)L, —NR(SO$_2$)NR(CO)L, and a moiety as provided in Formula II; Y, Z and Z' are independently selected from —CRR$_f$—, —O— and —S—; or the said —Y—Z'—, —(Z)$_2$—, —(Z)$_3$—, and —(Z)$_4$-units are selected from the respective said —Y—Z'-units and —(Z)$_n$-units as provided in Formula II.

For example, the compound is one of Formula III:

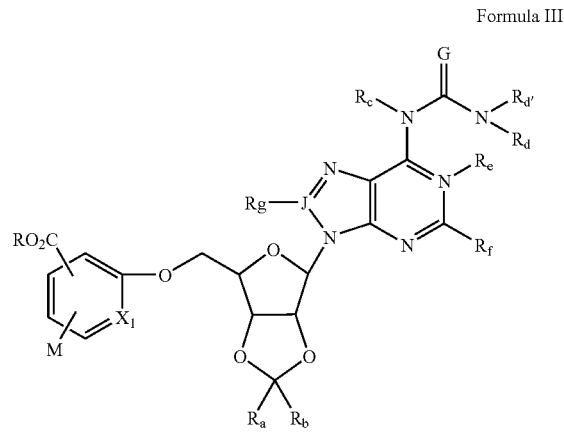

Formula III wherein $R_a$, $R_b$, $R_c$, R, L, G, $R_d$, $R_d'$, Re, $R_f$, J, and $R_g$ are as defined in Formula I;

X$_1$ is selected from the group consisting of: N (nitrogen) and C-M; and

M is independently selected from the group consisting of: —H, halogen, —CF$_3$, saturated or unsaturated $C_{1-8}$ alkyl, saturated or unsaturated $C_{3-7}$ cycloalkyl, aryl, aralkyl (including saturation and/or unsaturation in the alkylene portion), heteroaryl, saturated or unsaturated $C_{2-6}$ heterocycle, —OH, saturated or unsaturated $C_{1-6}$ alkoxy, aralkoxy, aryloxy, —SH, $C_{1-6}$ thioalkyl, thioaryl, —[(CO)OR], —[(CO)NRR], amino, —N-substituted amino, and N,N-disubstituted amino; wherein each said substituent on said amino of M is independently selected from the group consisting of: $C_{1-8}$ alkyl, $C_{3-7}$ cycloalkyl, aryl, aralkyl, heteroaryl, $C_{2-6}$ heterocycle, —[(CO)R], —[(CO)

O-(C$_{1-8}$ alkyl)], and —[(CO)—NRR]; and when M is —[(CO)NRR], —[NH(CO)NRR], —[N(C$_{1-8}$ alkyl)(CO)NRR], —[N(aryl)(CO)NRR], or —[N(aralkyl)(CO)NRR], the R groups of any said —NRR unit (N,N-disubstituted-amino group) in M can be taken together such that a ring of 3 to 7 members is formed, with or without heteroatoms in place of the ring-carbon units; or a tautomer, or a pharmaceutically-acceptable salt, -hydrate, or -solvate thereof.

A particularly useful group of compounds are those of Formula III where the R=H.

Examples of Formula III compounds are 5-Amino-2-{2,2-dimethyl-6-[6-(3 -phenyl-ureido)-purin-9-yl]-tetrahydro-furo[3,4-d][1,3]dioxol-4-ylmethoxy}-benzoic acid; 4-{2,2-Dimethyl-6-[6-(3-phenyl-ureido)-purin-9-yl]-tetrahydro-furo[3,4-d][1,3]dioxol-4-ylmethoxy}-isophthalic acid; 4-{2,2-Dimethyl-6-[6-(3-phenyl-ureido)-purin-9-yl]-tetrahydro-furo[3,4-d][1,3]dioxol-4-ylmethoxy}-benzoic acid; 6-{2,2-Dimethyl-6-[6-(3-phenyl-ureido)-purin-9-yl]-tetrahydro-furo[3,4-d][1,3]dioxol-4-ylmethoxy}-nicotinic acid; 5-Chloro-6-{2,2-dimethyl-6-[6-(3-phenyl-ureido)-purin-9-yl]-tetrahydro-furo[3,4-d][1,3]dioxol-4-ylmethoxy}-nicotinic acid; 2-{2,2-Dimethyl-6-[6-(3-phenyl-ureido)-purin-9-yl]-tetrahydro-furo[3,4-d][1,3]dioxol-4-ylmethoxy}-nicotinic acid; 6-Chloro-2-{2,2 -dimethyl-6-[6-(3-phenyl-ureido)-purin-9-yl]-tetrahydro-furo[3,4-d][1,3]dioxol-4-ylmethoxy}-5-fluoro-nicotinic acid; 6-Chloro-2-{2,2-dimethyl-6-[6-(3-phenyl-ureido)-purin-9-yl]-tetrahydro-furo[3,4-d][1,3]dioxol-4-ylmethoxy}-5-fluoro-nicotinic acid; 2-[6-[6-(3-Phenyl-ureido)-purin-9-yl]-2-(2-trifluoromethyl-phenyl)-tetrahydro-furo[3,4-d][1,3]dioxol-4-yl-methoxy]-nicotinic acid; 2-{2-Phenyl-6-[6-(3-phenyl-ureido)-purin-9-yl]-tetrahydro-furo[3,4-d][1,3]dioxol-4-ylmethoxy}-nicotinic acid; 2-{2-Biphenyl-3-yl-6-[6-(3-phenyl-ureido)-purin-9-yl]-tetrahydro-furo[3,4-d][1,3] dioxol-4-ylmethoxy}-nicotinic acid; 2-{2-Naphthalen-2-yl-6-[6-(3-phenyl-ureido)-purin-9-yl]-tetrahydro-furo[3,4-d][1,3]dioxol-4-ylmethoxy}-nicotinic acid; 2-{2-Benzo[b]thiophen-3-yl-6-[6-(3-phenyl-ureido)-purin-9-yl]-tetrahydro-furo[3,4-d][1,3]dioxol-4-ylmethoxy}-nicotinic acid; 2-{6-[6-(3-Hexyl-ureido)-purin-9-yl]-2-phenyl-tetrahydro-furo[3,4-d][1,3]dioxol-4-ylmethoxy}-nicotinic acid; 2-{2,2-Dimethyl-6-[6-(3-phenyl-ureido)-purin-9-yl]-tetrahydro-furo[3,4-d][1,3]dioxo-spiroindan-4-ylmethoxy}-nicotinic acid; 2-{6-[6-(3-Ethyl-ureido)-purin-9-yl]-2-phenethyl-tetrahydro-furo[3,4-d][1,3]dioxol-4-ylmethoxy}-nicotinic acid; 2-{6-[6-(3-Ethyl-ureido)-purin-9-yl]-2-phenylethynyl-tetrahydro-furo[3,4-d][1,3]dioxol-4-ylmethoxy}-nicotinic acid; 2-{6-[6-(3-Ethyl-ureido)-purin-9-yl]-2-phenyl-tetrahydro-furo[3,4-d][1,3]dioxol-4-ylmethoxy}-nicotinic acid; 2-{2-(2-Bromo-phenyl)-6-[6-(3-ethyl-ureido)-purin-9-yl]-tetrahydro-furo[3,4-d][1,3]dioxol-4-ylmethoxy}-nicotinic acid; 2-{6-[6-(3-Cyclopentyl-ureido)-purin-9-yl]-2-phenethyl-tetrahydro-furo[3,4-d][1,3]dioxol-4-ylmethoxy}-nicotinic acid; 2-{6-[6-(3-Cyclopentyl-ureido)-purin-9-yl]-2,2-(3,4-Dihydro-1H-naphthalen)-tetrahydro-furo[3,4-d][1,3]dioxol-4-ylmethoxy}-nicotinic acid; 2-{6-[6-(3-Cyclopentyl-ureido)-purin-9-yl]-2-p-tolyl-tetrahydro-furo[3,4-d][1,3]dioxol-4-ylmethoxy}-nicotinic acid; 2-{2-Biphenyl-4-yl-6-[6-(3-hexyl-ureido)-purin-9-yl]-tetrahydro-furo[3,4-d][1,3]dioxol-4-ylmethoxy}-nicotinic acid; 2-{2-(4-Acetylamino-phenyl)-6-[6-(3-cyclopentyl-ureido)-purin-9-yl]-tetrahydro-furo[3,4-d][1,3]dioxol-4-ylmethoxy}-nicotinic acid; and 2-{2-tert-Butyl-6-[6-(3-phenyl-ureido-purin-9-yl]-tetrahydro-furo[3,4-d][1,3]dioxol-4-ylmethoxy}-nicotinic acid; or a pharmaceutically-acceptable salt, -hydrate, or -solvate thereof.

In yet another embodiment of the method, the compound is a compound of Formula IV:

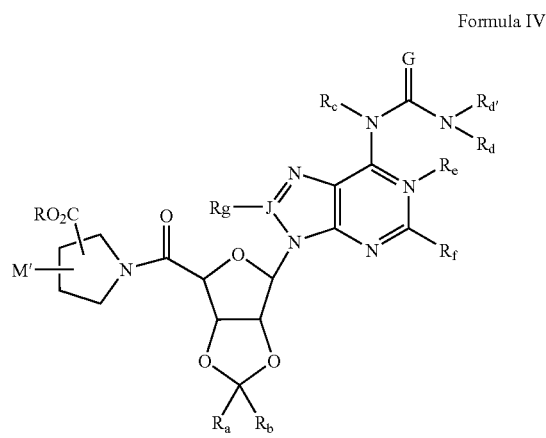

Formula IV wherein $R_a$, $R_b$, $R_c$, R, L, G, $R_d$, $R_{d'}$, $R_e$, $R_f$, J, and $R_g$ are as defined in Formula I;

M' is as defined for M;

the M' and —CO$_2$R groups are independently and optionally attached to any carbon of the pyrrolidine ring; and M' is not a halogen, hydroxy, sulfhydryl, or amino group when M' is attached to a carbon that is bonded to the pyrollidine nitrogen atom (alpha position); or a tautomer, or a pharmaceutically-acceptable salt, -hydrate, or -solvate thereof.

A particularly useful group of compounds are those of Formula IV where R=H.

Examples of Formula IV compounds are 1-{2-Phenyl-6-[6-(3-phenyl-ureido)-purin-9-yl]-tetrahydro-furo[3,4-d][1,3]dioxole-4-carbonyl}-pyrrolidine-2-carboxylic acid; 1-{2-Phenyl-6-[6-(3-phenyl-ureido)-purin-9-yl]-tetrahydro-furo[3,4-d][1,3]dioxole-4-carbonyl}-pyrrolidine-2-carboxylic acid; 1-{2-Benzyl-6-[6-(3-ethyl-ureido)-purin-9-yl]-tetrahydro-furo[3,4-d][1,3]dioxole-4-carbonyl}-pyrrolidine-2-carboxylic acid; 1-(2-Phenyl-6-{6-[3-(2-phenyl-cyclopropyl)-ureido]-purin-9-yl}-tetrahydro-furo[3,4-d][1,3]dioxole-4-carbonyl)-pyrrolidine-2-carboxylic acid; 1-{6-[6-(3-Benzyl-ureido)-purin-9-yl]-2-phenyl-tetrahydro-furo[3,4-d][1,3]dioxole-4-carbonyl}-pyrrolidine-2-carboxylic acid; 1-{2-Benzo[b]thiophen-3-yl-6-[6-(3-hexyl-ureido)-purin-9-yl]-tetrahydro-furo[3,4-d][1,3]dioxole-4-carbonyl}-pyrrolidine-2-carboxylic acid; 1-{2-Benzyl-6-[6-(3-hexyl-ureido)-purin-9-yl]-tetrahydro-furo[3,4-d][1,3]dioxole-4-carbonyl}-pyrrolidine-2-carboxylic acid; 1-{6-[6-(3-Ethylureido)-purin-9-yl]-2-naphthalen-2-yl-tetrahydro-furo[3,4-d][1,3]dioxole-4-carbonyl}-pyrrolidine-2-carboxylic acid; 1-{6-[6-(3-Hexyl-ureido)-purin-9-yl]-2-phenyl-tetrahydro-furo[3,4-d][1,3]dioxole-4-carbonyl}-pyrrolidine-2-carboxylic acid; 1-{6-[6-(3-Cyclopentyl-ureido)-purin-9-yl]-2-phenyl-tetrahydro-furo[3,4-d][1,3]dioxole-4-carbonyl}-pyrrolidine-2-carboxylic acid; and 1-(3-{2,2-Dimethyl-6-[6-(3-phenyl-ureido)-purin-9-yl]-tetrahydro-furo[3,4-d][1,3]dioxol-4-yl}-propionyl)-pyrrolidine-2-carboxylic acid; or a pharmaceutically-acceptable salt, -hydrate, or -solvate thereof.

Other groups of compounds useful for the method are included under Formulas V-XI, or pharmaceutically acceptable salts, solvates, or hydrates thereof; in which R, $R_a$, $R_b$, J and $R_g$, are defined as for Formula I, and n is defined as for Formula II.

Formula V

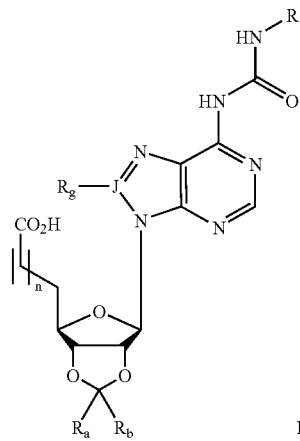

Formula VI

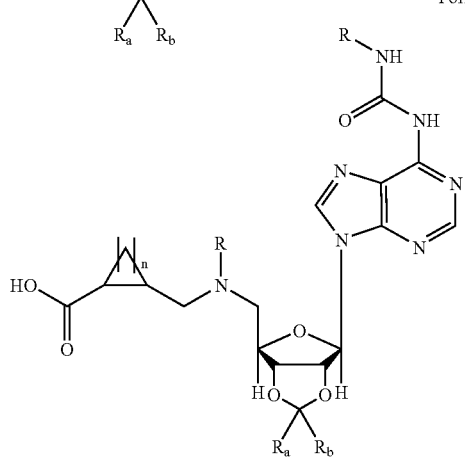

Formula VII

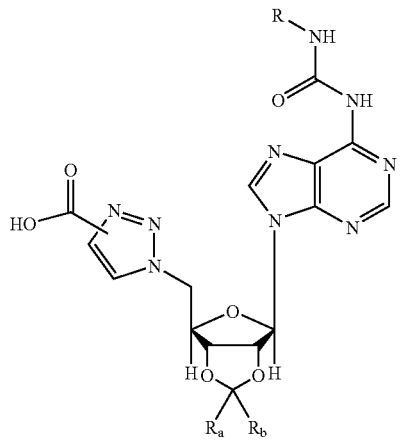

Formula VIII

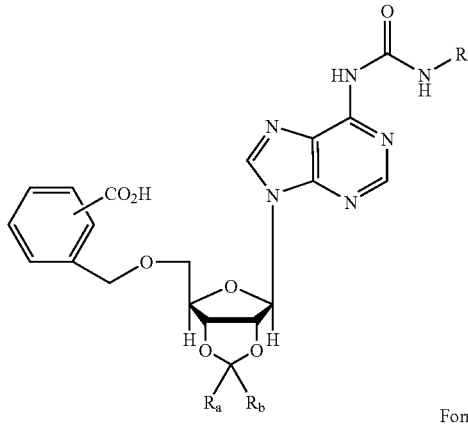

Formula IX

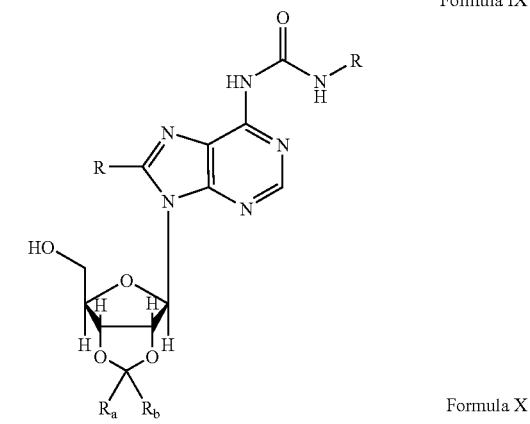

Formula X

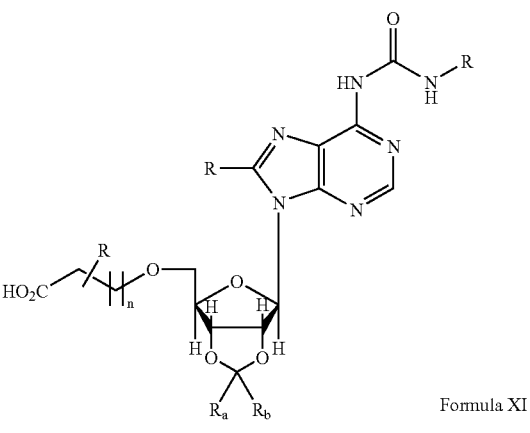

Formula XI

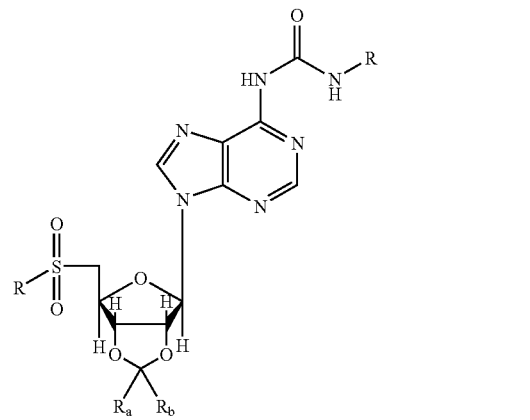

Novel Compositions

The present invention also provides novel compounds of Formulas I, III, IV, V, VI, VII, VIII, IV, X, or XI, respectively, with the further provisos that for compounds of Formula I:

(a) when $R_a$=Me, Re=nothing, $R_f$=H, I or Cl, $R_g$=H, J=C, and the unit —($R_c$)N—(CG)-$NR_dR_d$'=—HN—(CO)—NH-(aryl), —HN—(CO)—NH-(heteroaryl), —HN—(CO)—NH-(n-octyl), or —HN—(CO)—NH-(t-butyl), then $R_b$ is not equal to Me; or (b) when $R_a$=$R_b$=Me, $R_e$=nothing, $R_f$=$R_g$=H, J=C, and the unit $R_c$—N—(CG)-$NR_dR_d$'=(R')—N—(CO)—N(R")(R'''), wherein R' is H, alkyl, substituted alkyl, heteroaryl-NH—(CG')-, or aryl-NH—(CG')-, G' is selected from the group consisting of: O, NR and S; R" is H, alkyl, substituted alkyl, or aryl; and R''' is heteroaryl, aralkyl, or aryl, then the unit X-A-B— is not R—NH—(CO)—, unless said R—NH—(CO)— contains at least one —$CO_2$H group as a substituent on a ring or chain of said R; or (c) when the unit X-A-B—=H(CO)—, RO(CO)—, $ROCH_2$—, $RSCH_2$—, $RRNCH_2$— then one of $R_a$ or $R_b$ must be H, and the other $R_b$ or $R_a$ is not H, Ph, Me or Et.

The further proviso for compounds of Formula V is: wherein at least one of Ra and Rb is not methyl.

A desired substituent on a chain or ring (in place of a hydrogen at a position) is one selected from the given alkyl, aryl, halogen, aralkyl, carboxy, alkoxycarbonyl, hydroxyl, acyloxy, alkoxy, aryloxy or aralkoxy classes or from other classes, which provides a compound with good-to-excellent $P2Y_{12}$ receptor-binding properties, but which does not yield a compound with undesirable properties like chemical instability in a formulation, or one with levels of toxicity that are not well-tolerated by a treated mammal, or especially, not well-tolerated by a human.

Exemplary compounds for the present invention are shown in Table 1.

TABLE 1

Exemplary Compounds.

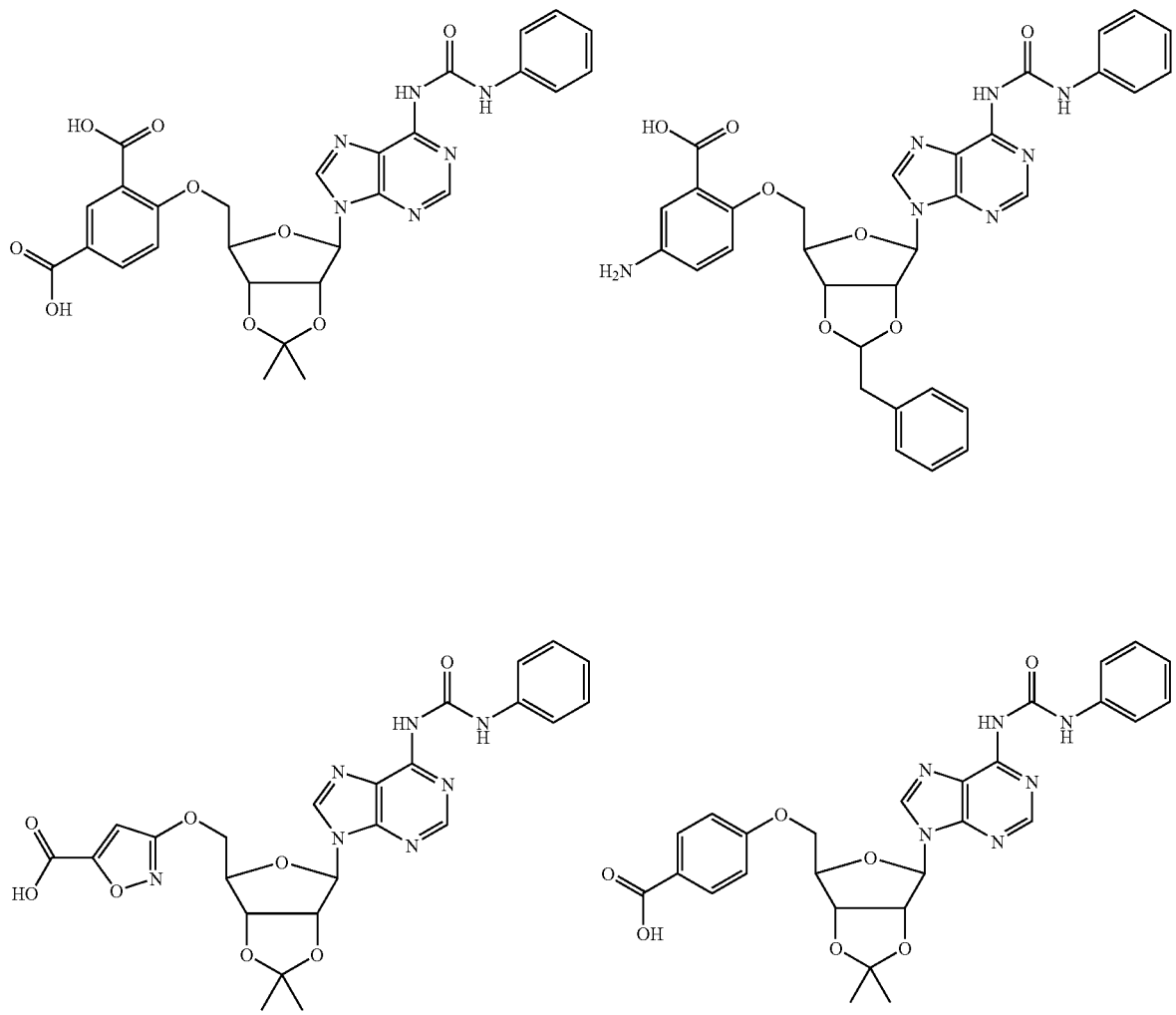

TABLE 1-continued
Exemplary Compounds.
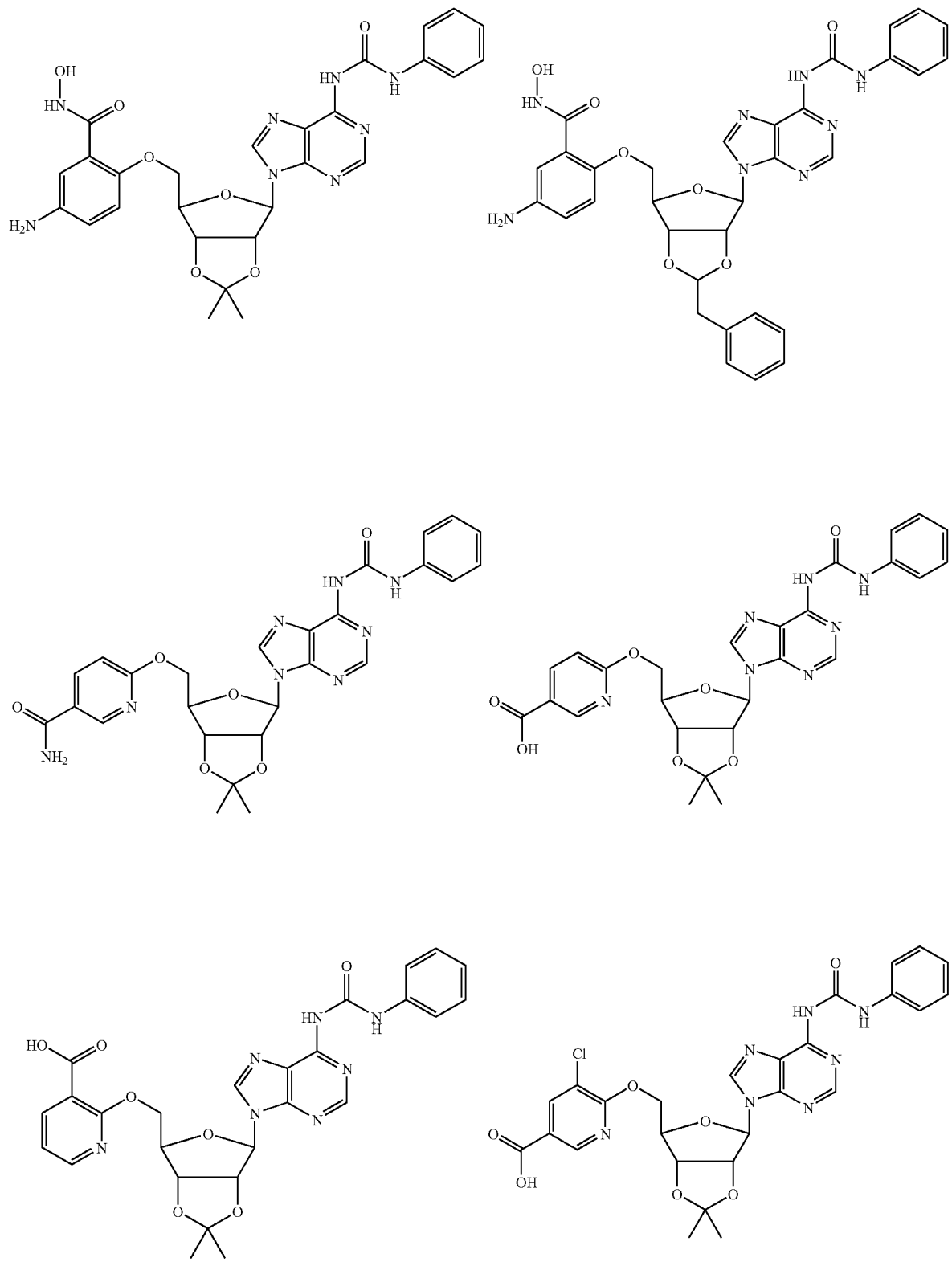

TABLE 1-continued
Exemplary Compounds.
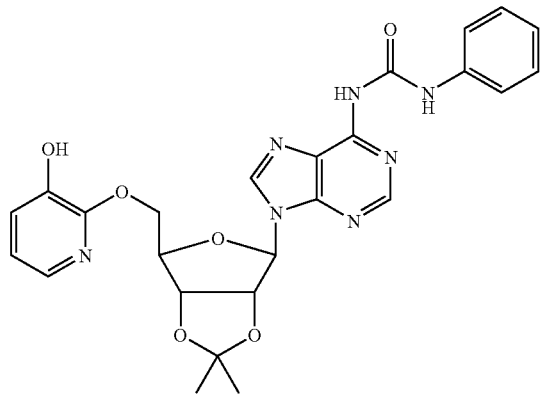 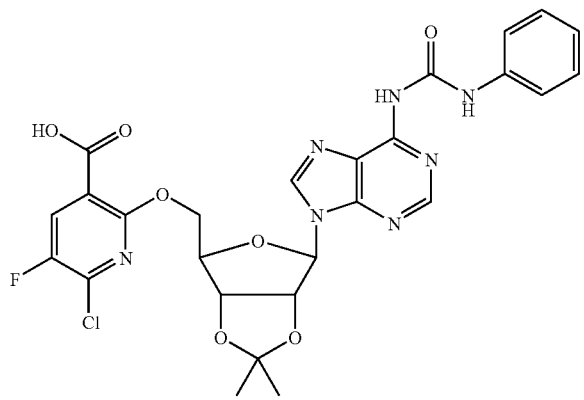
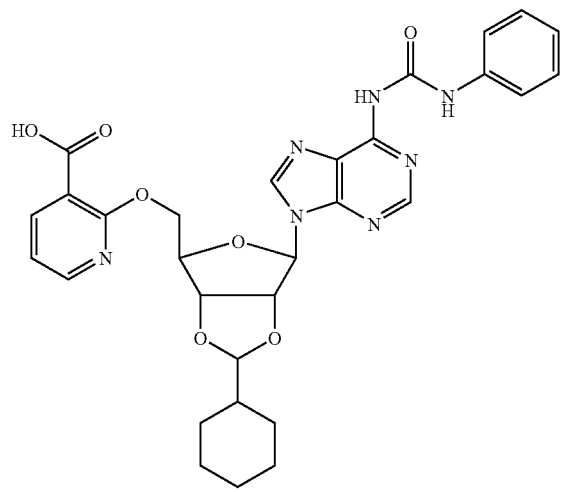 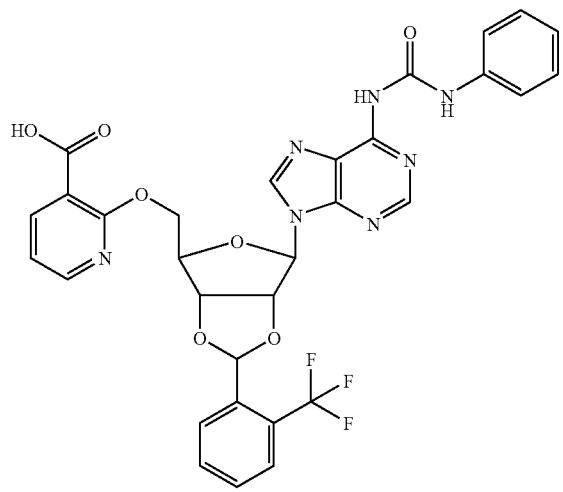
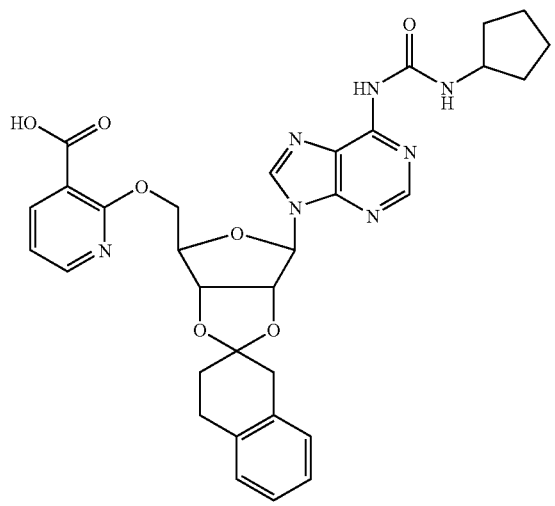 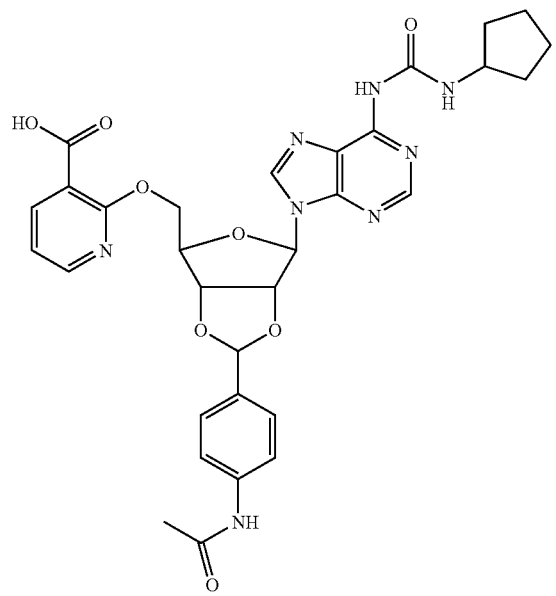

TABLE 1-continued
Exemplary Compounds.
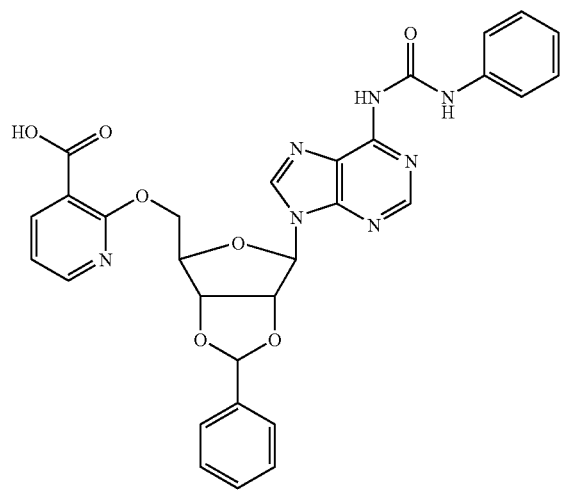
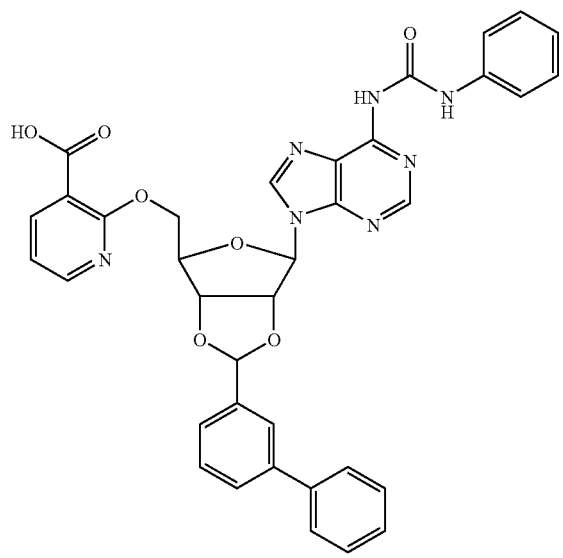
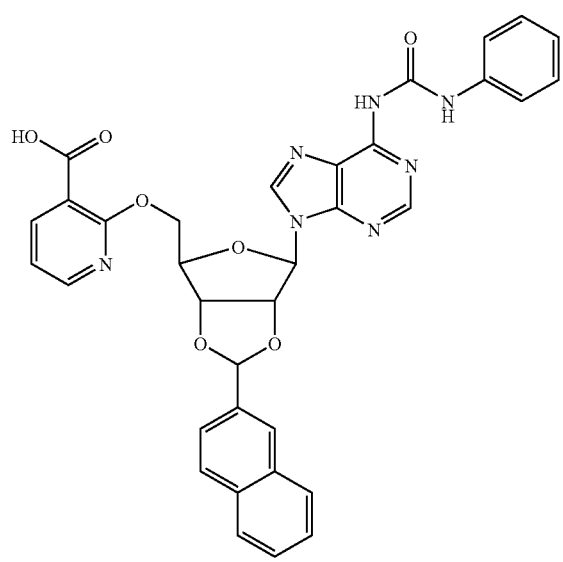
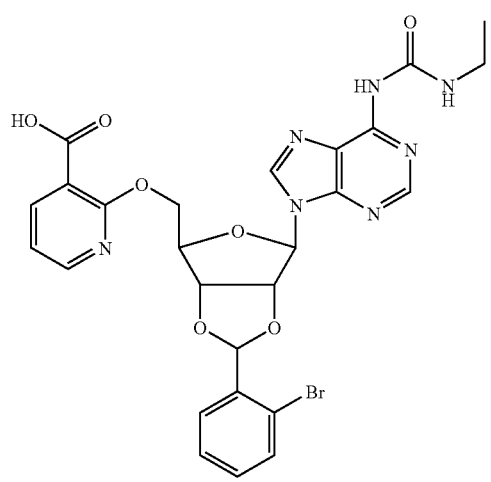

TABLE 1-continued
Exemplary Compounds.
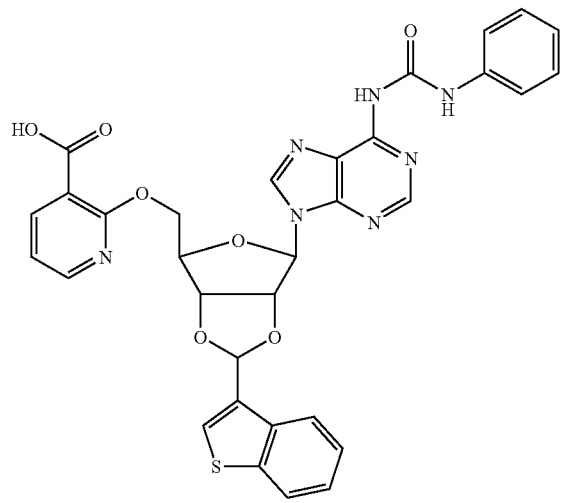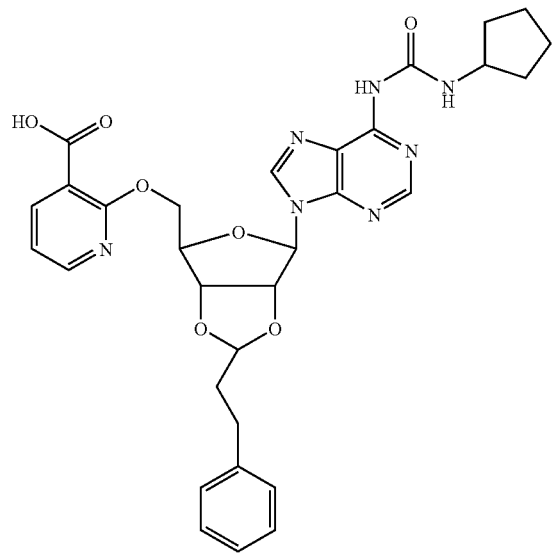
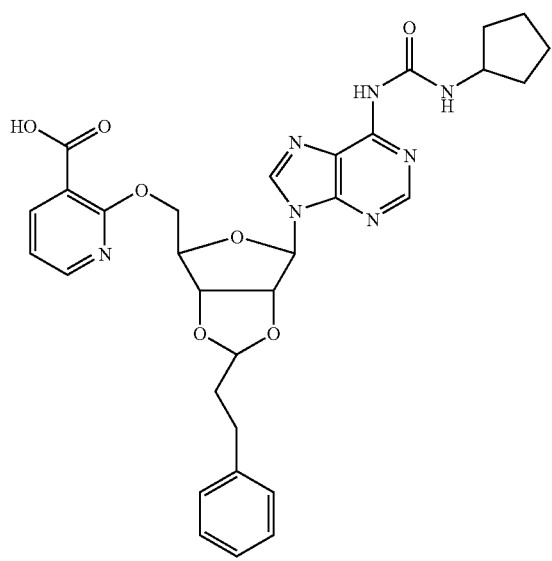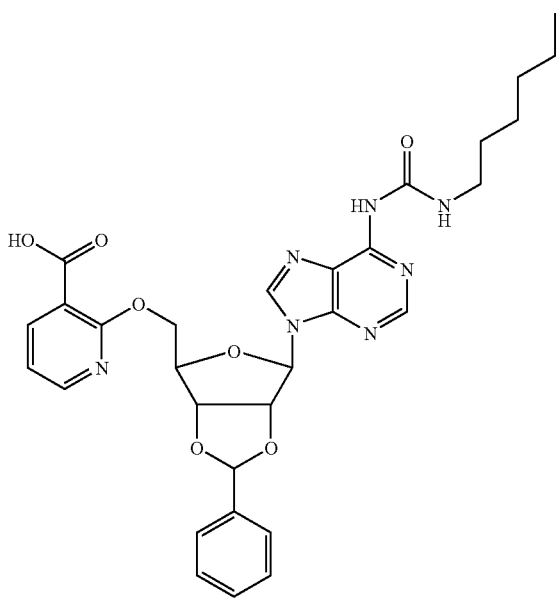

TABLE 1-continued
Exemplary Compounds.
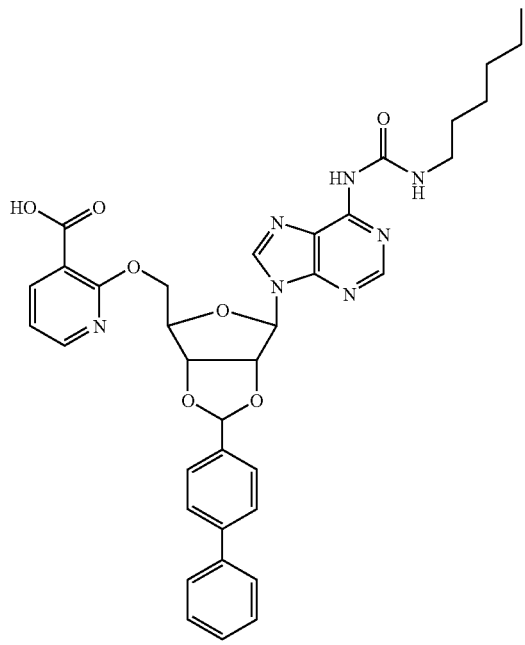
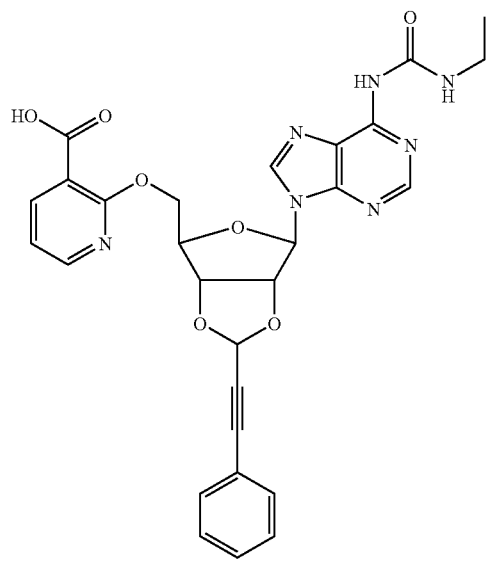
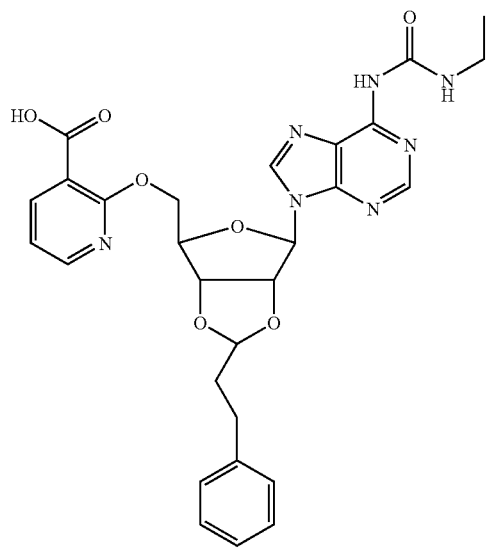
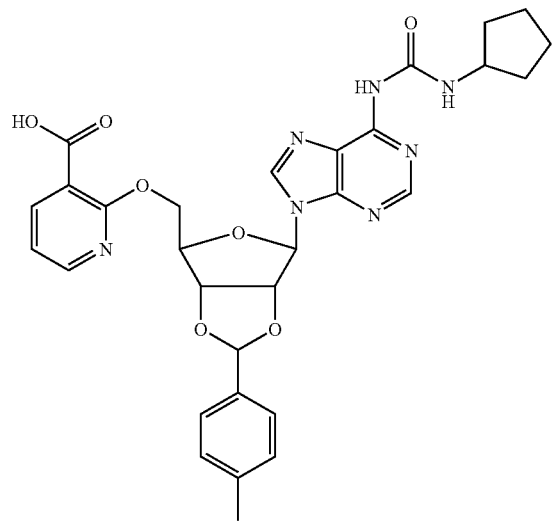

TABLE 1-continued
Exemplary Compounds.
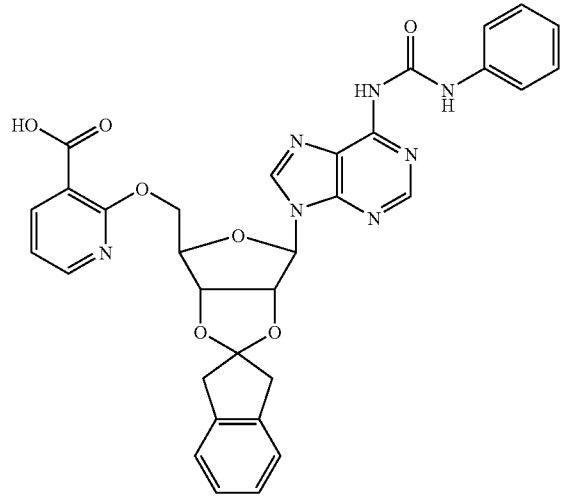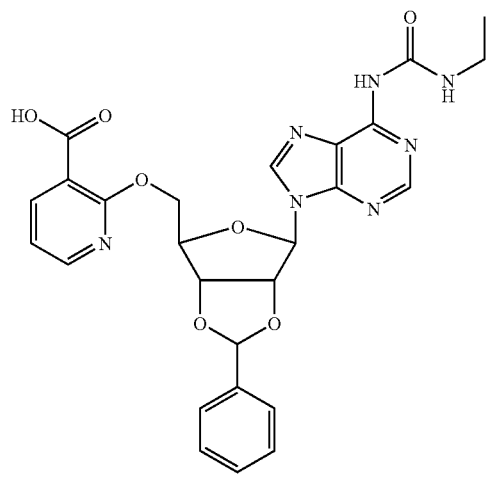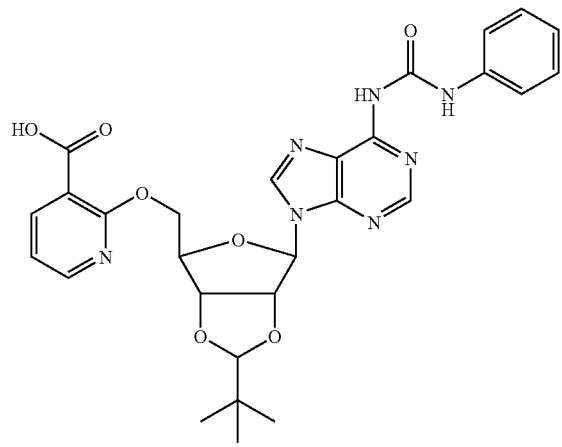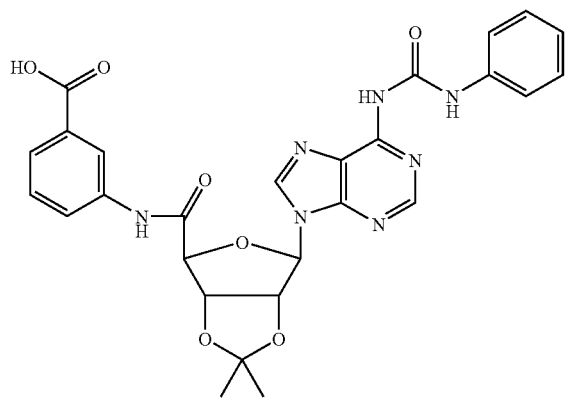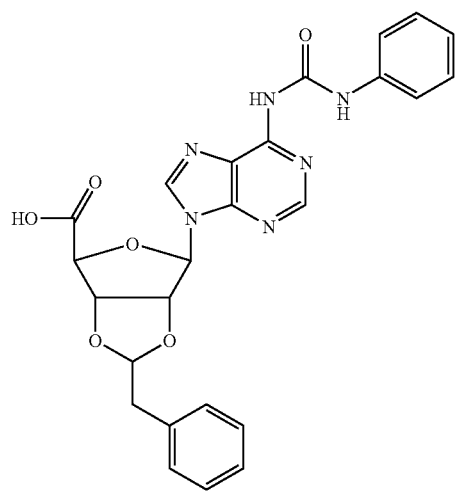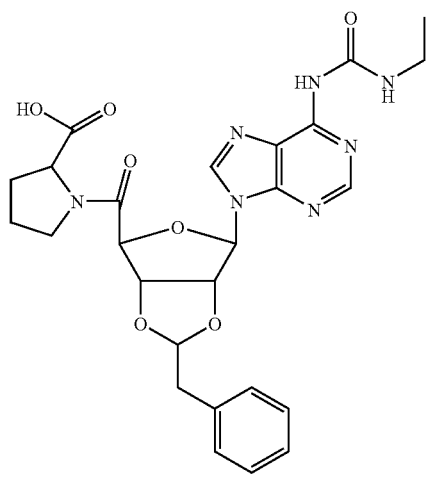

TABLE 1-continued
Exemplary Compounds.
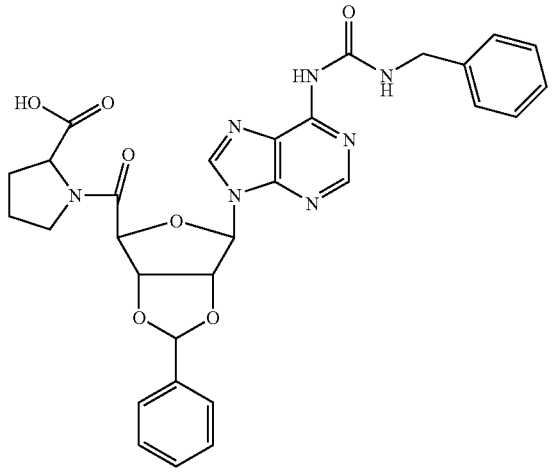
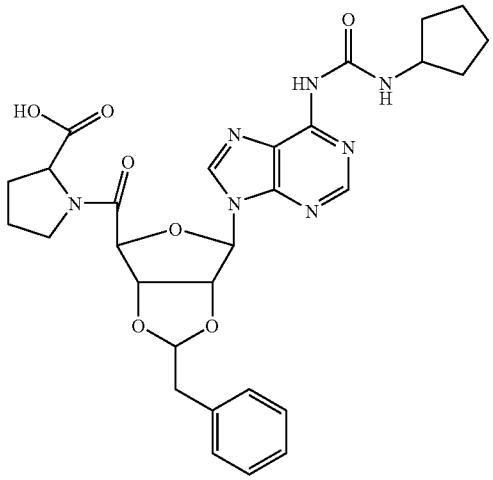
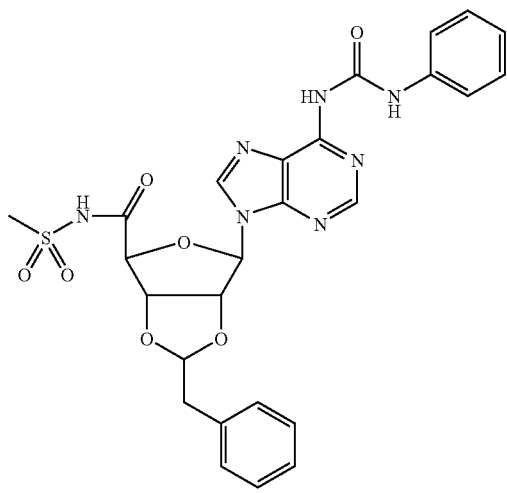
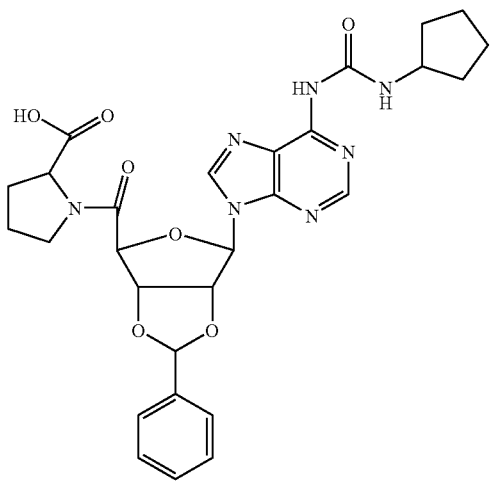
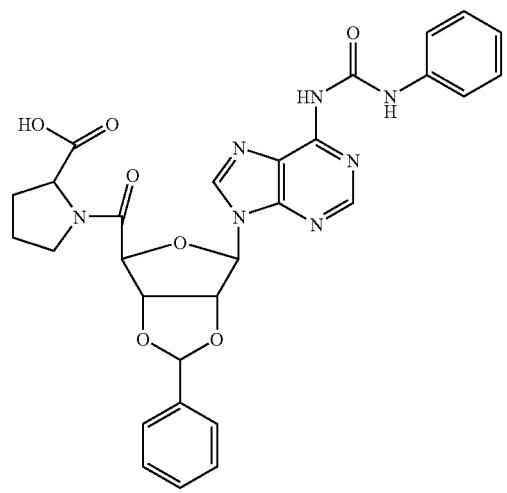
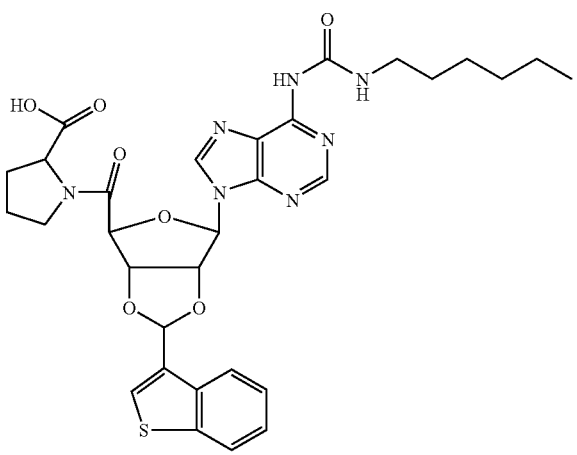

TABLE 1-continued
Exemplary Compounds.
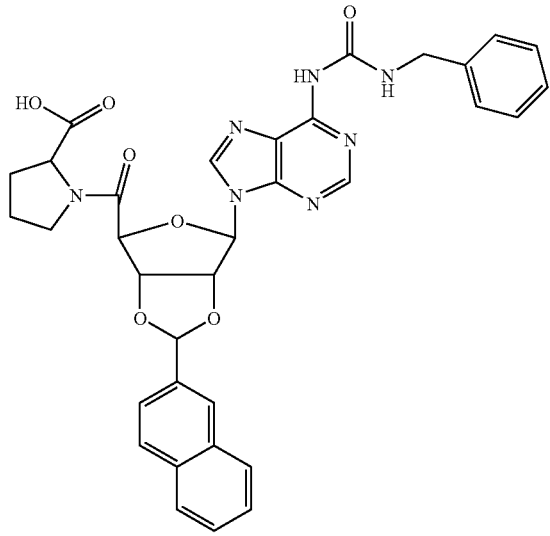 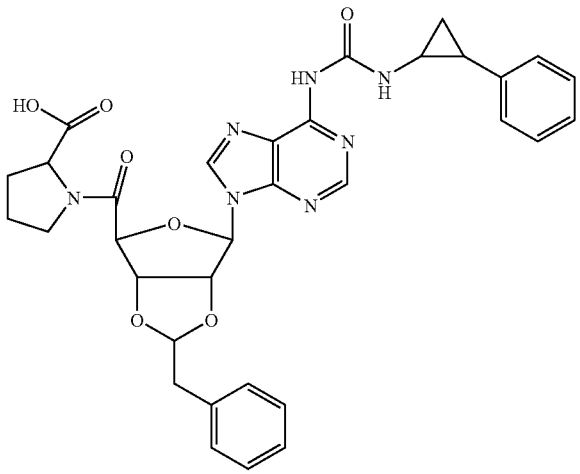
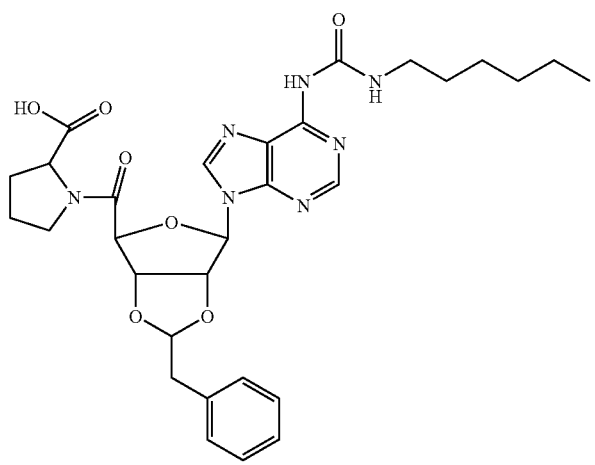 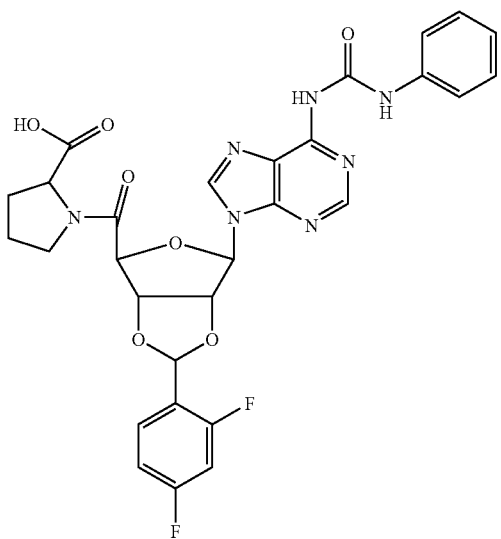
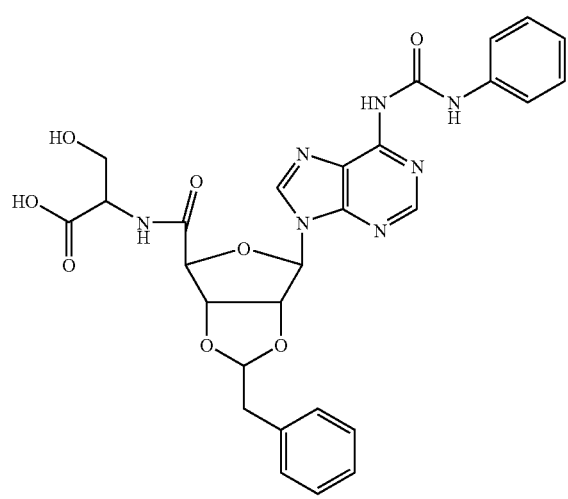 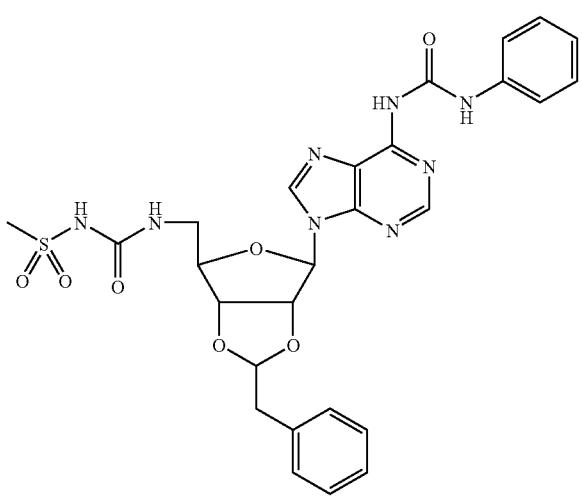

TABLE 1-continued

Exemplary Compounds.

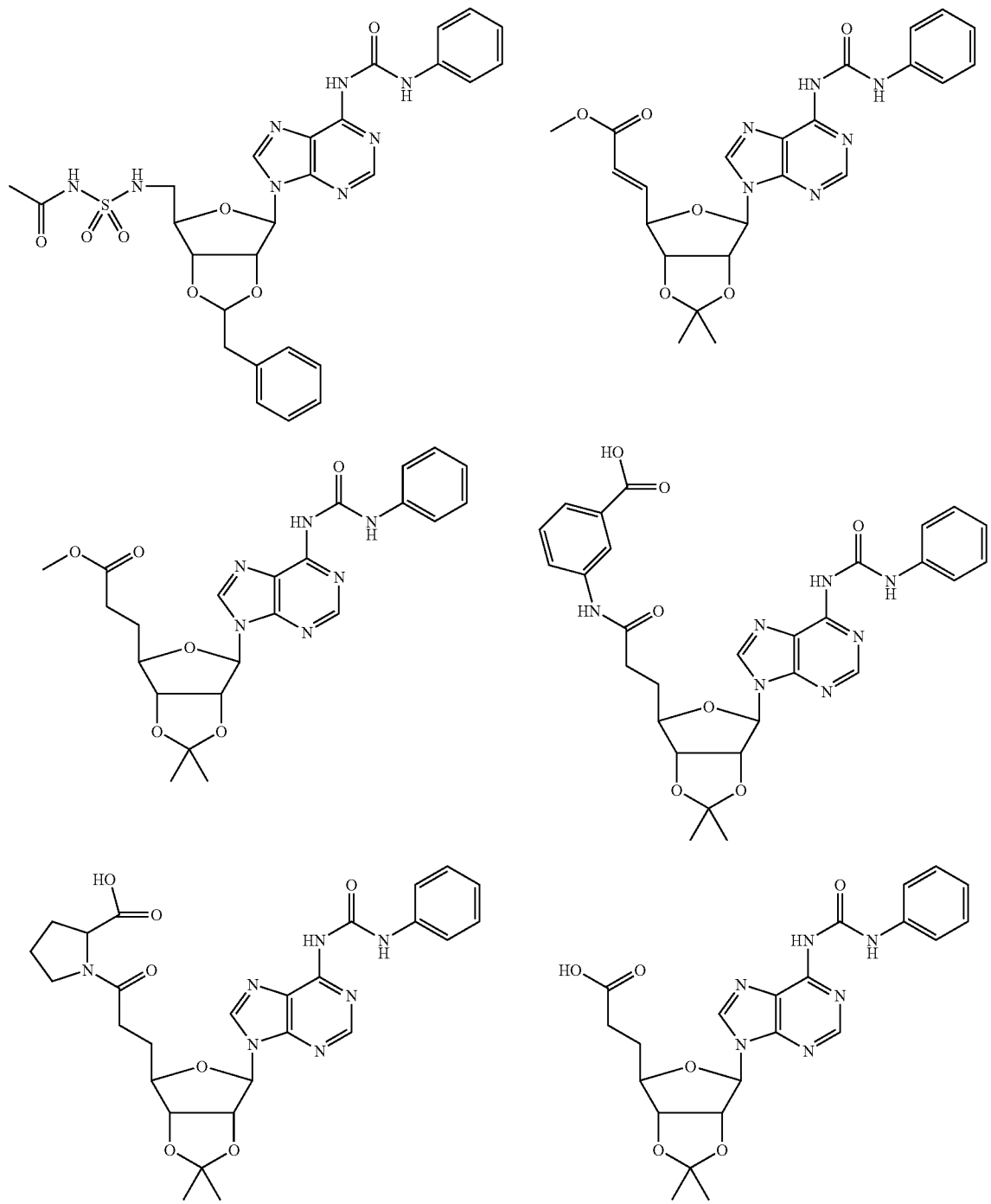

The present invention also encompasses non-toxic pharmaceutically acceptable salts of the above derivatives, such as, but not limited to, alkali metal salts such as lithium, sodium or potassium salts, or alkaline earth metal salts such as magnesium or calcium salts; or ammonium or mono-, di, tri- or tetraalkyl ammonium salts, such as $NH_4^+$, $NEH_3^+$, $NE_2H_2^+$, $NE_3H^+$, or $NE_4^+$ (wherein E is $C_{1-4}$ alkyl) salts. Other salts such as hydrochlorides, hydrobromides, mesylates, sulfates, acetates, tartrates, etc., are also contemplated in this invention. Pharmaceutically acceptable salts are salts that retain the desired biological activity of the parent compound and do not impart undesired toxicological effects. Preferred counterions are monovalent ions such as $NH_4^+$, sodium, lithium, potassium, chloride, bromide, bisulfate, and mesylate, with sodium, potassium, chloride and mesylate being most preferred due to ease of manufacture, stability, and physiological tolerance.

Those skilled in the art will recognize various synthetic methodologies which may be employed to prepare non-toxic pharmaceutically acceptable salts and prodrugs of the compounds.

Methods of Compound Preparation

The compounds of the present invention may be synthesized by those skilled in the art using conventional synthesis methodology and well-known workup and purification procedures. The following list of references, along with references cited therein, disclose general procedures employed for the synthesis of a number of intermediates and compounds related to the present invention: Baraldi, et al., *Journal of Medicinal Chemistry*, 39(3): 802-806 (1996); Camaioni, et al., *Bioorganic & Medicinal Chemistry*, 5(12): 2267-2275 (1997); Zablocki, et al., PCT International Publication No. WO01/40243; Zablocki, et al., PCT International Publication No. WO01/40246; Mantell, et al., PCT International Publication No. WO01/94368; Jacobson, et al., *Journal of Medicinal Chemistry*, 38(10): 1720-1735 (1995); Cristalli, et al., *Journal of Medicinal Chemistry*, 38(9): 1462-1472 (1995); Secrist, III and Talekar, *Nucleosides & Nucleotides*, 9(4): 619-27 (1990); Secrist, III, U.S. Pat. No. 4,794,174 (1988); Lyga and Secrist, III, *Journal of Organic Chemistry*, 48(12): 1982-1988 (1983); Dixon, et al., PCT International Publication No. WO02/096248; Hardern, et al., PCT International Publication No. WO01/36438; Guile et al., PCT International Publication No. WO00/04021; Lee, et al., *Bioorganic & Medicinal Chemistry Letters*, 13(6): 1087-1092 (2003); Cox, et. al., U.S. Pat. No. 5,747,496 (1998).

In many cases, commercially-available starting materials can be used for the 30 synthesis of compounds of this invention. When not available commercially, useful starting materials can either be obtained from stepwise modification of commercially-available compounds and derivatives, or they may be synthesized from simpler precursors using literature methods known in the art. In addition, the compounds of the present invention may be synthesized using the general methods shown in Schemes 1-12, or variations thereof.

Commercially-available materials include: adenosine, α-adenosine, 2',3'-isopropylidineadenosine, 5'-acetyl-2',3'-isopropylidineadenosine, $N^6$-(2-isopentenyl)adenosine, 2-chloroadenosine, 2-amino-6-chloropurine riboside, 6-chloropurine riboside, inosine, 8-bromoguanosine, 8-bromoadenosine, 8-azidoadenosine, 8-azaguanine, 8-azaadenine, protected ribonic acid lactone derivatives and protected furanose derivatives. Other appropriate intermediates can be purchased from commercial sources and used as starting materials for compounds of the present invention, or can be synthesized as described in the chemical literature.

As disclosed above, commercially available compounds, or their derivatives may be employed as starting materials for the methods of Schemes 1-12.

Scheme 1.
Preparation of 5'-modified ethers by nucleophilic aromatic substitution.

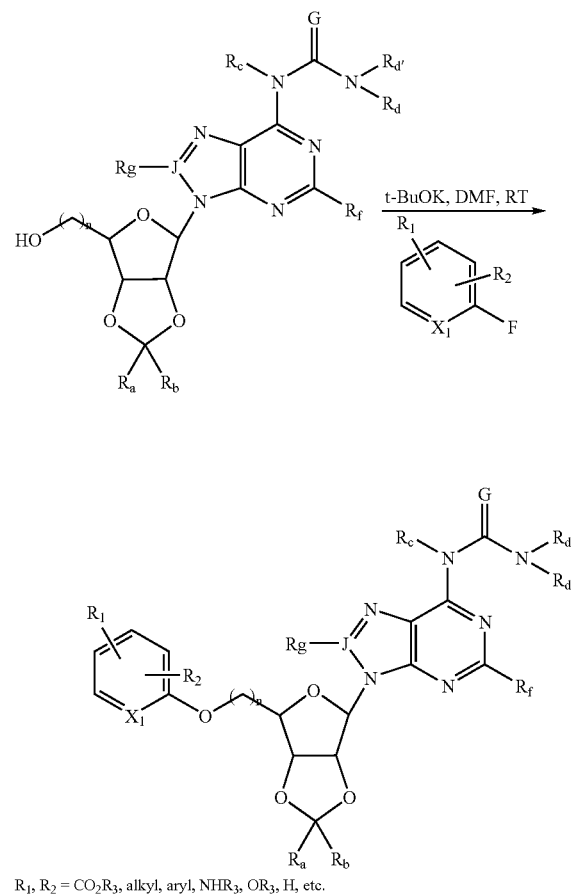

$R_1, R_2 = CO_2R_3$, alkyl, aryl, $NHR_3$, $OR_3$, H, etc.
$R_3$ = alkyl, aryl, etc; $X_1 = CR_1$, N; n = 1-6

Scheme 1, for example, discloses a useful method for the synthesis of 5'-aryl- or 5'-heteroaryl-nucleoside ethers and 8-azapurinefuranose 5'-ether derivatives by substitution of an appropriately functionalized adenosine analogue or 8-azapurine derivative for a halogen on an appropriately-substituted halogenated aromatic compound or a related heteroaromatic derivative. Groups not defined in Scheme 1 are defined as in Formula I. Preferred substituents at $R_1$ and $R_2$ of the aromatic-/heteroaromatic-group in Scheme 1 are independently hydrogen, or halogen, or groups containing carboxylic acid derivatives such as: —$CO_2R_3$; but they can also be halogen, or esters or amides of alkylcarboxylic acids, arylcarboxylic acids, —O-(alkylcarboxylic acids), —NR-(alkylcarboxylic acids), and the like. When either or both of $R_1$ and $R_2$ are halogen in Scheme 1, preferred halogens are chloro and fluoro.

Scheme 2.
Preparation of 5'-modified ethers by Mitsunobu coupling of phenols.

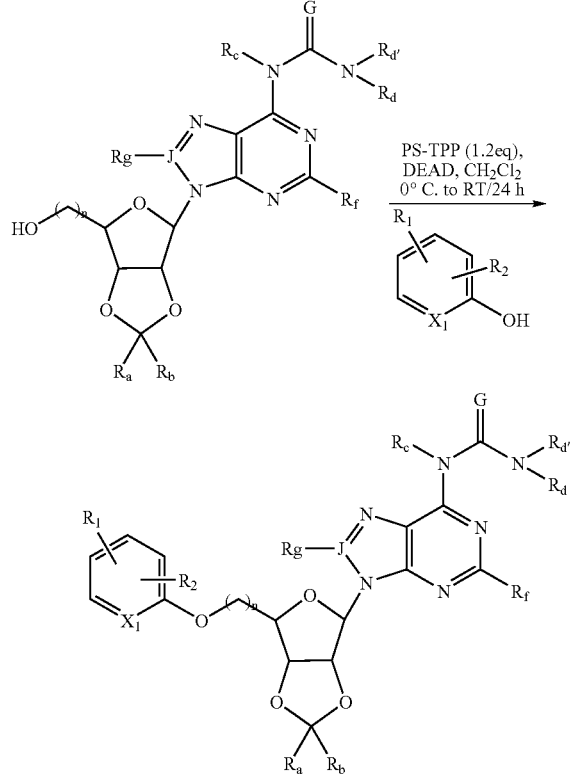

$R_1, R_2 =$ CO$_2$R$_3$, alkyl, aryl, NHR$_3$, OR$_3$, H, halogen, etc.
$R_3 =$ alkyl, aryl, etc; $X_1 =$ CR$_1$; n = 1-6

Scheme 3.
Preparation of 5'-modified isoxazole ethers by Mitsunobu coupling of isoxazole derivatives.

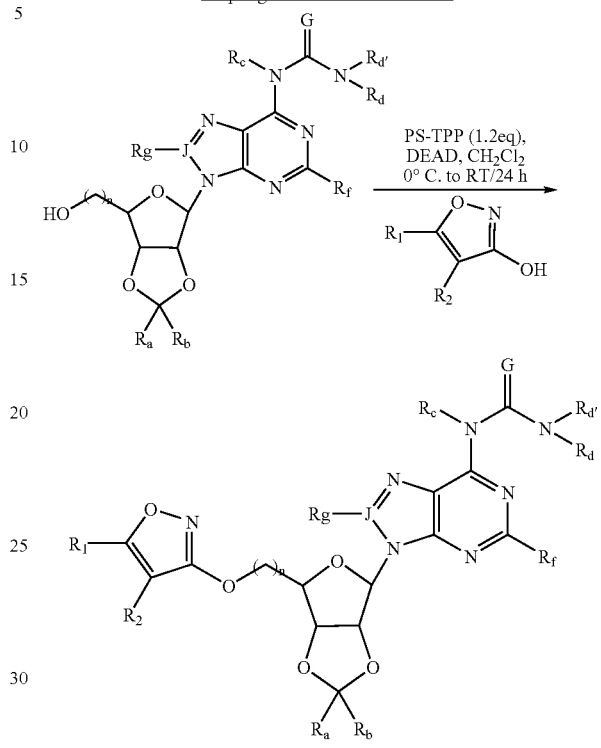

$R_1, R_2 =$ CO$_2$R$_3$, alkyl, aryl, H, NHR$_3$, OR$_3$, halogen, etc.
$R_3 =$ alkyl, aryl, etc; n = 1-6

5'-Substituted aryl nucleoside derivatives can also be prepared via Mitsunobu coupling of phenols (Mitsunobu, *Synthesis* 1-28 (1981); Brown, et al., *J. Med. Chem.* 37 (5), 674-88 (1994); Santosh and Balasubramanian, *Synthetic Communications,* 24(8), 1049-62 (1994)) to derivatives of adenosine, 8-azaadenosine, guanosine, 8-azaguanosine, etc., as provided in Scheme 2. Groups not defined in Scheme 2 are defined as in Formula I. Some preferred substituents at $R_1$, $R_2$, and $R_3$ are provided in the scheme, but these examples should not be considered limiting. For example, substituents at $R_1$ and $R_2$ of the aromatic/heteroaromatic-group in Scheme 2 independently can be hydrogen, halogen, alkyl, alkoxy, aryl or groups containing carboxylic acid derivatives such as: —CO$_2$R$_3$; but esters or amides of alkylcarboxylic acids, arylcarboxylic acids, —O-(alkylcarboxylic acids), —NR-(alkylcarboxylic acids), and the like are also included. When either or both of $R_1$ and $R_2$ are halogen in Scheme 2, preferred halogens are chloro and fluoro.

Alternatively, the Mitsunobu coupling may be carried out using hydroxyisoxazoles and the appropriate derivatives of adenosine, 8-azaadenosine, guanosine, 8-azaguanosine, etc., as provided in Scheme 3. Groups not defined in Scheme 3 are defined as in Formula I.

Some examples of preferred groups for $R_1$, $R_2$ and $R_3$ are provided in the scheme, but these examples should not be considered limiting. For example, preferred substituents at $R_1$ and $R_2$ of the isoxazole derivatives of Scheme 3 independently include hydrogen, alkoxy, or halogen, or groups containing carboxylic acid derivatives such as: —CO$_2$R$_3$; but esters or amides of alkylcarboxylic acids, arylcarboxylic acids, —O-(alkylcarboxylic acids), —NR-(alkylcarboxylic acids), and the like are also included. When either or both of $R_1$ and $R_2$ are halogen in Scheme 3, preferred halogens are chloro and fluoro.

When the products of any of Schemes 1, 2 or 3 comprise esters, said esters can be useful in the invention. Said ester derivatives may be purified by methodologies well-known in the art, such as by normal phase, or reverse phase chromatography, or in suitable circumstances, using crystallization techniques. Alternatively, said ester derivatives can be used in the synthesis of other derivatives such as amides, hydroxamic acids, and different alkyl esters by well-known methods in the art.

Optionally, said esters may be hydrolysed under basic conditions, or cleaved using other methods known in the art, which cleave esters selectively in the presence of ketals or acetals to provide acid salts. These salts are also useful in the invention.

If desired, said acid salts can be converted into acids upon mild acid treatment. Workup by common techniques, and purification by methods well known in the art, including purification by crystallization or chromatography can be used to give the purified acids. Said acids can also be converted into other useful derivatives such as amides, hydroxamic acids, aryl esters, etc., by methods known to those skilled in the art of chemical synthesis. These acid derivatives are also useful in the invention, and are also purified using well-known methods such as crystallization or chromatography.

Scheme 4.
Transformation of 2', 3'-acetals and -ketals into new acetal and ketal derivatives using solid phase techniques.

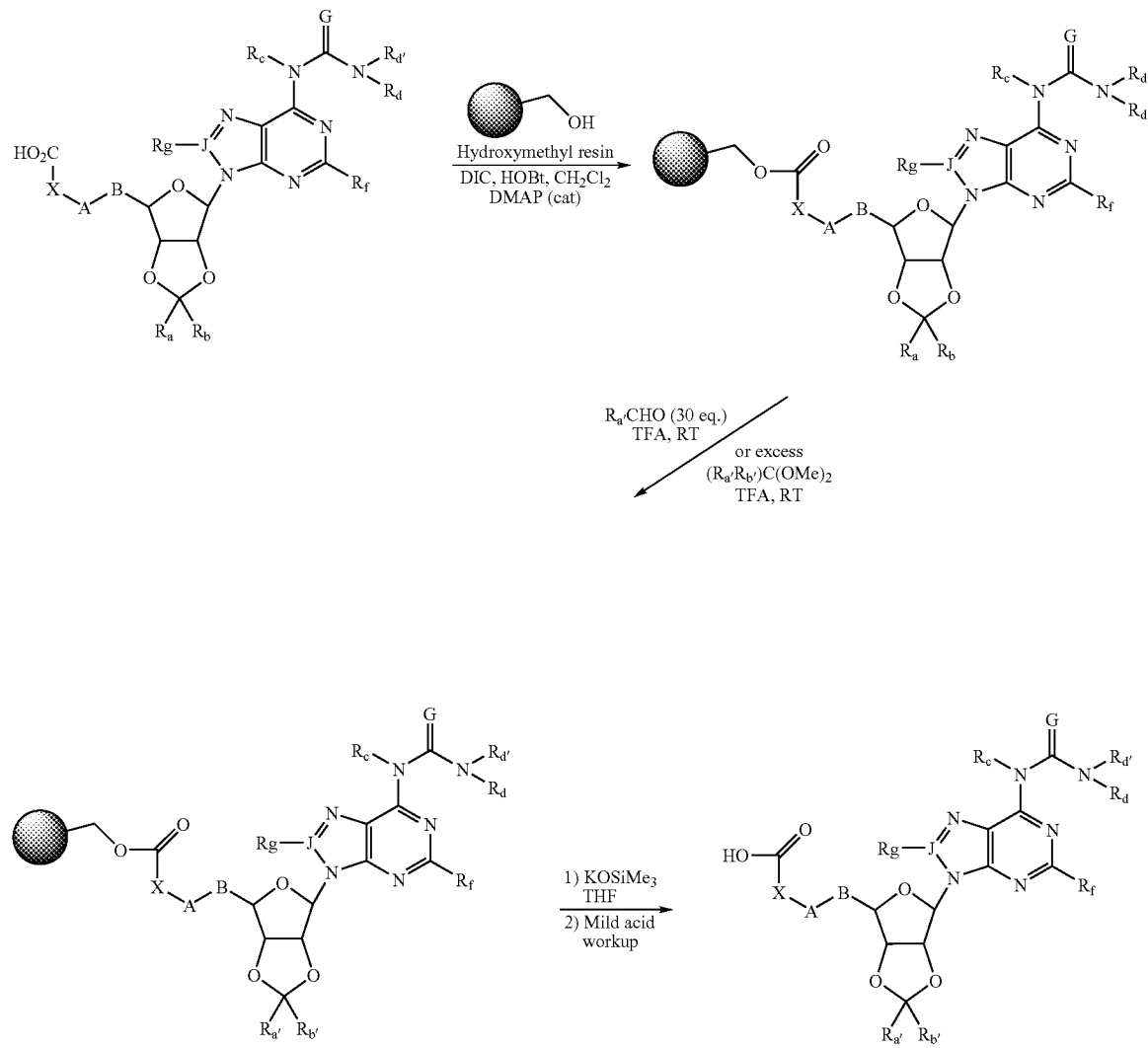

Where $R_{a'}$ and $R_{b'}$ denote different $R_a$ and/or $R_b$

Diversity using common intermediates can be introduced into the 2',3'-acetal or -ketal position of compounds encompassed in Formula I, as well as at the $N^6$-position of compounds of Formula I using solid-phase synthetic methods. Schemes 4 and 5 exemplify transketalization procedures using polymer-bound relatives of compounds of Formula 1. These methods can be used to transform one class of 2',3'-ketal or -acetal into other useful 2',3'-acetal or -ketal derivatives of adenosine, guanosine, 8-azaadenosine, etc. These polymer-bound approaches are very useful, for after the desired reaction is complete, excess reagents can be washed away using one to several solvent washes. The desired material remains attached to the resin, in a pre-purified form, until it is cleaved from the solid phase using the appropriate conditions. Final purification of the desired product is then accomplished by conventional techniques like chromatography or crystallization.

Scheme 5.
Transformation of 6-chloro derivatives into 6-urea, 6-thiourea and 6-guanidine derivatives; subsequent conversion (when desired) of 2', 3'-acetals and -ketals into new acetal and ketal derivatives using solid phase techniques.

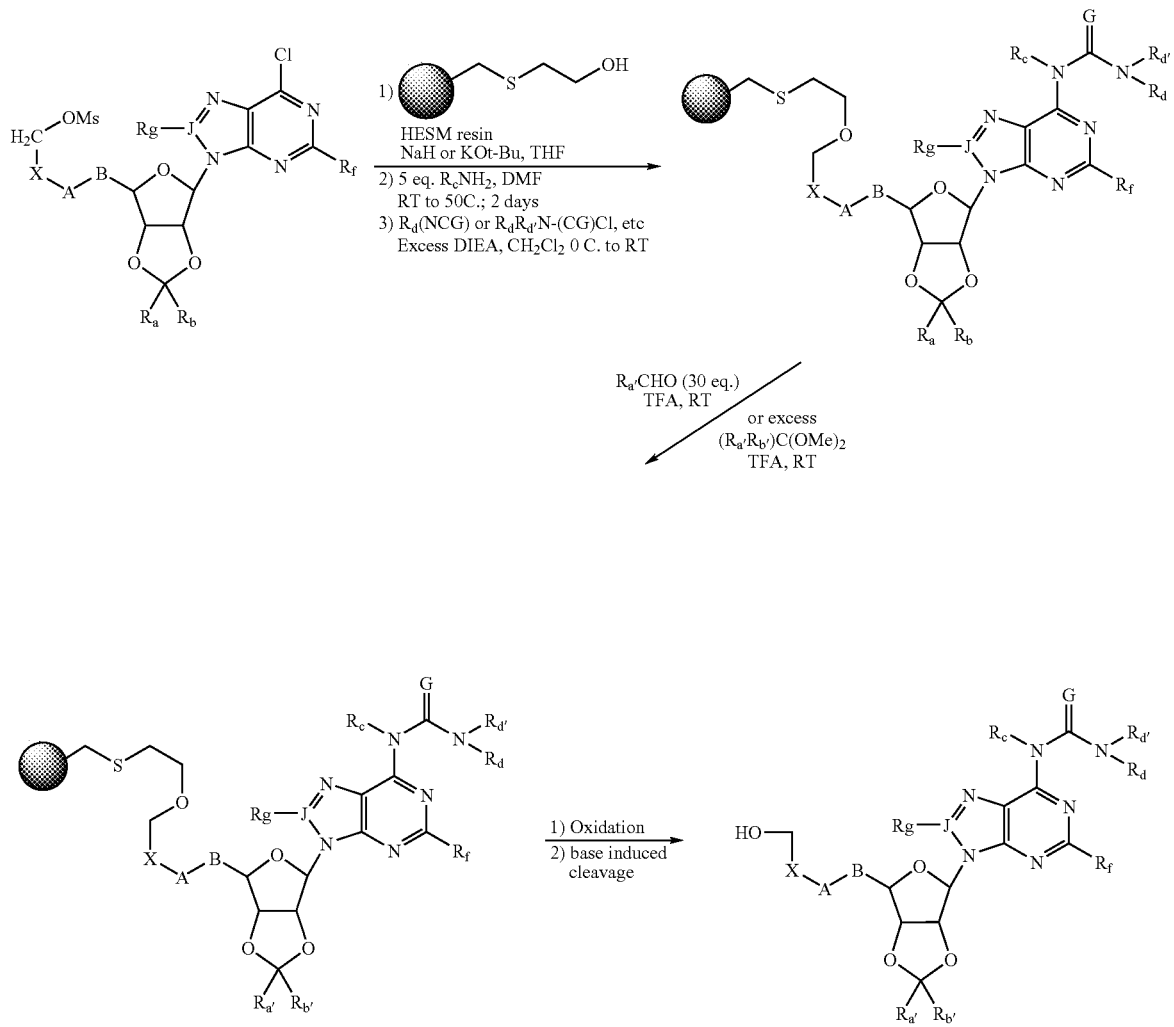

Where $R_{a'}$ and $R_{b'}$ denote different $R_a$ and/or $R_b$
and
(NCG) = —N═C═O, —N═C═S, or —N═C═N—$R_d$
(CG) = —(C═O), or —(C═S)

Scheme 5 shows another variation of compound preparation employing resin-bound materials of Formula I. It outlines a solid-phase procedure that is useful for the introduction of functionality at the 6-position, as well as for transketalization at the 2',3'-position, if desired. It should be noted that the chemistry procedures used in these solid phase approaches are similar to methods known and used for solution-phase chemical transformations involving the synthesis of adenosine, guanosine, 8-azaadenosine, etc., derivatives. The primary differences are the necessity of attachment of a starting material to a resin, the simplicity of resin-based purification techniques (filtration and washing by compatible solvents) compared to solution-phase techniques (chromatography, crystallization, etc.), and the requirement for cleavage of a compound of the invention, or an intermediate useful for the synthesis of a compound of the invention from a resin prior to final purification and/or use of a compound so cleaved.

In Scheme 5, an early intermediate, such as a 6-chloroadenosine-2',3'-ketal or -acetal derivative, or a 6-chloro-8-aza-adenosine-2',3'-ketal or -acetal derivative is attached to a resin such as polystyrene resin via a β-thioethanol linker (e.g., hydroxyethylsulfanylmethyl polystyrene; HESM polystyrene resin; Garcia-Echeverria, *Tetrahedron Lett.*, 38, 8933-7 (1997)). After workup by filtration and rinsing with a useful solvent like dimethylformamide (DMF), the resin bound material is treated with a primary amine, ammonia or a hydroxylamine derivative to introduce an amino group via displacement of the 6-chloride. As with solution phase techniques, subsequent introduction of an ureido-, thioureido-, or guanidino-group at $N^6$ can be made in one step using an excess of an appropriate isocyanate, isothiocyanate, carbodiimide, carbamoyl chloride, or 2-alkyl-2-thiopseudourea; or using a chemical equivalent of such materials. Alternatively, a two-step approach can be used to introduce a group at $N^6$, which comprises treatment of an appropriate 6-amino derivative, synthesized as in Scheme 5, with a solution of a small excess of phosgene or thiophosgene and a tertiary amine such as diisopropylethylamine in a suitable solvent such as dichloromethane or toluene at a temperature which allows reaction, followed by treatment with an excess of a primary or secondary amine to give a resin-bound urea or thiourea after workup. If desired, transketalization can be performed on a bound substrate of Scheme 5 in a manner similar to that shown in Scheme 4. Or, if a desired acetal or ketal moiety of a 6-chloroadenosine, 6-chloroguanosine, 6-chloro-8-azaadenosine, etc., derivative is used to begin with, then no transketalization is necessary. Cleavage from the β-thioethanol linker of the solid phase, as shown for the HESM polystyrene resin in Scheme 5 is performed in two steps: oxidation of the thioether-linker using an oxidizing agent like m-chloroperbenzoic acid in a solvent such as dichloromethane gives a sulfone-linker, and cleavage of the β-ether moiety from the oxidized linker occurs upon treatment with a strong base like DBU in a solvent like dichloromethane and yields a compound which can be purified by techniques known in the art. Preferred oxidizing agents include peracids like m-chloroperbenzoic acid (MCPBA) and peracetic acid, but other oxidizing agents like hydrogen peroxide, permanganate salts, or persulfate salts can be used to oxidize a thioether to a sulfone. Preferred elimination conditions include DBU in dichloromethane, and 10% ammonium hydroxide in trifluoroethanol.

Following cleavage from the solid phase, a compound formed using the procedures in Scheme 5 can be used in the present invention, or can be further modified by well-known methods for functional-group transformations to generate new compounds which are also useful for this invention.

Preferred aldehydes, aldehyde acetals and ketone ketals useful in the transketalization methods shown in Schemes 4 and 5 comprise the below said carbonyl compounds and/or derivatives of: benzaldehyde, biphenyl-3-carboxaldehyde, biphenyl-4-carboxaldehyde, biphenyl-4-yl-acetaldehyde, 2-bromobenzaldehyde, benzo[b]thiophene-3-carbaldehyde, cyclohexanecarbaldehyde, cyclopentanecarbaldehyde, 2,5-dimethylbenzaldehyde, 2,6-difluorobenzaldehyde, 2-fluorobenzaldehyde, naphthalene-2-carbaldehyde, phenyl acetaldehyde, phenyl propynal, 3-phenyl propenal, 3-phenyl propionaldehyde, 2-trifluoromethyl benzaldehyde, cyclohexanone, cyclopentanone, 4-ethyl cyclohexanone, 3,4-dihydro-1H-naphthalen-2-one, and indan-2-one. Useful derivatives for transketalization of the above ketones comprise ketals like dimethoxy- or diethoxy-ketals, etc.

In addition to the introduction of amines on the $C^6$-position using solid phase techniques as provided in Scheme 5, diversity can also be introduced at the 6-position of an adenosine, 8-azaadenosine, guanosine, etc., analog via the intermediacy of a 6-halogenated-purine derivative using solution phase methods. Scheme 6 exemplifies the preparation of 5'-isoxazole ethers, introducing ammonia, various amines or hydroxylamine derivatives at the 6-position of the purine/8-azapurine ring by displacement of a chloride leaving group (a 6-chloride is shown in Schemes 5 and 6, but the leaving group at $C^6$ could also be another type, useful for such a transformation, e.g., a 6-bromide or 6-mesylate moiety) by such materials. Amines and amine-like compounds useful for displacement of a 6-halogen intermediate as contemplated for these schemes comprise ammonia, methylamine and other N-alkyl amines; N-aralkylamines; N-cyclopropylamine and other N-cycloalkylamines; anilines; ethers and other O-derivatives of hydroxylamine; aminopyridines and other heteroaromatic amines; heterocyclic compounds having a pendant —$NHR_c$-group; and N-alkyl amines which have one or more heteroatom units like O, NR, and/or S substituted for carbon units in the alkyl chain. Such $N^6$-products can be further transformed into ureas, thioureas, or guanidines by literature methods or by methods disclosed for such transformations in Schemes 5 and 6. The materials can be purified by methods typically used in the literature, such as by chromatography or, in certain cases, by crystallization Preferred substituents at $N^6$ are ureas.

Scheme 6.
Solution phase synthesis of 5'-heteroaromatic ether-N⁶-derivatives by
Mitsunobu reaction, 6-chloride displacement, and N⁶-amine derivatization.

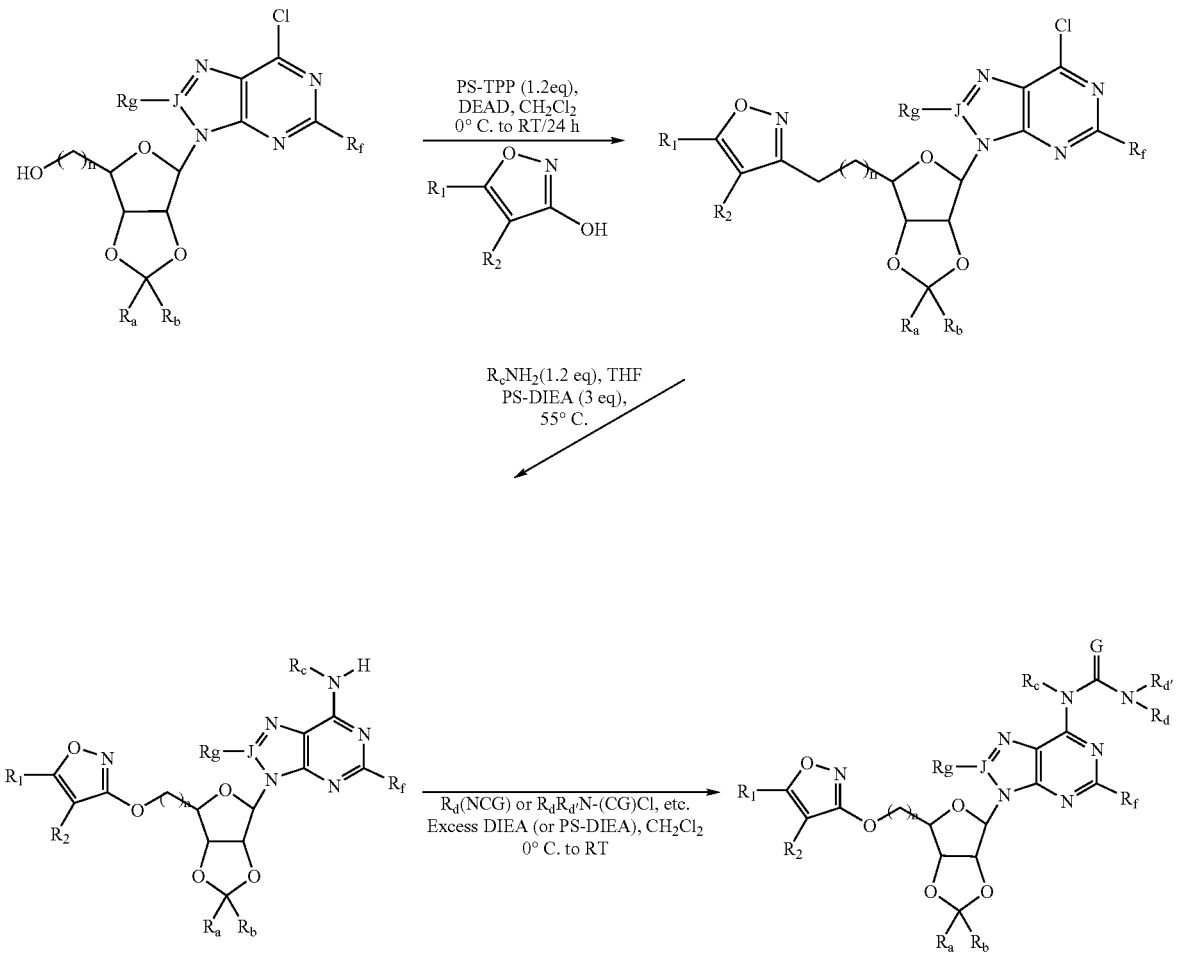

$R_1$, $R_2$ = $CO_2R_3$, alkyl, aryl, H, halogen, etc.
$R_3$ = alkyl, aryl etc; n = 1-6;
(NCG) = —N═C═O, —N═C═S,
or —N═C═N—$R_d$ (CG) =
—(C═O), or —(C═S)

When $R_1$ and/or $R_2$ of an isoxazole derivative as provided in Scheme 6 contains an ester group [e.g., —C(CO)O-(alkyl), —C(CO)O-(aryl), —(CH$_2$)$_m$C(CO)O-(alkyl), —O(CH$_2$)$_m$C(CO)O-(aryl), etc., where "m" defines a carbon chain length of a compound of Formula I], said ester can be used in the present invention, or it may be converted into an acid using a method which is compatible with an acetal or ketal moiety and a desired group at $N^6$. For example, an ester of Scheme 6 can be hydrolysed at room temperature (RT) in several hours using an excess of aqueous 2M lithium hydroxide solution dissolved in dioxane and/or methanol to give a carboxylate salt. Purification of said salt or a corresponding acid of said salt can be accomplished as previously disclosed. These acids and acid derivatives are also useful in this invention. Scheme 6 is exemplified using ammonia and primary amines (including hydroxylamine derivatives) as choices for nucleophiles in the displacement of a leaving group (like chloride) at $C^6$. Further modification of the $N^6$-group of a compound of Scheme 6 with a —[(CG)NR$_d$R$_d$']-group yields a compound useful in the invention.

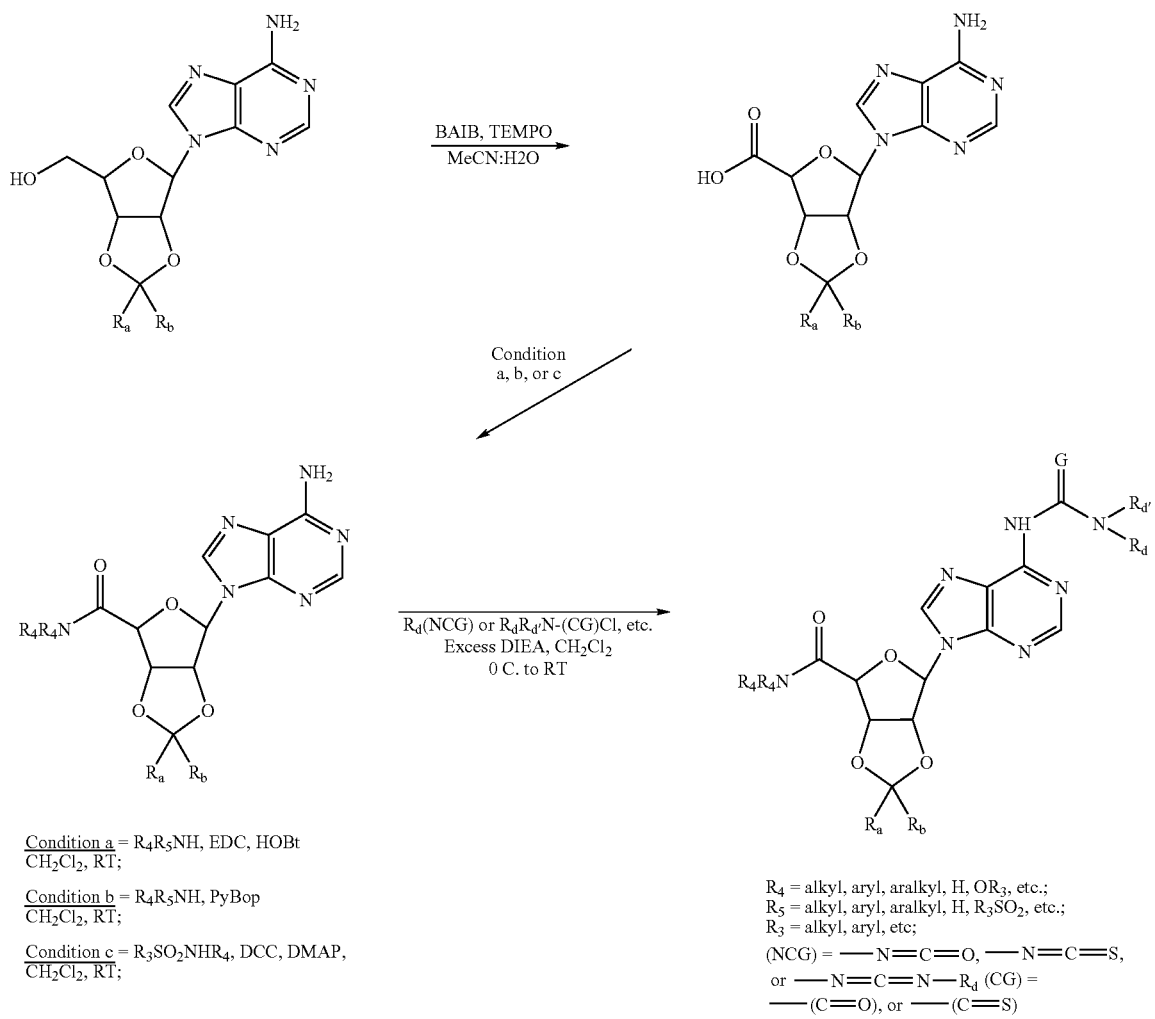

Scheme 7.
Synthesis of 2',3'-O-Isopropylideneadenosine-5'-carboxylic acid, related acetals and ketals, and their use as intermediates for the synthesis of compounds of this invention.

2',3'—O-Isopropylideneadenosine-5'-carboxylic acid and related acetals and ketals are useful intermediates for the preparation of various amides and sulfonamide derivatives. An intermediate of this type can be used in both solution phase and solid phase synthetic schemes to prepare compounds with various substituents at the 5'-,2',3'-acetal/ketal-, and 6-positions of adenosines or related purine derivatives as provided in Scheme 7. The methods shown in Scheme 7 are also useful for the preparation of substituted purine derivatives, and/or 8-azapurine derivatives.

Compounds containing the adenosine 5'-carboxylic acid unit shown in Scheme 7, or related $N^6$-substituted-adenosine-5'-carboxylic acids and 8-azaadenosine-5'carboxylic acids can also be used for the synthesis of esters or other materials useful in this invention using literature methods. In addition, the $N^6$-amine of such an acid can be transformed into a urea, thiourea, or guanidine, or into a protected group such as a benzamide, and the acid moiety which is at, or linked to, the 5'-position of the furanose derivative can be coupled to a solid phase resin such as a 4-sulfamylbutyryl resin, hydroxymethyl resin, or a pegylated-hydroxy resin, etc., using techniques well-known in the peptide literature and/or solid phase organic synthesis literature to give a resin-bound material. The benefits of solid-phase chemistry can then be gained for modification of a resin-bound material by transketalization techniques similar to those shown in Schemes 4 and 5. If a protecting group is used on the $N^6$-position of such an acid, it can be removed subsequent to a transketalization procedure, and a $N^6$-amine so formed can be converted into a urea, thiourea or guanidine by methods disclosed herein, or by methods in the literature. Cleavage from the solid support using known methods then yields a compound of the invention which can be purified, if needed, by employing commonly-used techniques.

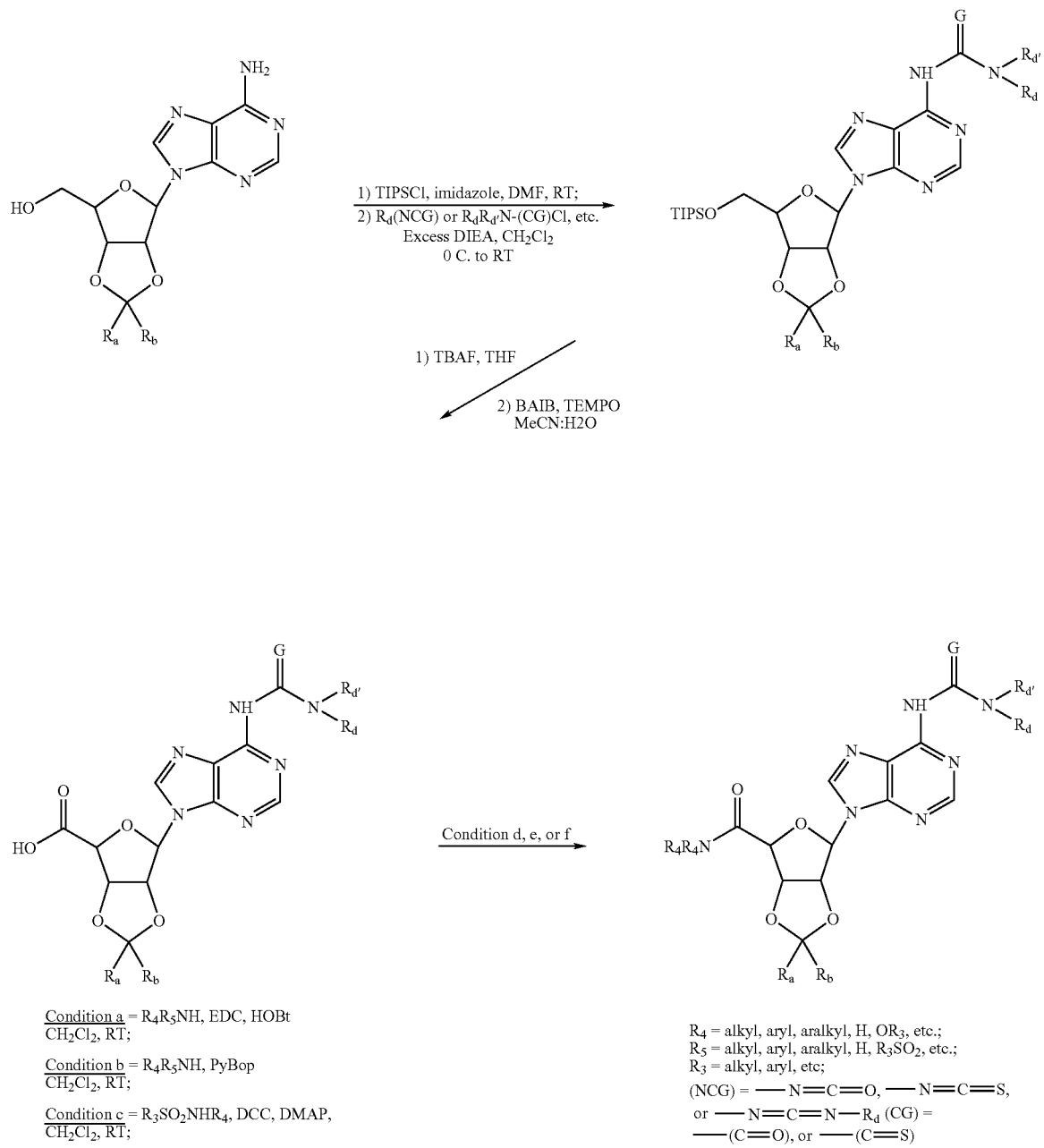

Scheme 8.
N[6]-modification of adenosine derivatives, followed by oxidation to a 5'-carboxylic acid, and 5'-amide formation.

Condition a = R₄R₅NH, EDC, HOBt CH₂Cl₂, RT;

Condition b = R₄R₅NH, PyBop CH₂Cl₂, RT;

Condition c = R₃SO₂NHR₄, DCC, DMAP, CH₂Cl₂, RT;

$R_4$ = alkyl, aryl, aralkyl, H, $OR_3$, etc.;
$R_5$ = alkyl, aryl, aralkyl, H, $R_3SO_2$, etc.;
$R_3$ = alkyl, aryl, etc;
(NCG) = —N=C=O, —N=C=S, or —N=C=N—$R_d$ (CG) = —(C=O), or —(C=S)

A variation of the method disclosed in Scheme 7, useful for the introduction of a group at $N^6$ prior to oxidation of the 5'-position of an adenosine derivative or an 8-azaadenosine derivative, is shown in Scheme 8. Although Scheme 8 shows an adenine unit, it will be understood by chemistry practioners that the methods of Scheme 8 are generally applicable to substituted members of the adenine family and also to the 8-azaadenines.

Preferred amines and amine derivatives for the 5'-amide-forming reactions shown in Schemes 7 and 8 are: trifluoromethanesulfonamide, methanesulfonamide, serine, glycine, proline, anthranilic acid and its regioisomers, and methyl anthanilate and its regioisomers.

acids and peptides, or derivatives, to a 5'-carboxylic acid or related homologue is exemplified in Scheme 9 using the amino acid, proline.

An example of the method is shown in Scheme 9 utilizing a resin-linker combination like the polystyrene/HESM as a solid phase. Other solid phase/linkers known in the art can also be used in this method. Attachment of a group, such as an amino acid, (e.g., proline, as shown) or a series of amino acids, or a peptide, by well-known methods in the art of solid phase synthesis yields a resin-linked amine. Said amine can then be reacted with an adenosine 5'-carboxylic acid, or another type of derivative useful for making compounds of

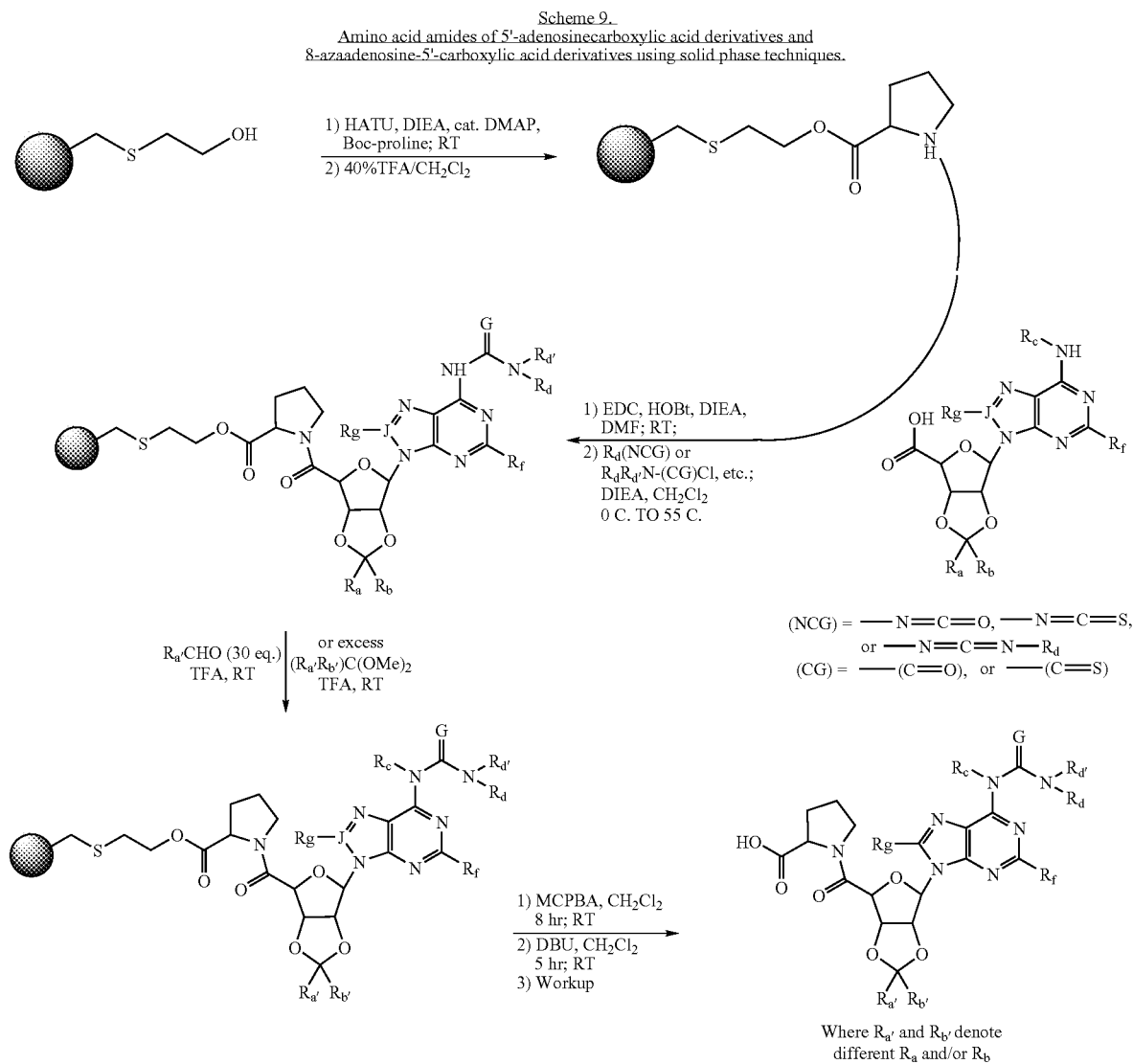

Amide derivatives of 5'-carboxylic acids (e.g., those shown in Scheme 7 and Scheme 8) or amide derivatives of acid moieties linked at the 5'-position of Formula I can also include amides derived from amino acids, peptides, aminoalcohols and the like. A convenient way of attaching naturally-occurring, as well as synthetically-derived amino this invention, to yield a coupled product. The said coupled product, if it bears an amine at the 6-position, can then be treated with one of the various reagents described previously, or with a reagent known in the literature, to yield a urea, thiourea or guanidine at the adenosine 6-position. Alternatively, if a 5'-carboxylic acid derivative used in a coupling to a solid phase has a urea, etc., already installed at the 6-position, then the latter said modification at $N^6$ need not be performed. If desired, a coupled 5'-amide/$N^6$-derivatized product can be converted into a variety of different acetals or ketals using solid phase methods such as described for Schemes 4 and 5. When a synthesis is complete, cleavage of a compound of the invention from a solid phase can be performed by a variety of methods known in the art; such cleavage conditions depending upon the type of linker used. Cleavage methodologies useful for cleaving peptide- or amino acid derivatives of 5'-linked-adenosine compounds comprise the linker oxidation/elimination procedures given in Schemes 5 and 9; treatment with a hydroxide source, such as lithium hydroxide, using conditions as for the ester hydrolysis described in Scheme 6; and hydrolysis using potassium trimethylsilanolate, as described in Scheme 4; as well as others known in the art (including aminolysis to form amides). If desired, a compound useful in this invention can be obtained in purified form by cleaving it from a resin and purifying it as described previously.

Scheme 10.
Synthesis of 5'-amines and 5'-amine derivatives
of nucleosides and 8-azanucleosides.

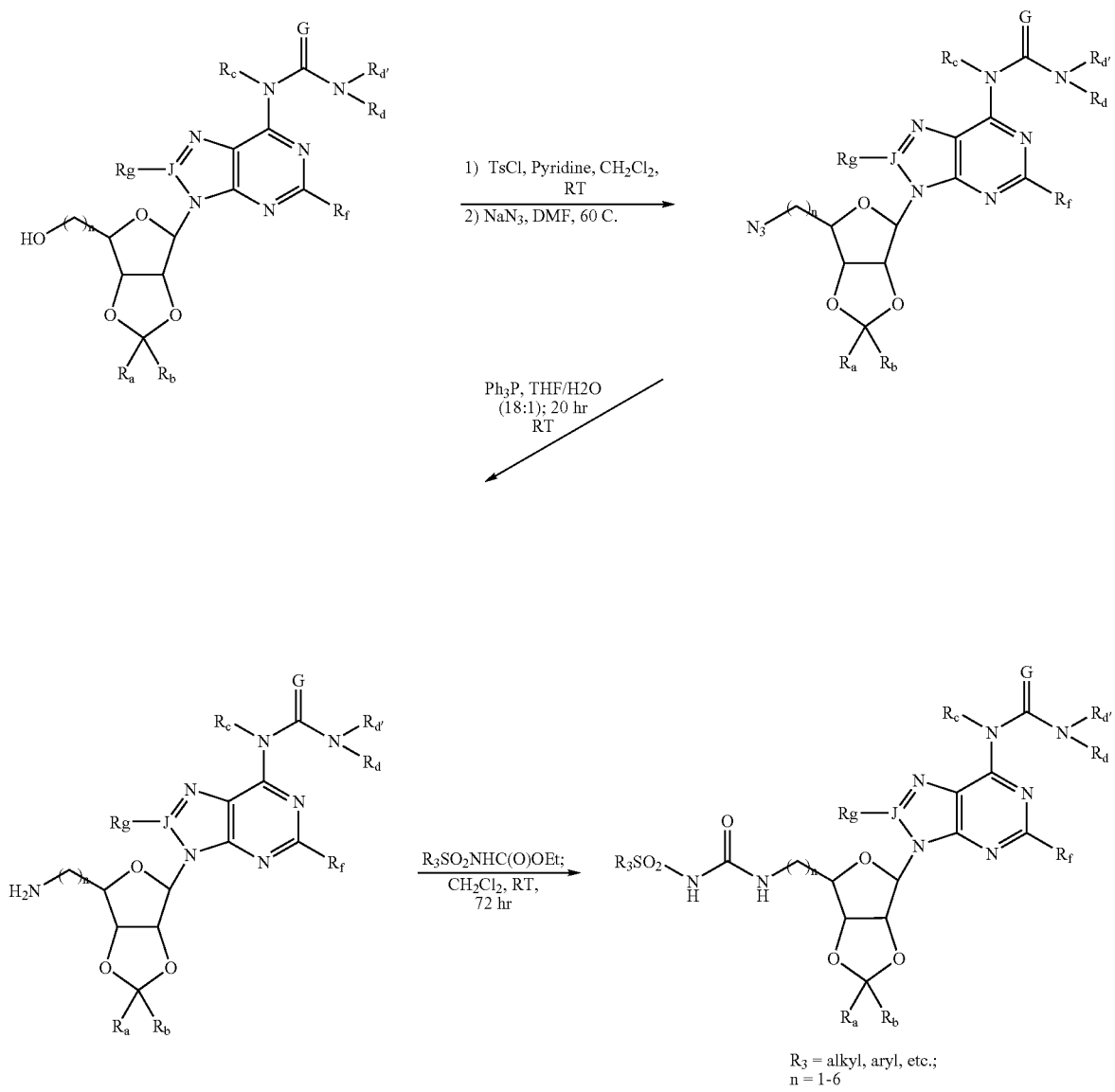

In another embodiment, an amino group can be installed at the 5'-position of an adenosine or 8-azaadenosine analogue, or on the chain of a 5'-homologue of such a material. This amine can be utilized to form amide-, sulfonamide-, and other derivatives. Scheme 10 illustrates how a sulfonylurea can be synthesized at the 5'-position using a 5'-amine, or at related positions on homologous amine derivatives. In addition, an amine introduced at the 5'-position or on the 5'-chain of a homologue is also useful for the synthesis of amides, ureas, sulfonamides and other amine derivatives using methods known in the art for such processes.

Scheme 11.
Homologation of adenosine derivatives, including steps involving oxidation, Wittig or Horner-Emmons Reaction, reduction and coupling with amines.

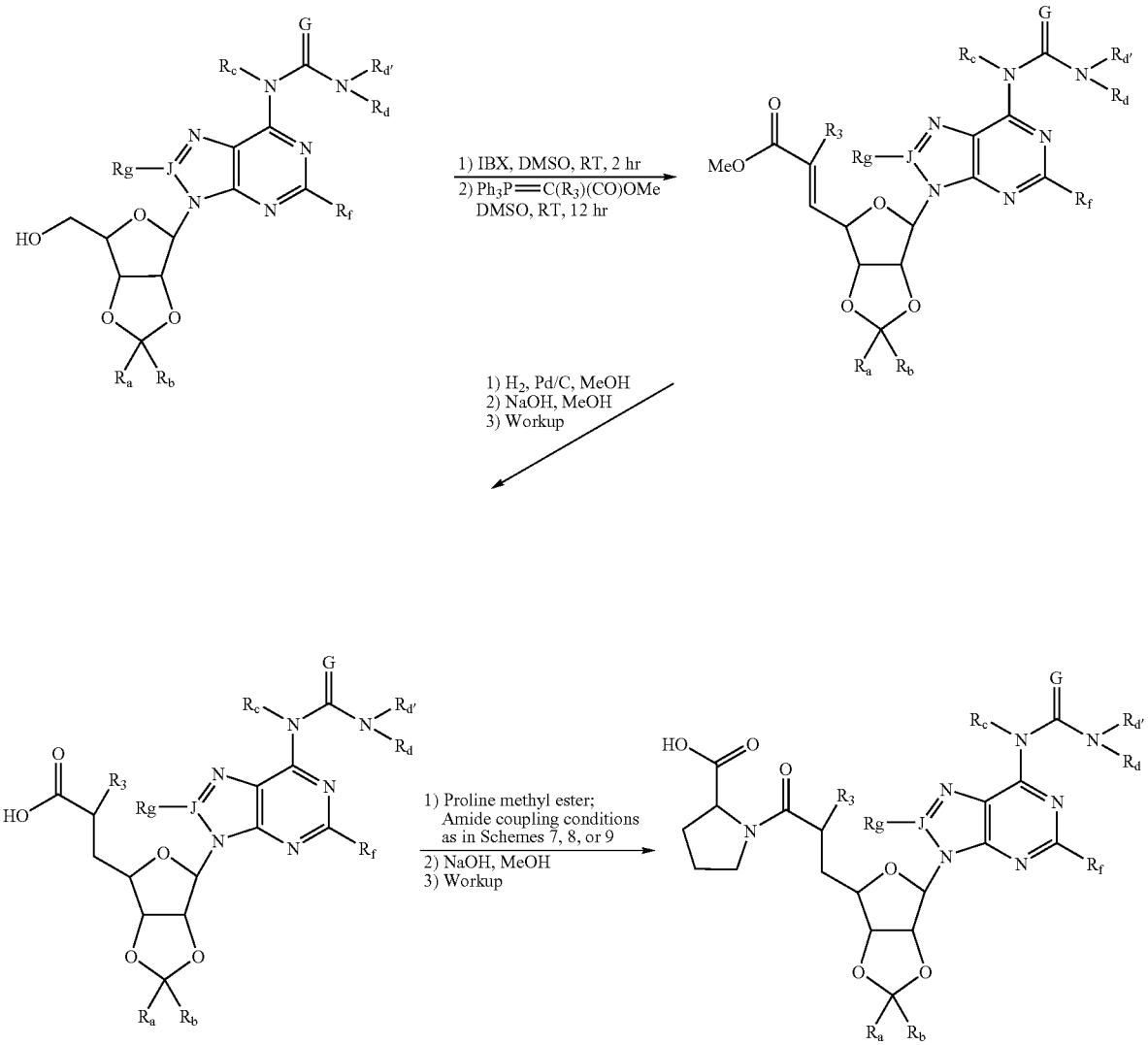

In still another embodiment, the 5'-position of the nucleoside derivative or 8-azanucleoside derivative is homologated with one or more carbon atoms, affording compounds with different distances between the atoms of the tetrahydrofuran ring and the homologated group. Scheme 11 illustrates the preparation of a a class of homologated adenosine analogs which are useful for the invention. Or, if desired, such a homologue can subsequently be coupled with an amino acid to give other compounds useful for this invention. In Scheme 11, proline is used to exemplify the amide coupling, but other amines or amino acid derivatives can be employed. In Scheme 12, the reduction step of Scheme 11 is omitted, which generates unsaturated homologues useful in this invention.

conditions necessary to attach and remove such groups will be apparent to those skilled in the art.

The inventors of the present invention have discovered non-nucleotide compounds that are antagonists of the $P2Y_{12}$ receptor and are also useful as antithrombotic agents. These materials have the ability to block the action of ADP at its platelet receptor site and prevent platelet aggregation. These compounds can provide a more efficacious antithrombotic effect than aspirin, but with less gastrointestinal bleeding. Since ADP-induced platelet aggregation is mediated by the simultaneous activation of both $P2Y_{12}$ and $P2Y_1$ receptors,

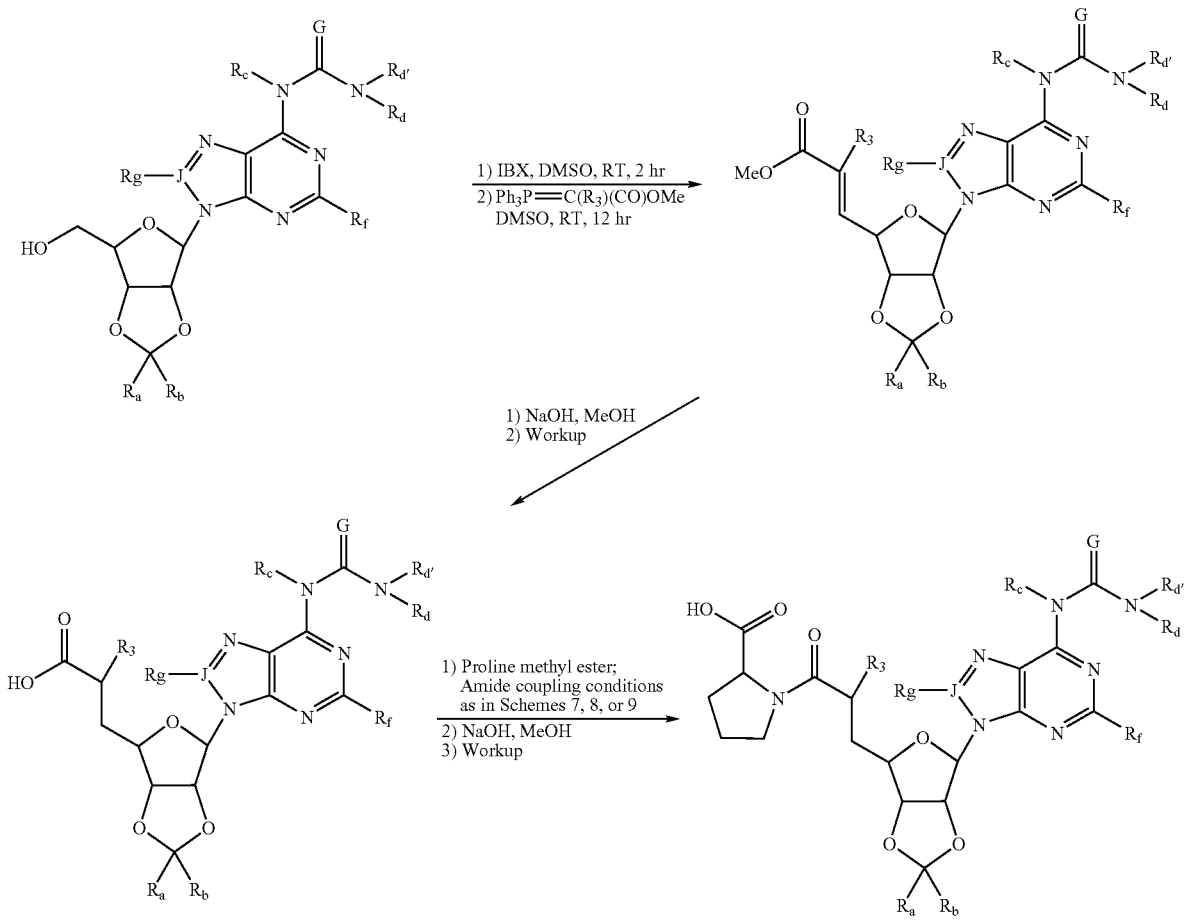

Those having skill in the art will recognize that the starting materials can be varied and additional steps employed to produce compounds encompassed by the present invention, as shown in the above schemes and as demonstrated by the examples which follow. In some cases, protection of certain reactive functionalities may be necessary to achieve some of the above transformations. In general, the need for such protecting groups as well as the the combined administration of the compounds described here with antagonists of platelet $P2Y_1$ receptors could potentially provide a more efficacious antithrombotic effect at concentrations of each antagonist that are below the effective concentrations to block each receptor subtype in other systems, resulting in a decrease of the potential manifestation of adverse effects. In addition, $P2Y_{12}$ antagonists can be used in conjunction with lower doses of agents which inhibit platelet aggregation by different mechanisms, to reduce the side effects of the latter agents.

The compounds of Formula I can also be used for diagnostic purposes. If the Formula I compounds have sufficient binding affinity and bear a fluorescent moiety, they can find uses as biochemical probes for the $P2Y_{12}$ receptor on platelets or other tissues. This can be useful to determine the general health of, or receptor levels on tissues or platelets.

The compounds of general Formula I and especially those of Formula Ia are useful in therapy, in particular in the prevention of platelet aggregation. The compounds of the present invention are thus useful as anti-thrombotic agents, and are thus useful in the treatment or prevention of conditions such as, but not limited to, unstable angina, coronary angioplasty (PTCA) and myocardial infarction.

The compounds of the present invention are also useful in the treatment or prevention of primary arterial thrombotic complications of atherosclerosis such as thrombotic stroke, peripheral vascular disease, and myocardial infarction without thrombolysis.

Still further indications where the compounds of the invention are use fill are for the treatment or prevention of arterial thrombotic complications due to interventions in atherosclerotic disease such as angioplasty, endarterectomy, stent placement, coronary and other vascular graft surgery, as well as complications due to anesthesia during surgery.

Still further indications where the compounds of the invention are usefull are for the treatment or prevention of thrombotic complications of surgical or mechanical damage such as tissue salvage following surgical or accidental trauma, reconstructive surgery including skin flaps, and "reductive" surgery such as breast reduction.

The compounds of the present invention are also useful for the prevention of 30 mechanically-induced platelet activation in vivo such as cardiopulmonary bypass (prevention of microthromboembolism), prevention of mechanically-induced platelet activation in vitro such as the use of the compounds in the preservation of blood products, e.g. platelet concentrates, prevention of shunt occlusion such as renal dialysis and plasmapheresis, thrombosis secondary to vascular damage/inflammation such as vasculitis, arteritis, glomerulonephritis and organ graft rejection.

Still further indications where the compounds of the present invention are useful are indications with a diffuse thrombotic/platelet consumption component such as disseminated intravascular coagulation, thrombotic thrombocytopenic purpura, hemolytic uremic syndrome, heparin-induced thrombocytopenia and pre-eclampsia/eclampsia.

Still further indications where the compounds of the invention are useful are for the treatment or prevention of venous thrombosis such as deep vein thrombosis, veno-occlusive disease, hematological conditions such as thrombocythemia and polycythemia, and migraine.

In a particularly preferred embodiment of the present invention, the compounds are used in the treatment of unstable angina, coronary angioplasty, myocardial infarction, stroke, and/or peripheral arterial disease.

In another particularly preferred embodiment of the present invention, the compounds are useful as adjunctive therapy in the prevention of coronary arterial thrombosis during the management of unstable angina, coronary angioplasty and acute myocardial infarction, i.e. perithrombolysis. Agents commonly used for adjunctive therapy in the treatment of thrombotic disorders may be used, for example clopidogrel, heparin and/or aspirin, just to mention a few.

A method of treating a mammal to alleviate the pathological effects of atherosclerosis and arteriosclerosis, acute MI, chronic stable angina, unstable angina, transient ischemic attacks and strokes, peripheral vascular disease, arterial thrombosis, preeclampsia, embolism, restenosis or abrupt closure following angioplasty, carotid endarterectomy, and anastomosis of vascular grafts.

The compounds of this invention may be used in vitro to inhibit the aggregation of platelets in blood and blood products, e.g. for storage, or for ex vivo manipulations such as in diagnostic or research use. This invention also provides a method of inhibiting platelet aggregation and clot formation in a mammal, especially a human, which comprises the internal administration of a compound of Formula (I) and a pharmaceutically acceptable carrier.

Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment.

This invention further provides a method for inhibiting the reocclusion of an artery or vein following fibrinolytic therapy, which comprises internal administration of a compound of Formula (I) and a fibrinolytic agent. When used in the context of this invention, the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule.

Extracorporeal circulation is routinely used for cardiovascular surgery in order to oxygenate blood. Platelets adhere to surfaces of the extracorporeal circuit. Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

The active compounds may be administered systemically to target sites in a subject in need such that the extracellular concentration of a $P2Y_{12}$ agonist is elevated to block the binding of ADP to P2Y$_{12}$ receptor, thus inhibit the platelet aggregation. The term systemic as used herein includes subcutaneous injection, intravenous, intramuscular, intrasternal injection, intravitreal injection, infusion, inhalation, transdermal administration, oral administration, rectal administration and intra-operative instillation.

For systemic administration such as injection and infusion, the pharmaceutical formulation is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile indictable preparation may be a sterile indictable solution or suspension in a non-toxic acceptable diligent or solvent. Among the acceptable vehicles and solvents that may be employed are sterile water, saline solution, or Ringer's solution.

Another method of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs.

For oral use, an aqueous suspension can be prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use may also be presented as chewable gums by embedding the active ingredient in gums so that the active ingredient is slowly released upon chewing.

Additional means of systemic administration of the active compound to the target platelets of the subject would involve a suppository form of the active compound, such that a therapeutically effective amount of the compound reaches the target sites via systemic absorption and circulation.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The active compounds may also be systemically administered to the platelet aggregation sites through absorption by the skin using transdermal patches or pads. The active compounds are absorbed into the bloodstream through the skin. Plasma concentration of the active compounds can be controlled by using patches containing different concentrations of active compounds.

One systemic method involves an aerosol suspension of respirable particles comprising the active compound, which the subject inhales. The active compound would be absorbed into the bloodstream via the lungs, and subsequently contact the target platelets in a pharmaceutically effective amount. The respirable particles may be liquid or solid, with a particle size sufficiently small to pass through the mouth and larynx upon inhalation; in general, particles ranging from about 1 to 10 microns, but more preferably 1-5 microns, in size are considered respirable.

Another method of systemically administering the active compounds to the platelet aggregation sites of the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

Intravitreal delivery may include single or multiple intravitreal injections, or via an implantable intravitreal device that releases P2Y$_{12}$ antagonists in a sustained capacity. Intravitreal delivery may also include delivery during surgical manipulations as either an adjunct to the intraocular irrigation solution or applied directly to the vitreous during the surgical procedure.

For systemic administration, plasma concentrations of active compounds delivered may vary according to compounds; but are generally $1\times10^{-10}$-$1\times10^{-5}$ moles/liter, and preferably $1\times10^{-8}$-$1\times10^{-6}$ moles/liter.

The pharmaceutical utility of P2Y$_{12}$ antagonist compounds of this invention is indicated by their inhibition of ADP-induced platelet aggregation. This widely used assay, as described in S. M. O. Hourani et al. *Br. J. Pharmacol.* 105, 453-457 (1992) relies on the measurement of the aggregation of a platelet suspension upon the addition of an aggregating agent such as ADP.

The present invention also provides novel pharmaceutical compositions. The pharmaceutical compositions are pharmaceutically acceptable formulations comprising one or more compounds of Formula I of high purity, and/or in a pharmaceutically acceptable carrier. The pharmaceutically acceptable carrier can be selected by those skilled in the art using conventional criteria. Pharmaceutically acceptable carriers include, but are not limited to, saline and aqueous electrolyte solutions, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

The invention is illustrated further by the following examples that are not to be construed as limiting the invention in scope to the specific procedures described in them.

EXAMPLES

Example 1

Preparation of 5'-aryl ether derivatives

5-Amino-2-{2-benzyl-6-[6-(3-phenyl-ureido)-purin-9-yl]-tetrahydro-furo [3,4-d][1,3]dioxol-4-yl-methoxy}-benzoic acid Adenosine (10 g, 37 mmol was dissolved in N,N-dimethyl formamide (100 mL) and dimethoxypropane (25 mL) followed by addition of Amberlyst 15H$^+$ resin. The mixture was stirred 3 h at 55° C. The resin was removed by filtration and the solvents removed in vacuo, affording 2',3'-di-O-isopropylidene adenosine (11 g, 95%).

This product (6 g, 20 mmol) was dissolved in N,N-dimethyl formamide (22 mL) and stirred with triisopropylsilyl chloride and imidazole 16 h at 23° C. The solution was partitioned between ether (200 mL) and brine (100 mL) and the ether phase washed with additional brine (2×50 mL). The ether was dried over magnesium sulfate and evaporated, affording 5'-O-triisopropylsilyl-2',3'-di-O-isopropylidene adenosine.

This residue was dissolved in toluene (20 mL) and treated with phenylisocyanate (3.6 g, 30 mmol) for 16 h at 25° C. A solution of sodium bicarbonate (1 mL of 10 M) was added and the mixture evaporated to dryness. The residue was partitioned between ethyl acetate (100 mL) and water (25 mL). The organic phase was dried with magnesium sulfate and evaporated to dryness. The solid was dissolved in tetrahydrofuran (20 mL) and stirred with tetrabutyl ammonium fluoride in tetrahydrofuran (20 mL of a 1 M solution) for 1 h in a dry ice/acetone bath. Removal of the solvent in vacuo followed by washing with hexane afforded the 5'-alcohol (5.3 g).

A portion of the above phenylurea product (0.41 g, 0.96 mmol) was suspended in 25 mL of 20% aqueous acetic acid and 5 mL of tetrahydrofuran/dioxane (1:1) and was stirred at 50° C. for 24 h. The white suspension became a clear yellow solution. The mixture was concentrated and then lyophilized, to give 0.360 g (97% yield) of 1-[9-(3,4-dihydroxy-5-hydroxymethyl-tetrahydro-furan-2-yl)-9H-purin-6-yl]-3-phenyl-urea as a yellow solid. MW calculated for $C_{17}H_{18}N_6O_5$ (MH$^+$) 387, found 387 by LCMS.

A small amount of 4A flame dried molecular sieves (cooled down by a flow of argon) was added to a vial containing a portion of the product immediately above (0.131 g, 0.34 mmol). The mixture was capped with a rubber septum and cooled down to 0° C. To this mixture trifluoroacetic acid (2.5 mL) was added via syringe and the mixture stirred at this temperature for 15 min. Phenyl acetaldehyde dimethylacetal (0.230 ml, 4 eq.) was added dropwise and the mixture stirred at 0° C. for 2 h. One more equivalent of phenyl acetaldehyde dimethyl acetal was added and stirred an additional five hours. The volatiles were evaporated off and the residue was purified by flash chromatography (hexane:ethyl acetate, 8:2, 1% triethylamine) to give 0.095 g of product (60% yield) as a yellow solid. MW calculated for $C_{25}H_{24}N_6O_5$ (MH$^+$) 489, found 489 by LCMS.

A portion of this acetal product (0.068 g, 0.14 mmol) was dissolved in dry N,N-dimethyl formamide (2.5 mL) and potassium tert-butoxide (0.084 g, 5 eq) was added to give a yellow solution. To this mixture was added 2-fluoro-5-nitrobenzoic acid (0.046 g, 1.8 eq). After 2.5 h of stirring at room temperature the mixture was concentrated and purified by preparative HPLC to give the nucleoside analog as a white powder. MW calculated for $C_{32}H_{27}N_7O_9$ (MH$^+$) 654, found 654 by LCMS.

The nitro group of the product immediately above was reduced under a hydrogen atmosphere with a catalytic amount of 10% Pd/C in methanol during 6 h. Filtration through Celite followed by HPLC purification yielded 52 mg (62% yield) of the title compound as clear semisolid.

Example 2

Preparation of 5'-heteroaryl ether derivatives

2-{2,2-Dimethyl-6-[6-(3-phenyl-ureido)-purin-9-yl]-tetrahydro-furo [3,4-d][1,3]dioxol-4-ylmethoxy}-nicotinic acid To a stirred solution of 1-[9-(6-hydroxymethyl-2,2-dimethyl-tetrahydro-furo[3,4-d][1,3]dioxol-4-yl)-9H-purin-6-yl]-3-phenyl-urea (43 mg, 0.1 mmol) in dry N, N'-dimethylformamide (1 mL) at 23° C. was added potassium tert-butoxide (45 mg, 0.4 mmol). After 30 min, 2-chloronicotinic acid (60 mg, 0.4 mmol) was added to the solution. The resulting mixture was stirred at 23° C. for 15 h and then quenched with water (1 mL), suspended in ethyl acetate (50 mL), washed with brine (3×), dried over anhydrous sodium sulfate, filtered and concentrated in vacuo to give the crude product. Preparative reverse-phase HPLC was used to obtain the pure compound (15 mg, 27% yield) as a white solid. $^1$H NMR (300 MHz, DMSO-d$_6$) δ 11.76 (s, 1H), 10.15 (s, 1H), 9.16 (s, 1H), 8.65 (s, 1H), 8.05 (dd, J=8.5 Hz, 3.5 Hz, 1H), 7.94 (dd, J=9.0 Hz, 3.0 Hz, 1H), 7.60 (d, J=2.0 Hz, 1H), 7.57 (d, J=2.0 Hz, 1H), 7.32 (t, J=12.5 Hz, 2H), 7.05 (t, J=12.5 Hz, 1H), 6.96 (dd, J=12.5 Hz, 8.5 Hz, 1H), 6.25 (d, J=6.0 Hz, 1H), 5.80 (t, J=7.5 Hz, 1H), 5.10 (dd, J=9.0 Hz, 2.5 Hz, 1H), 4.67 (m, 1H), 4.53 (dd, J=20.0 Hz, 4.0 Hz, 1H), 4.36 (dd, J=20.0 Hz, 4.0 Hz, 1H), 1.59 (s, 3H), 1.38 (s, 3H). MW calculated for $C_{26}H_{25}N_7O_7$ (MH$^+$) 548, found 548 by LCMS.

Similarly, other 5'-substituted pyridines were prepared:

6-{2,2-Dimethyl-6-[6-(3-phenyl-ureido)-purin-9-yl]-tetrahydro-furo[3,4-d][1,3]dioxol-4-ylmethoxy}-nicotinic acid: (9 mg, 8% yield) as a white solid. $^1$H NMR (300 MHz, DMSO-d$_6$) δ 11.68 (s, 1H), 10.20 (s, 1H), 8.71 (s, 1H), 8.64 (d, J=3.0 Hz, 2H), 8.12 (dd, J=15.0 Hz, 3.5 Hz, 1H), 7.63 (d, J=2.0 Hz, 1H), 7.61 (d, J=1.5 Hz, 1H), 7.36 (t, J=13.0 Hz, 2H), 7.09 (t, J=12.5 Hz, 1H), 6.84 (dd, J=13.5 Hz, 1.0 Hz, 1H), 6.33 (d, J=3.5 Hz, 1H), 5.61 (dd, J=10.0 Hz, 4.0 Hz, 1H), 5.20 (dd, J=10.0 Hz, 4.5 Hz, 1H), 4.64 (m, 1H), 4.54 (m, 2H), 1.60 (s, 3H), 1.40 (s, 3H). MW calculated for $C_{26}H_{25}N_7O_7$ (MH$^+$) 548, found 548 by LCMS.

6-{2,2-Dimethyl-6-[6-(3-phenyl-ureido)-purin-9-yl]-tetrahydro-furo[3,4-d][1,3]dioxol-4-ylmethoxy}-pyridine-2-carboxylic acid: (5 mg, 4.6% yield) as a white solid. $^1$H NMR (300 MHz, DMSO-d$_6$) δ 11.64 (s, 1H), 10.15 (s, 1H), 8.68 (s, 1H), 8.60 (s, 1H), 7.83 (dd, J=13.5 Hz, 12.5 Hz, 1H), 7.62 (m, 3H), 7.34 (t, J=12.5 Hz, 2H), 7.06 (t, J=12.5 Hz, 1H), 6.96 (dd, J=13.0 Hz, 1.0 Hz, 1H), 6.30 (d, J=4.0 Hz, 1H), 5.59 (dd, J=10.0 Hz, 4.5 Hz, 1H), 5.17 (dd, J=10.0 Hz, 4.5 Hz, 1H), 4.64 (m, 1H), 4.50 (m, 2H), 1.58 (s, 3H), 1.38 (s, 3H). MW calculated for $C_{26}H_{25}N_7O_7$ (MH$^+$) 548, found 548 by LCMS.

5-Chloro-6-{2,2-dimethyl-6-[6-(3-phenyl-ureido)-purin-9-yl]-tetrahydro-furo[3,4-d][1,3]dioxol-4-ylmethoxy}-nicotinic acid: (11 mg, 1.5% yield) as a white solid. MW calculated for $C_{26}H_{24}ClN_7O_7$ (MH$^+$) 582, found 582 by LCMS.

6-Chloro-2-{2,2-dimethyl-6-[6-(3-phenyl-ureido)-purin-9-yl]-tetrahydro-furo[3,4-d][1,3]dioxol-4-ylmethoxy}-nicotinic acid (isomer A) & 2-Chloro-6-{2,2-dimethyl-6-[6-(3-phenyl-ureido)-purin-9-yl]-tetrahydro-furo[3,4-d][1,3]dioxol-4-ylmethoxy}-nicotinic acid (isomer B):

Two isomer were obtained from the reaction with 2,6-dichloronicotinic acid. The major product was A (80 mg, 69% yield). LC-MS calculated for $C_{26}H_{24}ClN_7O_7$ (MH$^+$) 582, found 582. The minor product was B (20 mg, 17% yield). MW calculated for $C_{26}H_{24}ClN_7O_7$ (MH$^+$) 582, found 582 by LCMS.

2-Chloro-6-{2,2-dimethyl-6-[6-(3-phenyl-ureido)-purin-9-yl]-tetrahydro-furo[3,4-d][1,3]dioxol-4-ylmethoxy}-isonicotinic acid: (60 mg, 52% yield) as a white solid. $^1$H NMR (300 MHz, DMSO-d$_6$) δ 11.63 (s, 1H), 10.18 (s, 1H), 8.68 (s, 1H), 8.61 (s, 1H), 7.6 (s, 1H), 7.59 (s, 1H), 7.36 (s, 1H), 7.33 (t, J=13.0 Hz, 2H), 7.06 (t, J=13.5 Hz, 1H), 6.29 (d, J=3.5 Hz, 1H), 5.63 (dd, J=10.0 Hz, 4.0 Hz, 1H), 5.17 (dd, J=10.0 Hz, 4.5 Hz, 1H), 4.64 (m, 1H), 4.47 (m, 2H), 1.60 (s, 3H), 1.38 (s, 3H). MW calculated for $C_{26}H_{24}ClN_7O_7$ (MH$^+$) 582, found 582 by LCMS.

6-{2,2-Dimethyl-6-[6-(3-phenyl-ureido)-purin-9-yl]-tetrahydro-furo[3,4][1,3]dioxol-4-ylmethoxy}-nicotinamide: (15 mg, 14% yield) as a white solid. $^1$H NMR (300 MHz, DMSO-d$_6$) δ 11.70 (s, 1H), 10.10 (s, 1H), 8.69 (s, 1H), 8.61 (s, 1H), 8.60 (d, J=4.0 Hz, 1H), 8.09 (dd, J=10.0 Hz, 4.0 Hz, 1H), 7.95 (s, 1H), 7.62 (s, 1H), 7.59 (s, 1H), 7.39 (s, 1H), 7.34 (t, J=15.0 Hz, 2H), 7.07 (t, J=12.5 Hz, 1H), 6.80 (d, J=14.0 Hz, 1.0 Hz, 1H), 6.31 (d, J=4.0 Hz, 1H), 5.59 (dd, J=10.5 Hz, 4.5 Hz, 1H), 5.17 (dd, J=10.0 Hz, 4.5 Hz, 1H), 4.63 (m, 1H), 4.49 (m, 2H), 1.59 (s, 3H), 1.39 (s, 3H). MW calculated for $C_{26}H_{26}N_8O_6$ (MH$^+$) 547, found 547 by LCMS.

6-Chloro-2-{2,2-dimethyl-6-[6-(3-phenyl-ureido)-purin-9-yl]-tetrahydro-furo[3,4-d][1,3]dioxol-4-ylmethoxy}-5-fluoro-nicotinic acid: (35 mg, 19% yield) as a white solid. MW calculated for $C_{26}H_{23}ClFN_7O_7$ (MH$^+$) 600, found 600 by LCMS.

1-{9-[6-(3-Hydroxy-pyridin-2-yloxymethyl)-2,2-dimethyl-tetrahydro-furo[3,4-d][1,3]dioxol-4-yl]-9H-purin-6-yl}-3-phenyl-urea Dry argon was bubbled through a solution of 1-{9-[6-(3-Benzyloxy-pyridin-2-yloxymethyl)-2,2-dimethyl-tetrahydro-furo[3,4-d][1,3]dioxol-4-yl]-9H-purin-6-yl}-3-phenyl-urea (18 mg, 0.03 mmol, prepared as above) in methanol/ethyl acetate (1:1 v/v, 10 mL) at 23° C. for 10 min. Palladium on activated carbon (10%) was added and the suspension was degassed by argon for another 5 min. Hydrogen (H$_2$) was conducted to the solution via a balloon, and the reaction proceeded for 5 h. The mixture was filtered and concentrated in vacuo to give the crude product. Preparative reverse-phase HPLC was used to obtain the pure compound (5 mg, 31% yield) as a white solid. MW calculated for $C_{25}H_{25}N_7O_6$ (MH$^+$) 520, found 520 by LCMS.

2-{2-Benzyl-6-[6-(3-phenyl-ureido)-purin-9-yl]-tetrahydro-furo[3,4-d][1,3]dioxol-4-ylmethoxy}-nicotinic acid 2-{2,2-Dimethyl-6-[6-(3-phenyl-ureido)-purin-9-yl]-tetrahydro-furo[3,4-d][1,3]dioxol-4-ylmethoxy}-nicotinic acid (180 mg, 0.33 mmol) was dissolved in a mixture of trifluoroacetic acid and water (TFA/H$_2$O, 4:1 v/v, 20 mL), and the suspension was stirred at 23° C. for 30 min. The solvents were removed under reduced pressure to give the intermediate diol product (120 mg, 72% yield) as a white solid. MW calculated for $C_{23}H_{21}N_7O_7$ (MH$^+$) 508, found 508 by LCMS.

To a stirred solution of the diol immediately above (0.23 mmol) in dry trifluoroacetic acid (5 mL) at 23° C. was added phenyl acetaldehyde (130 mg, 1.1 mmol). The resulting mixture was stirred at 23° C. for 6 h. After the removal of most trifluoroacetic acid by evaporation under reduced pressure, the reaction was quenched with saturated sodium bicarbonate solution (10 mL). The product was extracted using ethyl acetate (50 mL), washed with brine (3×), dried over anhydrous sodium sulfate, filtered and concentrated in vacuo to give the crude product. Preparative reverse-phase HPLC was used to obtain the pure acetal compound (7 mg, 5% yield) as a white solid. $^1$H NMR (300 MHz, DMSO-d$_6$) δ 11.67 (s, 1H), 10.50 (s, 1H), 8.68 (s, 1H), 8.51 (s, 1H), 8.27 (dd, J=8.0 Hz, 3.0 Hz, 1H), 8.10 (dd, J=10.0 Hz, 4.0 Hz, 1H), 7.60 (dd, J=14.0 Hz, 2.0 Hz, 1H), 7.30 (m, 7H), 7.08 (m, 3H), 6.21 (d, J=4.5 Hz, 1H), 5.51 (dd, J=10.5 Hz, 4.0 Hz, 1H), 5.32 (t, J=8.0 Hz, 1H), 5.06 (dd, J=10.0 Hz, 3.0 Hz, 1H), 4.70 (m, 1H), 4.62 (dd, J=20.0 Hz, 5.0 Hz, 1H), 4.45 (dd, J=20.0 Hz, 5.0 Hz, 1H), 3.10 (d, J=8.5 Hz, 2H). MW calculated for $C_{31}H_{27}N_7O_7$ (MH$^+$) 610, found 610 by LCMS.

Other 5'-substituted pyridine-ethers were transformed to various 2',3'-acetals using methods similar to those given immediately above.

Example 3

Synthesis of 5'-isoxazole Derivatives

3-[6-(6—Chloro-purin-9-yl)-2,2-dimethyl-tetrahydro-furo[3,4-d][1,3]dioxol-4-ylmethoxy]-isoxazole-5-carboxylic acid methyl ester To a solution of [6-(6—Chloro-purin-9-yl)-2,2-dimethyl-tetrahydro-furo[3,4-d][1,3]dioxol-4-yl]-methanol (0.570 g, 1.74 mmol) in 16 mL of dry dichloromethane was added polymer-bound triphenylphosphine (PS-TPP; Argonaut Tech., 2.14 mmol/g, 0.91 g, 1.2 eq), followed by methyl-3-hydroxy-5-isoxazolecarboxylate (0.248 g, 1 eq). The mixture was sonicated for 15 minutes then stirred at room temperature for 1 h under argon. The reaction mixture was cooled to 0° C. and under argon flow diethylazodicarboxylate (0.33 g, 1.1 eq), dissolved in 1 ml of dichloromethane, was added dropwise via syringe. The mixture was protected from light and stirred at 0° C. for 30 min. then at room temperature for 20 h. The resin was washed liberally with dichloromethane and methanol. The organic solution obtained from the washes was concentrated to give, after flash chromatography purification, 0.740 g of the product as a white solid (95% yield). $^1$H NMR (300 MHz, CDCl$_3$) δ 8.76 (s, 1H), 8.23 (s, 1H), 6.42 (s, 1H), 6.23 (d, J=2.1 Hz, 1H), 5.43 (dd, J=2.1 Hz, 1H), 5.14 (dd, J=3.6 Hz, 1H), 4.7 (m, 1H), 4.61 (dd, J=3.9 Hz, 1H), 4.49 (dd, J=5.7 Hz, 1H), 3.93 (s, 3H), 1.65 (s, 3H), 1.42 (s, 3H). MW calculated for $C_{18}H_{18}ClN_5O_7$ (MH$^+$) 452, found 452 by LCMS.

3-{6-[6-(N-Benzyl-N-methyl-amino)-purin-9-yl]-2,2-dimethyl-tetrahydro-furo[3,4-d][1,3]dioxol-4-ylmethoxy}-isoxazole-5-carboxylic acid To a solution of 3-[6-(6-Chloro-purin-9-yl)-2,2-dimethyl-tetrahydro-furo[3,4-d][1,3]dioxol-4-ylmethoxy]-isoxazole-5-carboxylic acid methyl ester (0.106 g, 0.23 mmol) in tetrahydrofuran (1.2 mL) was added polymer-bound diisopropylethylamine (PS-DIEA; Argonaut Tech., 3.83 mmol/g, 0.190 g, 3 eq), followed by addition of 0.040 mL of N-methyl-N-benzylamine (1.2 eq). The resulting mixture was stirred at room temperature overnight. The PS-DIEA resin was washed three times with dichloromethane and the solution obtained from the washes was concentrated to yield 3-{6-[6-(N-Benzyl-N-methyl-amino)-purin-9-yl]-2,2-dimethyl-tetrahydro-furo[3,4-d][1,3]dioxol-4-ylmethoxy}-isoxazole-5-carboxylic acid methyl ester as yellow oil. This material (0.23 mmol) was dissolved in 1,4-dioxane (1.2 mL) and 0.250 mL of an aqueous 2M lithium hydroxide solution added. The mixture was stirred at room temperature for 4 h. The crude product, isolated after acid workup, was used without further purification in the following step. MW calculated for $C_{25}H_{26}N_6O_7$ (MH$^+$): 523, found 523 by LCMS.

3-{2-Benzyl-6-[6-(N-methyl-N-benzyl-amino)-purin-9-yl]-tetrahydro-furo[3,4-d][1,3]dioxol-4-ylmethoxy}-isoxazole-5-carboxylic Acid A solution of the above acetonide (0.075 g, 0.140 mmol) dissolved in 1.5 mL of dry dichloromethane was cooled in an ice bath to 0° C. To this clear mixture was added 1.8 mL of trifluoroaceic acid. The mixture was stirred at 0° C. for 5 h to afford the intermediate diol as a yellow semisolid after evaporative workup. This crude product (0.23 mmol) was dissolved at 0° C. in 1 mL of dry trifluoroacetic acid in the flask. To this mixture was added a small amount of 3A molecular sieves (previously dried by flame in situ and cooled by a stream of argon). The flask was capped with a rubber septum and cooled to 0° C., then 0.1 mL of phenyl acetaldehyde dimethyl acetal was added and the mixture stirred for 18 h at 0° C. At that point, 0.1 mL more of acetal was added and stirred an additional 6 h. Purification by HPLC yielded 52 mg of the desired product as a clear semisolid (62% yield). MW calculated for $C_{30}H_{28}N_6O_7$ (MH$^+$): 585, found 585 by LCMS.

The following acetonide-isoxazolecarboxylic acid analogs were prepared in a similar manner to the chloride displacement/hydrolysis sequence described above, using different amines:

Amine Used; Product Data:
N-trans-(cyclopropylphenyl)amine; Calculated mass for product (LCMS): $C_{26}H_{26}N_6O_7$ (MH$^+$): 535, found: 535.
N-Methyl-N-Phenethylamine; Calculated mass for product (LCMS): $C_{26}H_{28}N_6O_7$ (MH$^+$): 537, found: 537.
Phenethylamine; Calculated mass for product (LCMS): $C_{25}H_{26}N_6O_7$ (MH$^+$): 523, found: 523.
Benzylamine; Calculated mass for product (LCMS): $C_{24}H_{24}N_6O_7$ (MH$^+$): 509, found: 509.
Isobutylamine; Calculated mass for product (LCMS): $C_{21}H_{26}N_6O_7$ (MH$^+$): 475, found: 475.
Cyclopentylamine; Calculated mass for product (LCMS): $C_{22}H_{26}N_6O_7$ (MH$^+$): 487, found: 487.
N-(Methylthiophene-yl)amine; Calculated mass for product (LCMS): $C_{22}H_{22}N_6O_7S$ (MH$^+$): 515 found: 515.
5-Methylfurfurylamine; Calculated mass for product (LCMS): $C_{23}H_{24}N_6O_8$ (MH$^+$): 513, found: 513.
Propylamine; Calculated mass for product (LCMS): $C_{20}H_{24}N_6O_7$ (MH$^+$): 461, found: 461.
Aminopropylimidazole; Calculated mass for product (LCMS): $C_{23}H_{26}N_8O_7$ (MH$^+$): 527, found: 527.
3-Methylaminopyridine; Calculated mass for product (LCMS): $C_{23}H_{23}N_7O_7$ (MH$^+$): 510, found: 510.
Aminoethylpyrrolidine; Calculated mass for product (LCMS): $C_{23}H_{29}N_7O_7$ (MH$^+$): 516, found: 516.
Aniline; Calculated mass for product (LCMS): $C_{23}H_{22}N_6O_7$ (MH$^+$): 495, found: 495.

Example 4

Solution Phase Synthesis of 5'-carboxamide adenosine analogs 2',3'-O-Isopropylideneadenosine-5'-carboxylic acid In a reaction vessel, bis-acetoxyiodobenzene (BAIB, 1.15 g, 3.58 mmol), 2,2,6,6-tetramethyl-1-piperidinyloxy (TEMPO, 0.051 g, 0.325 mmol), and 2',3'-isopropylideneadenosine (0.500 g, 1.63 mmol) were combined, and 3 mL of 1:1 acetonitrile:water mixture was added to the reaction vessel. The reaction mixture was stirred at ambient temperature under argon for 1 h then filtered. The white crystalline product was washed with acetonitrile:water mixture (1:1) and dried in vacuo, to yield 0.464 g of product, 89%. $^1$H NMR (300 MHz, CD$_3$SOCD$_3$) δ 12.77 (br s, 1H), 8.22 (s, 1H), 8.06 (s, 1 H), 7.27 (s, 2 H), 6.32 (s, 1H), 5.52 (dd, J1=5.7 Hz, J2=1.8 Hz, 1H), 5.45 (d, J=9.5 Hz, 1H), 4.67 (d, J=1.5 Hz, 1H), 1.52 (s, 3H), 1.35 (s, 3H).

2-({2,2-Dimethyl-6-[6-(3-phenyl-ureido)-purin-9-yl]-tetrahydro-furo[3,4-d][1,3]dioxole-4-carbonyl}-amino)-benzoic acid methyl ester To a vial containing 2',3'-O-Isopropylideneadenosine-5'-carboxylic acid (0.241 g, 0.75 mmol) was added 3-aminobenzoic acid methyl ester (0.144 g, 0.75 mmol) in one portion at RT followed by heating at 50° C. overnight. The reaction mixture was diluted with 100 ml of ethyl acetate, washed with 1N hydrochloric acid, saturated sodium bicarbonate, brine, and dried over MgSO$_4$. Upon removal of solvent, the solid residue was purified with chromatography with 2-5% methanol in dichloromethane to give 90 mg (26%) of the carboxamide as white solid. MW calculated for C$_{21}$H$_{22}$N$_6$O$_6$ (MH$^+$) 455, found 455 by LCMS. This carboxamide product (90 mg, 0.20 mmol) was dissolved in DMF (2 mL) and added to a flask containing phenyl isocyanate (35 mg, 0.30 mmol) in 2 ml of toluene at 50° C. The reaction was stirred at 50° C. overnight. Additional phenyl isocyanate (35 mg, 0.20 mmol) was then added in several portions until nearly complete consumption of the starting material was noted by TLC analysis. The reaction mixture was then diluted with ethyl acetate (100 ml), washed with saturated sodium bicarbonate, brine, and dried over magnesium sulfate. The crude product was purified by a chromatography with 0-2% methanol in dichloromethane to give 57 mg (50%) of pure product and recovered starting material (10 mg). $^1$H NMR (300 MHz, CDCl$_3$) δ 11.53 (s, 1H), 9.21 (s, 1H), 8.54 (s, 1H), 8.36 (s, 1H), 8.21 (s, 1H), 7.72 (m, 1H), 7.58 (m, 2H), 7.38 (m, 2H), 7.24 (m, 1H), 7.12 (m, 1H), 6.29 (d, J=2.1 Hz, 1H), 5.66 (dd, J=6.3, 1.5 Hz, 1H), 5.56 (dd, J=6.3, 1.5 Hz, 1H), 4.88 (d, J=1.8 Hz, 1H), 3.78 (s, 3H), 1.65 (s, 3H), 1.44 (s, 3H). MW calculated for C$_{28}$H$_{27}$N$_7$O$_7$ (MH$^+$): 574, found 574 by LCMS.

3-({2,2-Dimethyl-6-[6-(3-phenyl-ureido)-purin-9-yl]-tetrahydro-furo[3,4-d][1,3]dioxole-4-carbonyl}-amino)-benzoic acid To a vial containing 2',3'-O-Isopropylideneadenosine-5'-carboxylic acid (250 mg, 0.778 mmol), triethylamine (1.57 mg, 1.56 mmol), and 3-amino-benzoic acid allyl ester (0.276 mg, 1.56 mmol) in 0.5 ml of N,N-dimethyl formamide at 0° C. was added PyBOP (0.443 mg, 0.856 mmol) in one portion. Reaction was continued at 0° C. for 4 h and at ambient for 4 h. Additional PyBOP (50 mg) was added and the reaction continued overnight at ambient temperature. The reaction mixture was diluted with ethyl acetate (100 ml), washed with saturated sodium bicarbonate, brine, and dried over magnesium sulfate. The crude was purified by a chromatography with 0-2% methanol in dichloromethane to give the desired amide product. MW calculated for C$_{23}$H$_{24}$N$_6$O$_6$ (MH$^+$) 481, found 481 by LCMS.

Phenyl isocyanate was coupled with the amide product using a method similar to those described above, affording the intermediate phenylurea compound. MW calculated for C$_{30}$H$_{29}$N$_7$O$_7$ (MH$^+$) 600, found 600 by LCMS.

This phenylurea compound (36 mg, 0.057 mmol) and morpholine (0.015 mg, 0.17 mmol) were dissolved in tetrahydrofuran (5 ml) followed by addition of tetrakis(triphenylphosphine)palladium (5 mg, 0.004 mmol). Reaction was completed in 4 h at RT. After removal of the solvent, the crude product mixture was purified by preparative HPLC to give the desired product. $^1$H NMR (300 MHz, CDCl$_3$) δ 11.52 (s, 1H), 9.99 (s, 1H), 9.60 (s, 1H), 8.61 (s, 1H), 8.42 (s, 1H), 7.94 (s, 1H), 7.72 (m, 4H), 7.34 (m, 2H), 7.23 (m, 1H), 7.06 (m, 1H), 6.56 (s, 1H), 5.56 (m, 2H), 4.88 (s, 1H), 1.58 (s, 3H), 1.39 (s, 3H).

Example 5

Solution Phase Synthesis of a Sulfonamide

N-{2,2-Dimethyl-6-[6-(3-phenyl-ureido)-purin-9-yl]-tetrahydro-furo[3,4-d][1,3]dioxole-4-carbonyl}-methanesulfonamide To a vial containing 2',3'-O-Isopropylideneadenosine-5'-carboxylic acid (20 mg, 0.045 mmol), dimethylaminopyridine (5 mg, 0.045 mmol), and methanesulfonamide (0.009 mg, 0.091 mmol) in dichloromethane (0.5 ml) was added dicyclohexylcarbodiimide (10 mg, 0.05 mmol). The mixture was stirred for 2 days at RT. Additional dicyclohexylcarbodiimide (10 mg, 0.05 mmol) and dimethylaminopyridine (5 mg, 0.045 mmol) were added and the reaction was continued at RT overnight. To the reaction mixture was added ethyl acetate (75 ml), which was washed with 1 N hydrochloric acid, water, saturated sodium bicarbonate, brine, and dried over magnesium sulfate. Upon removal of solvent, the residue was purified by prep. HPLC to yield 13 mg of desired product (55%). MW calculated for C$_{21}$H$_{23}$N$_7$O$_7$S (MH$^+$) 518, found 518 by LCMS.

Example 6

Solid Phase Synthesis of Ureas and Acetals from Polymer Bound 5'-proline-amides of adenosine Commercially available hydroxymethylsulfanylmethyl (HESM) polystyrene resin (1.4 mmol/g, 200 mesh, NovaBiochem; 2.82 g, 3.95 mmol) was swelled for 15 minutes in 50 mL. In a separate reaction vessel, Boc-Pro-OH (3.40 g, 15.8 mmol), HATU (5.7 g, 15.0 mmol), dimethylaminopyridine (0.24 g, 1.98 mmol), and diisopropylethylamine (3.5 mL, 19.8 mmol) were dissolved in 40 mL of N,N-dimethyl formamide and stirred for 15 minutes. N,N-dimethyl formamide was drained from the HESM resin and the solution of activated proline derivative was added to the resin. The resin was agitated at RT for 17 h. The solvent was then drained and the resin washed with N,N-dimethyl formamide (3×30 mL), dichloromethane (3×30 mL), methanol (3×30 mL), dichloromethane (2×30 mL), methanol (3×30 mL) and dried in vacuo overnight. Mass of resin: 3.42 g, 93% loading.

Removal of BOC Protecting Group:

Resin obtained in the previous step was agitated with a 40% trifluoroacetic acid/dichloromethane solution (75 mL) for 15 minutes. The solvent was drained, and a fresh solution of 40% trifluoroacetic acid in dichloromethane was added, and resin was agitated for another 15 minutes. After this the resin was washed with dichloromethane (5×40 mL), 20% diisopropylethylamine/dichloromethane (2×30 mL), dichloromethane (3×30 mL), and methanol (5×40 mL). The resin was dried under vacuum. A chloranil test indicated the presence of a free amino group, and this proline-bound resin was carried over to the next step.

The proline resin product from the previous step was swelled in 50 mL N,N-dimethyl formamide for 30 minutes, after that the N,N-dimethyl formamide was drained. In a separate reaction vessel, 2',3'-O-Isopropylideneadenosine-5'-carboxylic acid (1.40 g, 4.35 mmol), dichloroethane (0.91 g, 4.74 mmol), HOBt·$H_2O$ (0.73 g, 4.74 mmol), and diisopropylethylamine (3.5 mL, 19.8 mmol) were dissolved in 55 mL of N,N-dimethyl formamide. The solution was stirred for 15 minutes, and then added to the proline resin. The resin was agitated at RT for 17 h. The solvent was drained, the resin was washed with N,N-dimethyl formamide (3×30 mL), dichloromethane (3×30 mL), methanol (3×30 mL), dichloromethane (2×30 mL), methanol (3×30 mL), and dried in vacuo for 48 h. A chloranil test performed on a few sample beads indicated that coupling had occurred. A small amount of resin was cleaved using the following procedure to verify attachment of the carboxylic acid, and analysed by LCMS. Calculated mass for $C_{18}H_{22}N_6O_6$ ($MH^+$): 419, found 419 by LCMS. Mass of resin: 3.66 g, 0.55 mmol/g, 82% in three steps.

General Cleavage Procedure for Analysis of HESM Resin:

A small amount of resin is suspended in a solution of 5-6 equivalents of m-chloroperbenzoic acid in dichloromethane and agitated for 7-8 hours at RT. The solution is then drained, and the resin is washed 5-6 times with fresh dichloromethane. Then resin is suspended in a solution of 4-5 equivalents of DBU in dichloromethane, and agitated at RT for 4-5 hours. The resin is then filtered and the solution is analyzed by LC/MS, HPLC or another method. The compounds are recovered from solution by rotary evaporation.

The adenosine-proline amide-derivatized resin from the previous resin-synthesis step (0.5 g, 0.275 mmol) was suspended in anhydrous N,N-dimethyl formamide (10 mL). Ethyl isocyanate was added (0.43 mL, 5.5 mmol), and the reaction mixture was heated in a capped vial at 55° C. for 16 h. The resin was then drained and washed with N,N-dimethyl formamide (3×10 mL), dichloromethane (3×10 mL), methanol (3×10 mL), dichloromethane (2×10 mL), methanol (3×10 mL), and the procedure was repeated once again then the resin dried in vacuo for 24 h. A negative chloranil test indicated complete reaction. A small amount of this resin (bound to the 5'-adenosine-(2',3'-acetonide)-proline amide-derivatized as the 6-ethylurea) was cleaved by the procedure described for cleavage of HESM resin, and the isolated product was analyzed by LCMS. Mass calculated for $C_{21}H_{27}N_7O_7$ ($MH^+$): 490, found 490 by LCMS. Loading 0.52 mmol/g, mass 0.52 g, 98%.

The procedure described above was also used to prepare $N^6$-ureas with $R_d$=—$C_6H_{11}$, —Ph, —$CH_2Ph$, —$CH_2CH_2Ph$, -cyclopentyl, and trans-2-phenyl-cycloprop-1-yl groups using the appropriate isocyanates.

1-{6-[6-(3-Ethyl-ureido)-purin-9-yl]-2-phenyl-tetrahydro-furo[3,4-d][1,3]dioxol-4-carbonyl}-pyrrolidine-2-carboxylic acid The resin described above (0.05 g, 0.026 mmol) was suspended in trifluoroacetic acid, then benzaldehyde (0.095 g, 0.9 mmol) was added all at once. The resin was agitated in a tightly closed vial for 24 h. The resin was drained, washed with dichloromethane (5×3 mL), 20% diisopropylethylamine/dichloromethane (2×3 mL), dichloromethane (3×3 mL), and methanol (5×3 mL), then dried in vacuo for 3 h. The resin was cleaved using the cleavage procedure described above, the crude product was collected, analyzed by LCMS and purified by preparative HPLC. Calculated MW for $C_{25}H_{27}N_7O_7$ ($MH^+$): 538, found: 538 by LCMS.

The following analogs were prepared in a similar manner to that described above, using appropriate combinations of isocyanates and aldehydes. Compounds analyzed by LCMS.

$R_d$=ethyl, $R_a$=benzyl Calculated MW for C26H29N7O7: 552.55 (MH+), found: 552.4.

$R_d$=ethyl, $R_a$=4-biphenyl Calculated MW for C31H31N7O7: 614.62 (MH+), found: 614.3

$R_d$=ethyl, $R_a$=3-biphenyl Calculated MW for C3 1H3 1N7O7: 614.62 (MH+), found: 614.3

$R_d$=ethyl, $R_a$=2-naphthyl Calculated MW for C29H29N7O7: 588.58 (MH+), found: 588.1.

$R_d$=n-hexyl, $R_a$=phenyl Calculated MW for C29H35N7O7: 594.63 (MH+), found: 594.3.

$R_d$=n-hexyl, $R_a$=benzyl Calculated MW for C30H37N7O7: 608.65 (MH+), found: 608.2.

$R_d$=n-hexyl, $R_a$=4-biphenyl Calculated MW for C35H39N7O7: 670.73 (MH+), found: 670.3.

$R_d$=n-hexyl, $R_a$=3-biphenyl Calculated MW for C35H39N7O7: 670.73 (MH+), found: 670.3.

$R_d$=n-hexyl, $R_a$=2-naphthyl Calculated MW for C33H37N7O7: 644.69 (MH+), found: 644.3.

$R_d$=cyclopentyl, $R_a$=benzyl Calculated MW for C29H33N7O7: 592.62 (MH+), found: 592.3.

$R_d$=cyclopentyl, $R_a$=phenyl Calculated MW for C28H3 1N7O7: 578.59 (MH+), found: 578.3.

$R_d$=cyclopentyl, $R_a$=4-biphenyl Calculated MW for C34H35N7O7: 654.68 (MH+), found: 654.3.

$R_d$=cyclopentyl, $R_a$=3-biphenyl Calculated MW for C34H35N7O7: 654.68 (MH+), found: 654.3.

$R_d$=cyclopentyl, $R_a$=2-naphthyl Calculated MW for C32H33N7O7: 628.65 (MH+), found: 628.4.

$R_d$=benzyl, $R_a$=benzyl Calculated MW for C31H31N7O7: 614.62 (MH+), found: 614.3.

$R_d$=benzyl, $R_a$=phenyl Calculated MW for C30H29N7O7: 600.59 (MH+), found: 600.3.

$R_d$=benzyl, $R_a$=2-naphthyl Calculated MW for C34H31N7O7: 650.65 (MH+), found: 650.3.

$R_d$=benzyl, $R_a$=4-biphenyl Calculated MW for C36H33N7O7: 676.69 (MH+), found: 676.3.

$R_d$=benzyl, $R_a$=3-biphenyl Calculated MW for C36H33N7O7: 676.69 (MH+), found: 676.3.

$R_d$=ethylphenyl, $R_a$=benzyl Calculated MW for C32H33N7O7: 628.65 (MH+), found: 628.4.

$R_d$=ethylphenyl, $R_a$=phenyl Calculated MW for C31H31N7O7: 614.62 (MH+), found: 614.5.

$R_d$=ethylphenyl, $R_a$=4-biphenyl Calculated MW for C37H35N7O7: 690.72 (MH+), found: 690.4.
$R_d$=ethylphenyl, $R_a$=3-biphenyl Calculated MW for C37H35N7O7: 690.72 (MH+), found: 690.5.
$R_d$=ethylphenyl, $R_a$=2-naphthyl Calculated MW for C35H33N7O7: 664.68 (MH+), found: 664.4.
$R_d$=cyclopropyl-trans-2-phenyl, $R_a$=benzyl Calculated MW for C33H33N7O7: 640.66 (MH+), found: 640.3.
$R_d$=cyclopropyl-trans-2-phenyl, $R_a$=3-biphenyl Calculated MW for C38H35N7O7: 702.73 (MH+), found: 702.6.
$R_d$=cyclopropyl-trans-2-phenyl, $R_a$=2-naphthyl Calculated MW for C36H33N7O7: 676.69 (MH+), found: 676.6.
$R_d$=phenyl, $R_a$=benzyl Calculated MW for C30H29N7O7: 600.59 (MH+), found: 600.3.
$R_d$=phenyl, $R_a$=phenyl Calculated MW for C29H27N7O7: 586.57 (MH+), found: 586.2.
$R_d$=phenyl, $R_a$=2-naphthyl Calculated MW for C33H29N7O7: 636.63 (MH+), found: 636.5.
$R_d$=phenyl, $R_a$=4-biphenyl Calculated MW for C35H31N7O7: 662.66 (MH+), found: 662.5.
$R_d$=phenyl, $R_a$=3-biphenyl Calculated MW for C35H31N7O7: 662.66 (MH+), found: 662.5.
$R_d$=phenyl, $R_a$=3-thianaphthene Calculated MW for C31H27N7O7S: 642.65 (MH+), found: 642.0.
$R_d$=ethylphenyl, $R_a$=3-thianaphthene Calculated MW for C33H31N7O7S: 670.71 (MH+), found: 670.0.
$R_d$=ethylphenyl, $R_a$=3-thianaphthene Calculated MW for C32H29N7O7S: 656.68 (MH+), found: 656.1.
$R_d$=n-hexyl, $R_a$=3-thianaphthene Calculated MW for C31H35N7O7S: 650.72 (MH+), found: 650.2.
$R_d$=n-hexyl, $R_a$=CHCHPh Calculated MW for C31H37N7O7: 620.67 (MH+), found: 620.4.
$R_d$=n-hexyl, $R_a$=CCPh Calculated MW for C31H35N7O7: 618.65 (MH+), found: 618.0.
$R_d$=cyclopropyl-trans-2-phenyl, $R_a$=CCPh Calculated MW for C34H31N7O7: 650.65 (MH+), found: 650.1.
$R_d$=ethylphenyl, $R_a$=CCPh Calculated MW for C33H31N7O7: 638.64 (MH+), found: 638.1.
$R_d$=benzyl, $R_a$=CCPh Calculated MW for C32H29N7O7: 624.62 (MH+), found: 624.1.
$R_d$=ethyl, $R_a$=CCPh Calculated MW for C27H27N7O7: 562.55 (MH+), found: 562.0.
$R_d$=cyclopropyl-trans-2-phenyl, $R_a$=4-biphenyl Calculated MW for C38H35N7O7: 702.73 (MH+), found: 702.1.
$R_d$=cyclopropyl-trans-2-phenyl, $R_a$=phenyl Calculated MW for C32H31N7O7: 626.63 (MH+), found: 626.0.
$R_d$=cyclopropyl-trans-2-phenyl, $R_a$=CHCHPh Calculated MW for C34H33N7O7: 652.67 (MH+), found: 652.1.
$R_d$=ethylphenyl, $R_a$=CHCHPh Calculated MW for C33H33N7O7: 640.66 (MH+), found: 640.3.

Example 7

(See Scheme 8) 1-[9-(2-Benzyl-6-ureidomethyl-tetrahydro-furo[3,4-d][1,3]dioxol-4-yl)-9H-purin-6-yl]-3-phenyl-urea methylsulfonamide In a reaction vessel were combined 2',3'-O-benzylidene-N[6]-(phenylurea)adenosine (0.200 g, 0.409 mmol), p-toluene sulfonyl chloride (0.148 g, 0.778 mmol), and 4.0 mL of pyridine. The mixture was stirred for 4 h at RT. The solvent was removed in vacuo and the tosylate (0.260 g, 99%) was recovered as a yellow solid. MW calculated for $C_{32}H_{30}N_6O_7S$: 643.19 (MH$^+$), found 642.9.

This tosylate product (0.260 g, 0.409 mmol) was dissolved in 3 mL of anhydrous N,N-dimethyl formamide, sodium azide (0.266 g, 4.09 mmol) was added, and the mixture was heated at 80° C. in a closed vial for 7 h while being stirred. The mixture was diluted with 50 mL of dichloromethane and extracted with 5% sodium bicarbonate solution and brine. The organic layer was separated, dried over anhydrous sodium sulfate and solvent was removed in vacuo. The azide derivative was recovered (0.183 g, 87%) as a white solid. MW calculated for $C_{25}H_{23}N_9O_4$: 514.19 (MH$^+$), found 514.1.

This residue containing the azide (0.180 g, 0.351 mmol) was dissolved in 6 mL of tetrahydrofuran/water mixture (18:1), polystyrene-bound triphenylphospine was added (2.19 mmol/g, 0.800 g, 1.75 mmol), and the reaction mixture was stirred at RT under argon for 24 h. The reaction mixture was then filtered, the solvent was removed in vacuo and the crude product was chomatographed on a silica gel column (2 cm×15 cm). The column was eluted with dichloromethane/methanol/triethylamine (88:10:2) to give 0.072 g (42%) of the amine as a white solid. MW calculated for $C_{25}H_{25}N_7O_4$: 488.20 (MH$^+$), found 488.0.

A portion of the amine product above (0.022 g, 0.046 mmol) was dissolved in 2 mL of dichloromethane (anhydrous) and methylsulfonylethylcarbamate (0.008 g, 0.046 mmol) was added. The reaction was stirred at RT under argon for 72 h. Solvent was then removed in vacuo, and the crude product was purified by preparative HPLC (acetonitrile/0.1% trifluoroacetic acid//water/0.1% trifluoroacetic acid buffer). 0.016 g (59%) of product was recovered as a white solid. MW calculated for $C_{27}H_{28}N_8O_7S$: 609.18 (MH$^+$), found 609.4. $^1$H NMR (300 MHz, CD$_3$SOCD$_3$) δ 11.69 (br s, 1 H), 10.22 (br s, 1 H), 8.69 (s, 1 H), 8.65 (s, 1 H), 7.60 (d, J=7.8 Hz, 2 H), 7.36-7.21 (m, 6 H), 7.07 (t, J=7.5 Hz, 1H), 6.90-6.87 (m, 1 H), 6.57 (s, 1 H), 6.22 (d, J=2.4 Hz, 1 H), 5.75 (s, 1 H), 5.45 (dd, J1=6.3 Hz, J2=2.1 Hz, 1 H), 5.31 (t, J=5.1 Hz, 1 H), 4.92 (dd, J1=6.6 Hz, J2=3.3 Hz, 1 H), 4.16-4.02 (m, 5 H), 3.11 (s, 3 H).

Example 8

5'-Homologated Derivatives as in Scheme 11

3-{2,2-Dimethyl-6-[6-(3-phenyl-ureido)-purin-9-yl]-tetrahydro-furo[3,4-d][1,3]dioxol-4-yl}-acrylic acid methyl ester To a vial containing the starting compound, 1-[9-(6-Hydroxymethyl-2,2-dimethyl-tetrahydro-furo[3,4-d][1,3]dioxol-4-yl)-9H-purin-6-yl]-3-phenyl-urea (1.07 g, 2.5 mmol), in 10 ml of dimethylsulfoxide was added IBX (1.06 g, 3.75 mmol) in one portion at RT. The white solid gradually dissolved as the reaction proceeded. After stirring at RT for 2 hours, methyl(triphenylphosphorylidene) acetate (0.84 g, 2.5 mmol) was added in one portion. The reaction was run at RT overnight. To the reaction mixture was added ethyl acetate (100 ml), which was washed with saturated NaHCO$_3$, brine, and dried over MgSO$_4$. After removal of solvent, the residue was recrystallized with isopropyl alcohol to provide the title compound. MW calculated for $C_{23}H_{24}N_6O_6$ (MH$^+$) 481.5 found 481.3 by LCMS.

3-{2,2-Dimethyl-6-[6-(3-phenyl-ureido)-purin-9-yl]-tetrahydro-furo[3,4-d][1,3]dioxol-4-yl}-propionic acid To a round bottom flask containing product from the previous step (1.2 g, 2.5 mmol) and palladium on carbon (10% w/w, 10 mg) under nitrogen was added methanol (20 ml). After flushing with hydrogen gas, the reaction mixture was stirred under a hydrogen atmosphere using a hydrogen balloon overnight at RT. Upon filtration and removal of solvent, the crude white solid product was recrystallized from isopropyl alcohol to give the desired methyl ester compound. MW calculated for $C_{23}H_{26}N_6O_6$ (MH$^+$) 483.5 found 483.2.

The methyl ester (500 mg, 1.04 mmol) was dissolved in 4 ml of methanol and sodium hydroxide (83 mg, 2.1 mmol) was then added. The reaction was stirred overnight at RT. After removal of methanol, acetic acid (2.1 mmol, 120 mmol) was added and a white solid precipitated. The solvent was removed under vacuum. The residue was recrystallized from water to provide the pure desired product as a white solid (0.4 g, 83%). MW calculated for $C_{22}H_{24}N_6O_6$ (M−1) 467.5 found 467.4 by LCMS.

1-(3-{2,2-Dimethyl-6-[6-(3-phenyl-ureido)-purin-9-yl]-tetrahydro-furo[3,4-d][1,3]dioxol-4-yl}-propion-1-yl)-pyrrolidine-2-carboxylic acid To a vial containing the carboxylic acid product from the previous step (0.117 g, 0.25 mmol), thionyl chloride (0.3 g, 2.5 mmol) was added at 0° C. After addition, the cold bath was removed followed by addition of two drops of N,N-dimethyl formamide. The reaction mixture was heated to 50° C. for 30 minutes. The excess of thionyl chloride was removed under vacuum and the solid residue was washed with ethyl ether to give the acid chloride. The acid chloride (61 mg, 0.125 mmol) was added to a vial containing L-proline methyl ester (23 mg, 0.138 mmol) and triethylamine (28 mg, 0.275 mmol) in 1 mL of dichloromethane at 0° C. The reaction was gradually warmed to RT overnight. To the reaction mixture was added ethyl acetate (75 ml), which was washed with 1 N hydrochloric acid, saturated sodium bicarbonate, and dried over magnesium sulfate. The residue was purified by elution from a silica column using 2% methanol in dichloromethane to give purified prolylmethyl ester product (10 mg, 14%). MW calculated for $C_{28}H_{33}N_7O_7$ (MH$^+$) 580.6 found 580.3 by LCMS. The prolylmethyl ester (6 mg, 0.010 mmol) was dissolved in tetrahydrofuran (0.1 ml) followed by addition of 6 μl of 15% sodium hydroxide. After stirring at RT for 2 hrs, ethyl acetate (50 ml) was added and enough 1 N hydrochloric acid was added to adjust the pH to 3. The organic layer was washed with brine and dried over magnesium sulfate. After removal of solvent, the title compound was obtained as a white powder. MW calculated for $C_{27}H_{31}N_7O_7$ (MH$^+$) 566.6 found 566.3 by LCMS.

Example 9

Enzymatic Synthesis of a Mixture of 1-Ethyl-3-[9-(6-hydroxymethyl-2-styryl-tetrahydro-furo[3,4-d][1,3]dioxol-4-yl)-9H-purin-6-yl]-urea isomers from the Corresponding isomeric Mixture of 5'-AMP acetal/urea Derivatives The 2',3'-(cinnamylacetal)-N$^6$-(ethylurea) derivative of AMP (0.750 g, 0.14 mmol) as a mixture of acetal diastereoisomers was dissolved in water (25 mL, 1.4 mol) in a round bottom flask and the pH was adjusted to 8.3 with NaOH. The temperature was adjusted to 35 C, and alkaline phosphatase (0.003 g, 0.00004 mol) was added. Within 15 minutes, the mixture became rather heterogenous, and methanol (20 mL, 0.5 mol) was added to resolubilize the nucleoside product. After 4 h the reaction was judged essentially complete by HPLC. The reaction was worked up by adding more MeOH (20 mL), heating to 60 C to denature the enzyme, and filtering through a 0.22 uM filter. The methanol was evaporated in vacuo, and a white, fine-particle solid precipitated from the remaining solvent. This mixture was cooled in an ice bath and filtered. Washing the material with water, followed by drying over $P_2O_5$ in a dessicator afforded the title product as a mixture of acetal diastereomers. Dry weight 440 mg (0.10 mmol, 71% yield).

Example 10

3-{6-[6-(3-Ethyl-ureido)-purin-9-yl]-2-styryl-tetrahydro-furo[3,4-d][1,3]dioxol-4-yl}-acrylic acid methyl ester 1-Ethyl-3-[9-(6-hydroxymethyl-2-styryl-tetrahydro-furo[3,4-d][1,3]dioxol-4-yl)-9H-purin-6-yl]-urea (5.0 g, 11 mmol) was suspended in dry acetonitrile (50 mL) and Dess-Martin periodinate (6.7 g, 16 mmol) was added. The suspension was stirred 2 h, after which time proton NMR of an aliquot showed complete conversion to the aldehyde. (Methoxycarbonylmethylene)triphenylphosphorane (3.9 g, 12 mmol) was added and stirring was continued overnight. The reaction mixture was then diluted with ethyl acetate (300 mL), washed with saturated sodium bicarbonate/thiosulfate solution (100 mL), dried with sodium sulfate and filtered. The filtrate was evaporated and the solid was dissolved in hot isopropyl alcohol (50 mL). It was allowed to cool, then heptane was added and it was stirred overnight. The resulting precipitate was washed with heptane and dried under vacuum, affording the desired product (2.9 g, 71%). $^1$H-NMR (300 MHz, d$_6$DMSO) δ1.15 (t, 3H, J=7 Hz), 3.21 (q, 2H, J=7 Hz), 3.59 (s, 3H), 4.98 (m, 1H), 5.28 (ψt, 1H, J=6 Hz), 5.51 (dd, 1H, J=6 Hz, <2 Hz), 5.70 (d, 1H, J=16 Hz), 5.90 (d, 1H, J=6 Hz), 6.30 (dd, 1H, J=6 Hz, 16 Hz), 6.45 (d, 1H, J<2 Hz), 6.95 (d, 1H, J=15 Hz), 7.35 (m, 3H), 7.45 (d, 2H, J=7 Hz), 8.50 (s, 1H), 8.60 (s, 1H), 9.30 (t, 1H, J=6 Hz), 9.60 (s, 1H).

Example 11

3-{6-[6-(3-Ethyl-ureido)-purin-9-yl]-2-styryl-tetrahydro-furo[3,4-d][1,3]dioxol-4-yl}-propionic acid methyl ester 3-{6-[6-(3-Ethyl-ureido)-purin-9-yl]-2-styryl-tetrahydro-furo[3,4-d][1,3]dioxol-4-yl}-acrylic acid methyl ester (250 mg, 0.5 mmol) was dissolved in dry methanol (3 mL). Copper (II) sulfate (90 mg, 0.5 mmol) was added followed by sodium tetrahydroborate (90 mg, 2.5 mmol) and the reaction was stirred 48 h. The reaction was diluted with water, filtered, and concentrated in vacuo. The residue was dissolved in ethyl acetate and precipitated with heptane. The precipitate was dissolved in dichloromethane and was chromatographed on silica gel with dichloromethane-methanol (95:5) as eluent, affording the title compound (125 mg, 50%). $^1$H-NMR (300 MHz, $d_6$ DMSO) $\delta$1.15 (t, 3H, J=7 Hz), 1.90 (m, 2H), 2.19 (m, 2H), 3.21 (q, 2H, J=7 Hz), 3.55 (s, 3H), 4.20 (m, 1H), 4.98 (dd, 1H, J=4 Hz, 6 Hz), 5.45 (dd, 1H, J=3 Hz, 7 Hz), 5.85 (d, 1H, J=6 Hz), 6.25 (d, 1H, J=3 Hz), 6.27 (dd, 1H, J=6 Hz, 16 Hz), 6.90 (d, 1H, J 16 Hz), 7.35 (m, 3H), 7.50 (d, 2H, J=7 Hz), 8.56 (s, 1H), 8.57 (s, 1H), 9.30 (t, 1H, J=5 Hz), 9.60 (s, 1H).

Example 12

3-{6-[6-(3-Ethyl-ureido)-purin-9-yl]-2-styryl-tetrahydro-furo[3,4-d][1,3]dioxol-4-yl}-propionic acid 3-{6-[6-(3-Ethyl-ureido)-purin-9-yl]-2-styryl-tetrahydro-furo[3,4-d][1,3]dioxol-4-yl}-propionic acid methyl ester (5.0 g, 10 mmol) was dissolved in tetrahydrofuran (300 mL). Water (100 mL) was added, followed by lithium hydroxide (1.0 g, 25 mmol). The solution was allowed to stir 16 h at room temperature. It was acidified to pH 5 with acetic acid, concentrated in vacuo, then extracted with chloroform (300 mL). The organic extract was evaporated, redissolved in ethyl acetate and precipitated with heptane to afford the final product (3.9 g, 80%). $^1$H-NMR (300 MHz, $d_6$ DMSO) $\delta$1.14 (t 3H, J=7 Hz), 1.90 (m, 2H), 2.19 (m, 2H), 3.26 (q, 2H, J=6 Hz), 4.17 (m, 1H), 4.93 (ψt, 1H, J=6 Hz), 5.43 (dd, 1H, J=3 Hz, 7 Hz), 5.84 (d 1H, J=6 Hz), 6.24 (d, 1H, J=3 Hz), 6.28 (dd, 1H, J=7 Hz, 13 Hz), 6.90 (d, 1H, J 16 Hz), 7.35 (m, 3H), 7.51 (d, 2H, J=7 Hz), 8.56 (s, 1H), 8.61 (s, 1H), 9.30 (t, 1H, J=6 Hz).

Example 13

Inhibition of ADP-Induced Platelet Aggregation

Isolation of Platelets: Human blood is obtained from informed healthy adult volunteers. Blood is collected into one-sixth volume of acid/citrate/dextrose (ACD) buffer (85 mM sodium citrate, 65 mM citric acid, and 110 mM glucose). Collected blood is placed in a water bath at 37° C. for 30 minutes. Blood is then centrifuged at 275×g for 16 minutes at room temperature and the platelet-rich plasma is removed and centrifuged at 2200×g for 13 minutes at room temperature. The platelet pellet is resuspended in 40 mL of HEPES-buffered Tyrode's solution (137 mM NaCl, 2.7 mM KCl, 1 mM $MgCl_2$, 2 mM $CaCl_2$, 12 mM $NaHCO_3$, 0.36 mM $NaH_2PO_4$, 5.5 mM glucose, 5 mM HEPES pH 7.4, 0.35% bovine serum albumin or 0.35% human serum albumin) containing 10 U/mL heparin and 5 μM (final concentration) prostaglandin $I_2$ ($PGI_2$). The platelet suspension is incubated in a 37° C. water bath for 10 minutes and then 5 μM (final conc.) $PGI_2$ is added just before centrifugation at 1900×g for 8 minutes. The resulting pellet is resuspended in 40 mL of HEPES-buffered Tyrode's solution containing 5 μM (final concentration) $PGI_2$ and then is incubated for 10 minutes in a 37° C. water bath. A small aliquot (500 μL) of the platelet suspension is removed for platelet counting. Prior to centrifugation 5 μM (final concentration) $PGI_2$ is added to the suspension and then the suspension is centrifuged at 1900×g for 8 minutes. The pellet is resuspended at a density of 5×10$^8$ cells/mL in HEPES-buffered Tyrode's solution containing 0.05 U/mL apyrase.

Aggregation Studies: ADP-induced platelet aggregation is determined by measuring the transmission of light through a 0.5 ml suspension of stirred (1000 rpm) washed platelets in a lumi-aggregometer at 37° C. (Chrono-Log Corp. Havertown, Pa.). The baseline of the instrument is set using 0.5 ml of Hepes-buffered Tyrode's solution. Prior to aggregation measurements, the platelet suspension is supplemented with 1 mg/ml fibrinogen. Platelet aggregation is initiated by the addition of indicated concentrations of ADP or other agonists, and the light transmission is continuously recorded for at least 8 min. When inhibitors of platelet aggregation are tested, platelets are incubated for 2 min in the presence of indicated concentrations of inhibitor before addition of ADP or other agonists, and the response is recorded for at least 8 min. The potency of agonists and inhibitors of platelet aggregation is calculated from both the rate of aggregation and the maximal extent of aggregation obtained for each determination by fitting the data to a four-parameter logistic equation using the GraphPad software package (GraphPad Corp. San Diego, Calif.).

When a broad range of concentrations of $P2Y_{12}$ antagonist is tested (usually from 1 nM to 100 μM), an $IC_{50}$ value is also obtained. $IC_{50}$ values represent the concentration of antagonist necessary to inhibit by 50% the aggregation elicited by a given concentration of ADP.

Example 14

Inhibition of ADP-induced Platelet Aggregation in Whole Blood

Human blood is obtained from informed healthy adult volunteers. Blood is collected into syringes containing heparin, sodium citrate, PPACK or hirudin as anticoagulant. Blood is carefully transferred to a conical tube and maintained at room temperature. Assays are conducted within 60 min from the collection of the blood sample. ADP-induced platelet aggregation is performed using the impedance mode of an aggregometer (Chrono-Log Corp. Havertown, Pa.). Blood is gently mixed and an aliquot of 500 μL is transferred to a measurement cuvette, then, 450 μL of warm sterile saline is added to each cuvette and the sample is stirred at 1000 rpm. The impedance probe is introduced into the cuvette and the sample is allowed to warm for approx. 3-4 minutes in the aggregometer. The basal impedance is recorded for 1 minute and then 50 µL of the appropriate concentrations of ADP are added to generate an ADP dose response curve. For the evaluation of $P2Y_{12}$ receptor antagonists on platelet aggregation, after the basal impedance is recorded for 1 minute as indicated above, blood samples are supplemented with 50 µL of the antagonist or vehicle and after 2 minutes, 50 µL of ADP ($EC_{90}$; usually 5-10 µmol/L ADP) are added and the impedance is recorded for up to 8 minutes. The potency of agonists and inhibitors of platelet aggregation is calculated from the impedance values obtained in each sample by fitting the data to a four-parameter logistic equation using the GraphPad software package (GraphPad Corp. San Diego, Calif.).

Example 15

Effects on Platelet Aggregation In Vivo

To evaluate the ability of these compounds to inhibit platelet aggregation in vivo, an experimental protocol similar to the method of R. G. Humphries et al. (Br. J. Pharmacol. 115:1110-1116, 1995) is performed.

Surgical Preparation and Instrumentation: Male Sprague-Dawley rats are anesthetized. Body temperature is maintained at 37±0.5° C. with a heating lamp. Animals breathe spontaneously and a tracheotomy is performed to ensure a patent airway. A cannula containing heparinized saline is introduced into the left femoral artery and connected to a transducer to record blood pressure and heart rate. Cannulae containing non-heparinized saline are introduced into the left common carotid artery and left jugular vein for withdrawal of arterial blood samples and intravenous administration of compounds, respectively.

Experimental Protocol: Either compound or vehicle is administered to each animal as an infusion. Blood samples are taken immediately prior to the first infusion, at the end of each infusion and 20 min after cessation of the final infusion for measurement of platelet aggregation ex vivo. Immediately after sampling, ADP-induced platelet aggregation is measured in duplicate in 0.5 ml blood samples diluted 1:1 with saline and incubated at 37° C. for 4 min. For the final minute of this period, cuvettes are transferred to a lumi-aggregometer and the sample stirred at 900 rpm. ADP (3 µM) is added in a volume of 20 µl and the aggregation response is recorded.

Example 16

Inhibition of Thrombus Formation in Anesthetized Rats

To evaluate the effect of these compounds on thrombus formation in vivo, the following experimental protocol is performed.

Rats (CD-1; male; approximately 350 grams; Charles River, Raleigh, N.C.), are anesthetized with sodium pentobarbital (70 mg/kg i.p.). The abdomens are shaved and a 22 gauge intravenous catheter is inserted into a lateral tail vein. A midline incision is made and the intestines are wrapped in saline-soaked gauze and positioned so the abdominal aorta is accessible. The inferior vena cava and abdominal aorta are carefully isolated and a section (approximately 1 cm) of the abdominal aorta (distal to the renal arteries proximal to the bifurcation) is dissected. All branches from the aorta in this section are ligated with 4-0 silk suture. A 2.5 mm diameter flow probe connected to a Transonic flow meter is placed on the artery and a baseline (pre-stenosis) flow is recorded. Two clips are placed around the artery decreasing the vessel diameter by approximately 80%. A second baseline flow measurement is taken (post-stenosis) and the hyperemic response is tested. Animals are then treated with either compound or saline intravenously via tail vein catheter. Thrombosis is induced five minutes after treatment by repeated external compressions of the vessel with hemostatic forceps. Two minutes post-injury, the vessel compressions are repeated and a 10 minute period of flow monitoring is started. Animals are monitored continuously for a minimum of the first ten minutes post-injury. After twenty minutes (post-injury), a flow measurement is repeated and the animals are euthanized. The section of the aorta that includes the injured section is harvested and placed in 10% formalin for possible histologic evaluation.

Example 17

In Vivo PK/PD Measurements Following Oral Administration

To evaluate the ability of these compounds to be absorbed orally and to inhibit platelet aggregation in vivo, the following experimental protocol is conducted.

Male Sprague-Dawley rats are anesthetized using an inhaled anesthetic. A cannula containing heparinized saline is introduced into the jugular vein for withdrawal of venous blood samples. Animals are allowed a 48-hour recovery period prior to dose administration.

Either compound or vehicle is administered to each animal as an oral gavage. Blood samples are taken immediately prior to compound administration, and at up to 12 time points ranging from 15 min to 24 hours following compound administration. HPLC-MS/MS is used to measure the amount of compound and/or metabolite in the blood samples.

Example 18

Inhibition of Thrombus Formation in Anesthetized Dogs

To evaluate the effect of the compounds of this invention on dynamic thrombus formation in vivo, the following experimental protocol, similar to the method of J. L. Romson et al. (*Thromb. Res.* 17:841-853, 1980), is performed.

Surgical Preparation and Instrumentation: Briefly, purpose-bred dogs are anesthetized, intubated and ventilated with room air. The heart is exposed by a left thoracotomy in the fifth intercostal space and suspended in a pericardial cradle. A 2-3 cm segment of the left circumflex coronary artery (LCCA) is isolated by blunt dissection. The artery is instrumented from proximal to distal with a flow probe, a stimulation electrode, and a Goldblatt clamp. The flow probe monitors the mean and phasic LCCA blood flow velocities. The stimulation electrode and its placement in the LCCA and the methodology to induce an occlusive coronary thrombus have been described previously (J. K. Mickelson et al., Circulation 81:617-627, 1990; R. J. Shebuski et al., Circulation 82:169-177, 1990; J. F. Tschopp et al., Coron. Artery Dis. 4:809-817, 1993).

Experimental Protocol: Dogs are randomized to one of four treatment protocols (n=6 per treatment group) in which the control group receives saline intravenously and the three drug-treated groups are administered compound intravenously. Upon stabilization from the surgical interventions, dogs receive either saline or compound. After approximately 30 minutes, an anodal current is applied to the LCCA for 180 min. The number and frequency of cyclic flow variations (CFV) that precede formation of an occlusive thrombus are recorded. These cyclic phenomena are caused by platelet thrombi that form in the narrowed lumen as a result of platelet aggregation (J. D. Folts et al., Circulation 54:365-370, 1976; Bush et al., Circulation 69:1161-1170, 1984). Zero flow in the LCCA for a minimum of 30 minutes indicates a lack of antithrombotic efficacy (L. G. Frederick et al., Circulation 93:129-134, 1996).

Example 19

Inhibition of ADP-Induced Aggregation by Compounds of the Invention: $IC_{50}$ Values Obtained from Washed Platelets The $IC_{50}$ values for the following compounds as inhibitors of ADP-induced aggregation of washed platelets were determined using the procedures provided in Example 13:

4-{2,2-Dimethyl-6-[6-(3-phenyl-ureido)-purin-9-yl]-tetrahydro-furo[3,4-d][1,3]dioxol-4-ylmethoxy}-isophthalic acid: $IC_{50}$=6.59 micromolar.

2-[6-[6-(3-Phenyl-ureido)-purin-9-yl]-2-(2-trifluoromethyl-phenyl)-tetrahydro-furo[3,4-d][1,3]dioxol-4-ylmethoxy]-nicotinic acid $IC_{50}$=8.07 micromolar.

2-{2-Naphthalen-2-yl-6-[6-(3-phenyl-ureido)-purin-9-yl]-tetrahydro-furo[3,4-d][1,3]dioxol-4-ylmethoxy}-nicotinic acid $IC_{50}$=18 micromolar.

2-{6-[6-(3-Hexyl-ureido)-purin-9-yl]-2-phenyl-tetrahydro-furo[3,4-d][1,3]dioxol-4-ylmethoxy}-nicotinic acid $IC_{50}$=2.15 micromolar.

2-{6-[6-(3-Ethyl-ureido)-purin-9-yl]-2-phenylethynyl-tetrahydro-furo[3,4-d][1,3]dioxol-4-ylmethoxy}-nicotinic acid $IC_{50}$=1.0 micromolar.

1-{2-Benzyl-6-[6-(3-cyclopentyl-ureido)-purin-9-yl]-tetrahydro-furo[3,4-d][1,3]dioxol-4-carbonyl}-pyrrolidine-2-carboxylic acid $IC_{50}$=0.75 micromolar.

1-(9-{2-Benzyl-6-[(3-methylsulfonyl-ureido)-methyl]-tetrahydro-furo[3,4-d][1,3]dioxol-4-yl}-9H-purin-6-yl)-3-phenyl-urea $IC_{50}$=15 micromolar.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method of treating diseases or conditions associated with increased platelet aggregation comprising:
administering to a subject a pharmaceutical composition comprising a therapeutically effective amount of a compound of Formula III, or a pharmaceutically acceptable hydrate, solvate or salt thereof, wherein said amount is effective to inhibit platelet aggregation,

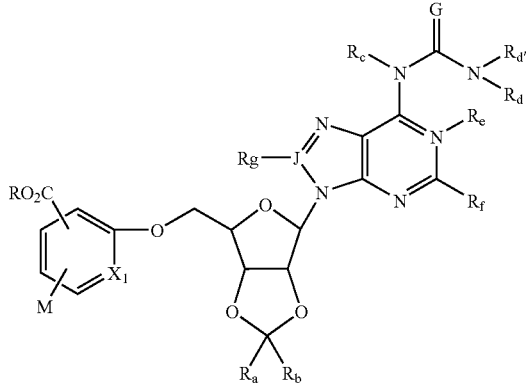

Formula III wherein
R is H, or saturated or unsaturated $C_{1-8}$ alkyl;
$R_a$ and $R_c$ is H;
$R_b$ is selected from the group consisting of: saturated or unsaturated $C_{1-8}$ alkyl, saturated or unsaturated $C_{3-7}$ cycloalkyl, aralkyl, and aryl; where all rings or chains optionally bear one or more desired substituents;
$R_d$ and $R_{d'}$ are independently selected from the group consisting of: H, saturated or unsaturated $C_{1-8}$ alkyl, saturated or unsaturated $C_{3-7}$ cycloalkyl, aralkyl, aryl;
$R_e$ is absent;
$R_f$ and $R_g$ are independently selected from the group consisting of: H, halogen, saturated or unsaturated $C_{1-8}$ alkyl, saturated or unsaturated $C_{3-7}$ cycloalkyl, aryl, aralkyl;
G is O;
J is carbon:
$X_1$ is selected from the group consisting of: N and C-M; and
M is selected from the group consisting of: —H, halogen, —$CF_3$, saturated or unsaturated $C_{1-8}$ alkyl, saturated or unsaturated $C_{3-7}$ cycloalkyl, —OH, saturated or unsaturated $C_{1-6}$ alkoxy, amino, —N-substituted amino, and N,N-disubstituted amino.

2. The method according to claim 1, wherein said compound is selected from the group consisting of: 2-{2-Phenyl-6-[6-(3-phenyl-ureido)-purin-9-yl]-tetrahydro-furo[3,4-d][1,3]dioxol-4-ylmethoxy}-nicotinic acid; 2-{2-Biphenyl-3-yl-6-[6-(3-phenyl-ureido)-purin-9-yl]-tetrahydro-furo[3,4-d][1,3]dioxol-4-ylmethoxy}-nicotinic acid; 2-{2-Naphthalen-2-yl-6-[6-(3-phenyl-ureido)-purin-9-yl]-tetrahydro-furo[3,4-d][1,3]dioxol-4-ylmethoxy}-nicotinic acid; 2-{6-[6-(3-Hexyl-ureido)-purin-9-yl]-2-phenyl-tetrahydro-furo[3,4-d][1,3]dioxol-4-ylmethoxy}-nicotinic acid; 2-{6-[6-(3-Ethyl-ureido)-purin-9-yl]-2-phenethyl-tetrahydro-furo[3,4-d][1,3]dioxol-4-ylmethoxy}-nicotinic acid; 2-{6-[6-(3-Ethyl-ureido)-purin-9-yl]-2-phenylethynyl-tetrahydro-furo[3,4-d][1,3]dioxol-4-ylmethoxy}-nicotinic acid; 2-{6-[6-(3-Ethyl-ureido)-purin-9-yl]-2-phenyl-tetrahydro-furo[3,4-d][1,3]dioxol-4-ylmethoxy}-nicotinic acid; 2-{2-(2-Bromo-phenyl)-6-[6-(3-ethyl-ureido)-purin-9-yl]-tetrahydro-furo[3,4-d][1,3]dioxol-4-ylmethoxy}-nicotinic acid; 2-{6-[6-(3-Cyclopentyl-ureido)-purin-9-yl]-2-phenethyl-tetrahydro-furo[3,4-d][1,3]dioxol-4-ylmethoxy}-nicotinic acid; 2-{6-[6-(3-Cyclopentyl-ureido)-purin-9-yl]-2-p-tolyl-tetrahydro-furo[3,4-d][1,3]dioxol-4-ylmethoxy}-nicotinic acid; 2-{2-Biphenyl-4-yl-6-[6-(3-hexyl-ureido)-purin-9-yl]-tetrahydro-furo[3,4-d][1,3]dioxol-4- ylmethoxy}-nicotinic acid; 2-{2-(4-Acetylamino-phenyl)-6-[6-(3-cyclopentyl-ureido)-purin-9-yl]-tetrahydro-furo[3,4-d][1,3]dioxol-4-ylmethoxy}-nicotinic acid; and 2-{2-tert-Butyl-6-[6-(3-phenyl-ureido)-purin-9-yl]-tetrahydro-furo[3,4-d][1,3]dioxol-4-ylmethoxy}-nicotinic acid.

3. The method according to claim 1, wherein said pharmaceutical composition comprises a pharmaceutically-acceptable carrier.

4. The method according to claim 1, wherein said compound is used in combination with a therapeutic agent that is useful for treating platelet aggregation disorders or diseases.

5. The method according to claim 4, wherein said therapeutic agent is selected from the group consisting of: a GP IIb/IIIa antagonist, Abciximab, a thrombin inhibitor, hirudin, aspirin, heparin, low molecular weight heparin, warfarin, and an adenosine $A_{2a}$ receptor agonist.

6. The method according to claim 1, wherein said compound is administered orally, topically, or parenterally, in an amount effective to reduce platelet aggregation in a subject in need of such treatment.

7. A pharmaceutical composition comprising a pharmaceutically acceptable carrier and a therapeutically effective amount of a compound of Formula III, as defined in claim 1, or a pharmaceutically acceptable hydrate, solvate or salt thereof.

8. The method according to claim 1, wherein said disease is stroke or angina.

9. The method according to claim 1, wherein said disease is myocardial infarction or peripheral arterial disease.

10. The method according to claim 1, wherein said condition is coronary angioplasty.

11. The method according to claim 1, wherein said condition is thrombus formation.

12. The method according to claim 1, wherein said compound is

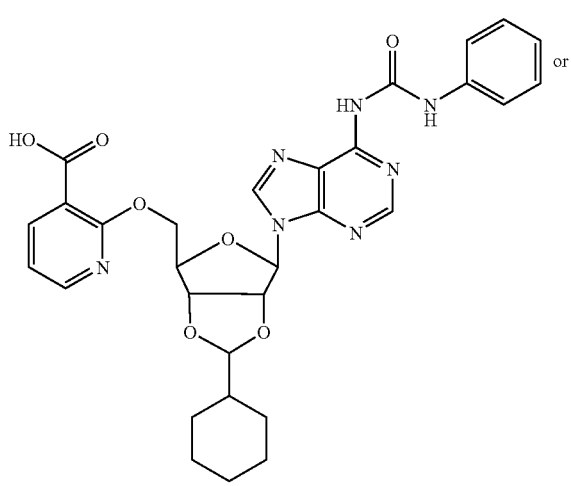

or

-continued

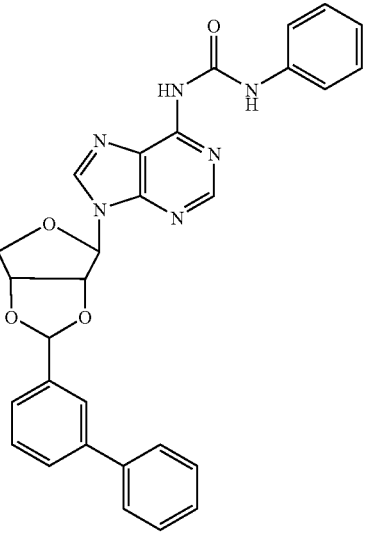

13. The pharmaceutical composition according to claim 7, wherein said compound is selected from the group consisting of: 2-{2-Phenyl-6-[6-(3-phenyl-ureido)-purin-9-yl]-tetrahydro-furo[3,4-d][1,3]dioxol-4-ylmethoxy}-nicotinic acid; 2-{2-Biphenyl-3-yl-6-[6-(3-phenyl-ureido)-purin-9-yl]-tetrahydro-furo[3,4-d][1,3]dioxol-4-ylmethoxy}-nicotinic acid; 2-{2-Naphthalen-2-yl-6-[6-(3-phenyl-ureido)-purin-9-yl]-tetrahydro-furo[3,4-d][1,3]dioxol-4-ylmethoxy}-nicotinic acid; 2-{6-[6-(3-Hexyl-ureido)-purin-9-yl]-2-phenyl-tetrahydro-furo[3,4-d][1,3]dioxol-4-ylmethoxy}-nicotinic acid; 2-{6-[6-(3-Ethyl-ureido)-purin-9-yl]-2-phenethyl-tetrahydro-furo[3,4-d][1,3]dioxol-4-ylmethoxy}-nicotinic acid; 2-{6-[6-(3-Ethyl-ureido)-purin-9-yl]-2-phenyl-tetrahydro-furo[3,4-d][1,3]dioxol-4-ylmethoxy}-nicotinic acid; 2-{6-[6-(3-Ethyl-ureido)-purin-9-yl]-2-phenyl-tetrahydro-furo[3,4-d][1,3]dioxol-4-ylmethoxy}-nicotinic acid; 2-{2-(2-Bromo-phenyl)-6-[6-(3-ethyl-ureido)-purin-9-yl]-tetrahydro-furo[3,4-d][1,3]dioxol-4-ylmethoxy}-nicotinic acid; 2-{6-[6-(3-Cyclopentyl-ureido)-purin-9-yl]-2-phenethyl-tetrahydro-furo[3,4-d][1,3]dioxol-4-ylmethoxy}-nicotinic acid; 2-{6-[6-(3-Cyclopentyl-ureido)-purin-9-yl]-2-p-tolyl-tetrahydro-furo[3,4-d][1,3]dioxol-4-ylmethoxy}-nicotinic acid; 2-{2-Biphenyl-4-yl-6-[6-(3-hexyl-ureido)-purin-9-yl]-tetrahydro-furo[3,4-d][1,3]dioxol-4-ylmethoxy}-nicotinic acid; 2-{2-(4-Acetylamino-phenyl)-6-[6-(3-cyclopentyl-ureido)-purin-9-yl]-tetrahydro-furo[3,4-d][1,3]dioxol-4-ylmethoxy}-nicotinic acid; and 2-{2-tert-Butyl-6-[6-(3-phenyl-ureido)-purin-9-yl]-tetrahydro-furo[3,4-d][1,3]dioxol-4-ylmethoxy}-nicotinic acid.

14. A method of inhibiting platelet aggregation in blood and blood products that contain platelets, comprising administering to the blood or blood products an effective amount of a compound of Formula III, or a pharmaceutically acceptable hydrate, solvate or salt thereof, wherein said amount is effective to inhibit platelet aggregation in the blood or blood products, Formula III

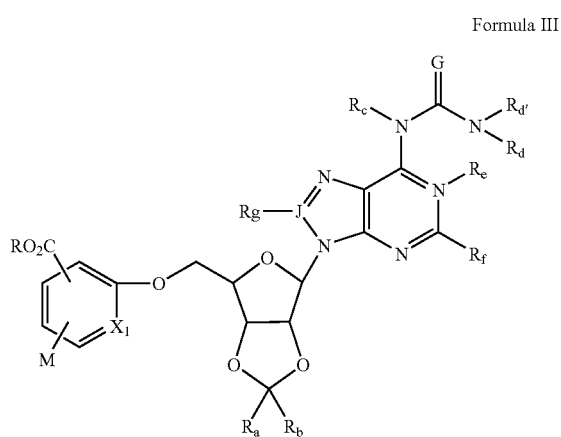

wherein R is H, or saturated or unsaturated $C_{1-8}$ alkyl;
$R_a$ and $R_c$ is H;
$R_b$ is selected from the group consisting of: hydrogen, saturated or unsaturated $C_{1-8}$ alkyl, saturated or unsaturated $C_{3-7}$ cycloalkyl, aralkyl, and aryl; where all rings or chains optionally bear one or more desired substituents; $R_d$ and $R_{d'}$ are independently selected from the group consisting of: H, saturated or unsaturated $C_{1-8}$ alkyl, saturated or unsaturated $C_{3-7}$ cycloalkyl, aralkyl, aryl;

$R_e$ is absent;

$R_f$ and $R_g$ are independently selected from the group consisting of: H, halogen, saturated or unsaturated $C_{1-8}$ alkyl, saturated or unsaturated $C_{3-7}$ cycloalkyl, aryl, aralkyl;

G is O;

J is carbon:

$X_1$ is selected from the group consisting of: N and C-M; and

M is selected from the group consisting of: —H, halogen, —$CF_3$, saturated or unsaturated $C_{1-8}$ alkyl, saturated or unsaturated $C_{3-7}$ cycloalkyl, OH, saturated or unsaturated $C_{1-6}$ alkoxy, amino, —N-substituted amino, and N,N-disubstituted amino.

* * * * *